US007595402B2

United States Patent

(12) United States Patent
Miller et al.

(10) Patent No.: US 7,595,402 B2
(45) Date of Patent: Sep. 29, 2009

(54) PRODRUGS OF SELECTIVE ANDROGEN RECEPTOR MODULATORS AND METHODS OF USE THEREOF

(75) Inventors: Duane D. Miller, Germantown, TN (US); Mitchell S. Steiner, Germantown, TN (US); Karen A. Veverka, Cordova, TN (US); James T. Dalton, Upper Arlington, OH (US)

(73) Assignee: GTx, Inc., Memphis, TN (US)

( * ) Notice: Subject to any disclaimer, the term of this patent is extended or adjusted under 35 U.S.C. 154(b) by 419 days.

(21) Appl. No.: 11/013,214

(22) Filed: Dec. 16, 2004

(65) Prior Publication Data

US 2006/0009488 A1 Jan. 12, 2006

Related U.S. Application Data

(60) Provisional application No. 60/529,573, filed on Dec. 16, 2003.

(51) Int. Cl.
*C07D 215/38* (2006.01)

(52) U.S. Cl. ........................ 546/158; 546/153; 546/157

(58) Field of Classification Search ................. 546/158; 564/153, 157
See application file for complete search history.

(56) References Cited

U.S. PATENT DOCUMENTS

| | | | | |
|---|---|---|---|---|
| 3,875,229 | A | 4/1975 | Gold | |
| 4,139,638 | A | 2/1979 | Neri et al. | |
| 4,191,775 | A | 3/1980 | Glen | |
| 4,239,776 | A | 12/1980 | Glen et al. | |
| 4,282,218 | A | 8/1981 | Glen et al. | |
| 4,386,080 | A | 5/1983 | Crossley et al. | |
| 4,465,507 | A | 8/1984 | Konno et al. | |
| 4,636,505 | A | 1/1987 | Tucker | |
| 4,880,839 | A | 11/1989 | Tucker | |
| 5,162,504 | A | 11/1992 | Horoszewicz | |
| 5,609,849 | A | 3/1997 | Kung | |
| 5,656,651 | A | 8/1997 | Sovak et al. | |
| 6,019,957 | A | 2/2000 | Miller et al. | |
| 6,071,957 | A | 6/2000 | Miller et al. | |
| 6,160,011 | A | 12/2000 | Miller et al. | |
| 6,492,554 | B2 * | 12/2002 | Dalton et al. | 564/158 |
| 6,569,896 | B2 | 5/2003 | Dalton et al. | |
| 6,995,284 | B2 | 2/2006 | Dalton et al. | |
| 2001/0012839 | A1 | 8/2001 | Miller et al. | |
| 2004/0014975 | A1 | 1/2004 | Dalton et al. | |
| 2004/0029913 | A1 | 2/2004 | Dalton et al. | |
| 2004/0260092 | A1 | 12/2004 | Miller et al. | |
| 2005/0137172 | A1 | 6/2005 | Dalton et al. | |

FOREIGN PATENT DOCUMENTS

| | | | |
|---|---|---|---|
| EP | 0 040 932 | | 2/1981 |
| EP | 0 100 172 | | 2/1984 |
| EP | 00198352 | | 1/1989 |
| EP | 0253 503 | | 12/1991 |
| JP | 52128329 | | 10/1977 |
| WO | 90/08128 | * | 7/1990 |
| WO | WO 95/19770 | | 7/1995 |
| WO | WO 98/53826 | | 12/1998 |
| WO | WO 01/12579 | | 2/2001 |
| WO | WO 01/28990 | | 4/2001 |
| WO | WO 03/074473 | | 9/2003 |
| WO | WO 2005/000794 | | 1/2005 |

OTHER PUBLICATIONS

U.S. Appl. No. 09/644,970, filed Aug. 2, 2000, Dalton et al.

C. G. Francisco, et al., “Long-acting contraceptive agents: testosterone esters of unsaturated acids”, Steroids, Jan. 1990, vol. 55, Butterworths.

Carl Djerassi and S.P. Leibo, “A new look at male contraception”, Nature, vol. 370, pp. 11-12 , 1983.

D. McKillop, et al., “Enantioselective metabolism and pharmacokinetics of Casodex in the male rat”, Xenobiotica, 1995, vol. 25, No. 6, 623-634.

David J. Handelsman, “Bridging the gender gap in contraception: another hurdle cleared” The Medical Journal of Australia, vol. 154, Feb. 18, 1996, pp. 230-233.

David T. Baird and Anna F. Glasier, “Hormonal Contraception—Drug Therapy”, The New England Journal of Medicine, May 27, 1993, pp. 1543-1549.

F.C. W. Wu, “Male Contraception: Current Status and Future Prospects”, Clinical Endocrinology, (1988), 29, pp. 443-465.

Howard Tucker and Glynne J. Chesterson, “Resolution of the Nonsteroidal Antiandrogen—4'-Cyano-3-[(4-fluorophenyl)sulfonyl]-2-hydroxy-2-methyl-3'-(trifluoromethyl)-propionanilide and the Determination of the Absolute Configuration of the Active Enantiomer” J. Med Chem. 1988, 31, pp. 885-887.

John M. Hoberman and Charles E. Yesalis, “The History of Synthetic Testosterone”, Scientific American, Feb. 1995, pp. 76-81.

Leonid Kirkovsky, et al., “[$^{125}$I]-Radionated Bicalutamide Analogs as Potential Imaging Agents for Prostate Cancer”, Poster Presentation MEDI 155, 214th ACS National Meeting, Las Vegas, NV, Sep. 7-11, 1997, Department of Pharmaceutical Sciences, University of Tennessee, Memphis, TN 38163.

(Continued)

*Primary Examiner*—D. Margaret Seaman
(74) *Attorney, Agent, or Firm*—Mark S. Cohen; Pearl Cohen Zedek Latzer, LLP

(57) ABSTRACT

The present invention provides prodrugs of selective androgen receptor modulators (SARMs), and their use in treating or reducing the incidence of osteoporosis, a variety of hormone-related conditions, conditions associated with Androgen Decline in Aging Male (ADAM); conditions associated with Androgen Decline in Female (ADIF), and muscular wasting conditions, obesity, dry eye conditions, and prostate cancer. The prodrugs are also useful in oral androgen replacement therapy and male contraception.

11 Claims, 8 Drawing Sheets

OTHER PUBLICATIONS

Leonid Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.

World Health Organisation Task Force on Methods for the Regulation of Male Fertility, "Contraceptive efficacy of testosterone-induced azoospermia in normal men", The Lancet, vol. 336, Oct. 20, 1990, pp. 955-959and 1517-1518.

Corey (1987) "Asymmetric Bromolactonization Reaction: Synthesis of Optically Active 2-hydroxy-2-Methylalkanoic Acids from 2-Methylalkanoic Acids" Tetrahedron Letters vol. 28, No. 25 2801-2804.

Dalton JT, Mukherjee A, Zhu Z, Kirkovsky L, and Miller DD. Discovery of Nonsteroidal Androgens. Biochem. Biophys. Res. Commun.,244(1): 1-4, 1998.

Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4-(trifluoromethyl)-2H-pyrano[3,2-g]quinolin-2-one. Bioorg. Med. Chem. Lett., 9: 1003, 1999.

Edwards JP, West SJ, Pooley CLF, Marschke KB, Farmer LJ, and Jones TK. New nonsteroidal androgen receptor modulators based on 4-(trifluoromethyl)-2-(1H)-Pyrololidino[3,2-g]quinolone. Bioorg. Med. Chem. Lett., 8: 745, 1998.

Hamann LG, Mani NS, Davis RL, Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210, 1999.

Higuchi RI, Edwards JP, Caferro TR, Ringgenberg JD, Kong JW, Hamann LG, Arienti KL, Marschke KB, Davis RL, Farmer LJ, and Jones TK, 4-Alkyl- and 3,4-diakyl-1,2,3,4-tetrahydro-8-pyridono[5,6-g]quinolines: potent, nonsteroidal androgen receptor agonists. Bioorg. Med. Chem. Lett., 9:1335,1999.

Kirkovsky, et al (2000) "Chiral nonsteroidal affinity ligands for the androgen receptor. 1. Bicalutamide analogues bearing electrophilic groups in the B aromatic ring." J Med Chem 43, 581-590.

Rosen J, Day A, Jones TK, Jones ET, Nadzan AM, and Stein RB. Intracellular receptor and signal transducers and activators of transcription superfamilies: novel targets for small-molecule drug discovery. J. Med. Chem., 38: 4855, 1995.

Terashima, et al (1979) "Asymmetric Halolactonsation Reaction-1" Tetrahedron Letters vol. 35 2337-2343.

Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.

Steinberger et al., "Effect of chronic administration of testosterone enanthate on sperm production and plasma testosterone, follicle-stimulating hormone, and luteinizing hormone levels: a preliminary evaluation of a possible male contraceptive." Fertility and Sterility 28: 1320-28, 1977.

Taniguchi, et al (1981) "Permeation and Hydrolysis of TRichloroethyl Phosphate in the Rat Intestine." Chemical and Pharmaceutical Bulletin, Pharmaceutical Society of Japan, Tokyo. vol. 29 No. 1 200-204.

Cushman, et al (1991) "Synthesis and evaluation of stilbene and dihydrostilbene derivatives as potential anticancer agents that inhibit tubulin polymerization" Journal of Medicinal Chemisrty, vol. 34 2579-2588.

Ohsumi, et al (1998) "Novel combretastatin analogues effective against murine solid tumors: design and structure-activity relationships" Journal of Medicinal Chemistry vol. 41 3022-3032.

Wood, et al (1995) "The interaction with tubulin of a series of stilbenes based on combretastatin A-4" British Journal of Cancer vol. 71 705-711.

* cited by examiner

*SCHEMETIC ROUTE AND SYNTHETIC PROCEDURE FOR THE PHOSPHATE ESTER PRODRUGS*

SCHEME

SCHEMETIC ROUTE AND SYNTHETIC PROCEDURE FOR THE PHOSPHATE ESTER PRODRUGS

SCHEME

Androgenic and anabolic activity of compound VIII

Androgenic and anabolic activity of compound IX

AVERAGE PLASMA CONCENTRATION-TIME PROFILES OF COMPOUND VIII IN BEAGLE DOGS AFTER IV ADMINISTRATION AT 3 AND 10 mg/kg. EACH DATA POINT REPRESENTS THE MEAN ± STANDARD DEVIATION OF 3 ANIMALS.

AVERAGE PLASMA CONCENTRATION-TIME PROFILES OF COMPOUND VIII IN BEAGLE DOGS AFTER PO ADMINISTRATION AS SOLUTION AT 10 mg/kg. EACH DATA POINT REPRESENTS THE MEAN ± STANDARD DEVIATION OF 3 ANIMALS.

Plasma concentration-time profiles of compound VIII in beagle dogs after PO administration as capsules at 10 mg/kg.

PRODRUGS OF SELECTIVE ANDROGEN RECEPTOR MODULATORS AND METHODS OF USE THEREOF

CROSS REFERENCE TO RELATED APPLICATION

This application claims priority of U.S. Provisional Application Ser. No. 60/529,573, filed Dec. 16, 2003. This application is hereby incorporated in its entirety by reference herein.

GOVERNMENT INTEREST STATEMENT

This invention was made in whole or in part with government support under grant number R29 CA068096 awarded by the National Cancer Institute, National Institute of Health, and under grant number R15 HD35329, awarded by the National Institute of Child Health and Human Development, National Institute of Health. The government may have certain rights in the invention.

FIELD OF INVENTION

The present invention provides prodrugs of selective androgen receptor modulators (SARMs), and their use in treating or reducing the incidence of osteoporosis, a variety of hormone-related conditions, conditions associated with Androgen Decline in Aging Male (ADAM); conditions associated with Androgen Decline in Female (ADIF), and muscular wasting conditions, obesity, dry eye conditions, and prostate cancer. The prodrugs are also useful in oral androgen replacement therapy and male contraception.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids that are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern. The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions. Because the AR is involved in male sexual development and function, the AR is a likely target for effecting male contraception or other forms of hormone replacement therapy.

Administration of the male sex steroids (e.g., testosterone and its derivatives) has shown particular promise in this regard due to the combined gonadotropin-suppressing and androgen-substituting properties of these compounds (Steinberger et al., Fertility and Sterility 28: 1320-28, 1977). Chronic administration of high doses of testosterone completely abolishes sperm production (azoospermia) or reduces it to a very low level (oligospermia).

A variety of testosterone esters have been developed which are more slowly absorbed after intramuscular injection and thus result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection Non-steroidal ligands that bind the AR and act as androgens or as antiandrogens have not been reported. For this reason, research on AR agonists and antagonists has focused on steroidal compounds.

New innovative approaches are urgently needed at both the basic science and clinical levels to develop compounds which are useful for a) male contraception; b) treatment of a variety of hormone-related conditions, for example conditions associated with ADAM, such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; and/or g) decreasing the incidence of, halting or causing a regression of prostate cancer

SUMMARY OF THE INVENTION

This invention provides prodrugs of SARM compounds. Several of the parent SARM compounds have androgenic and anabolic activity of a nonsteroidal ligand for the androgen receptor. The parent SARM compounds, either alone or as a composition, are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; g) decreasing the incidence of, halting or causing a regression of prostate cancer; and/or h) inducing apoptosis in a cancer cell.

Thus, in one embodiment, the present invention provides a prodrug of a SARM compound, wherein the SARM compound is represented by a structure of formula I:

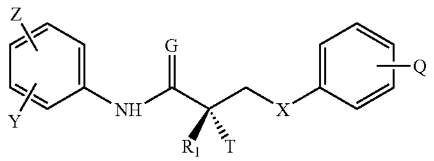

I wherein

G is O or S;

X is 0;

T is OH, OR, —$NHCOCH_3$, or NHCOR;

Z is $NO_2$, CN, COOH, COR, NHCOR or CONHR;

Y is $CF_3$, F, I, Br, Cl, CN, $CR_3$ or $SnR_3$;

Q is acetamido or trifluioacetamido;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH; and $R_1$ is $CH_3$, $CH_2F$, $CHF_2$, $CF_3$, $CH_2CH_3$, or $CF_2CF_3$, In one embodiment, G in compound I is O. In another embodiment, T in compound I is OH. In another embodiment, $R_1$ in compound I is $CH_3$. In another embodiment, Z in compound I is $NO_2$. In another embodiment, Z in compound I is CN. In another embodiment, Y in compound I is $CF_3$. In another embodiment, Q in compound I is $NHCOCH_3$. In another embodiment, Q in compound I is in the para position. In another embodiment, Z in compound I is in the para position. In another embodiment, Y in compound I is in the meta position In another embodiment, G in compound I is O, T is OH, $R_1$ is $CH_3$, Z is $NO_2$, Y is $CF_3$, and Q is $NHCOCH_3$. In another embodiment, G in compound I is O, T is OH, Z is CN, Y is $CF_3$, and Q is $NHCOCH_3$.

In another embodiment, the present invention provides a prodrug of a SARM compound, wherein the SARM compound is represented by a structure of formula II:

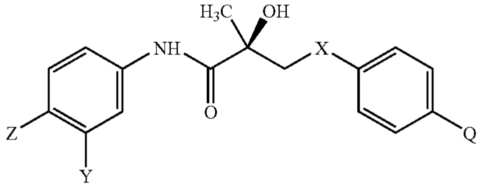

II wherein

X is O;

Z is $NO_2$, CN, COOH, COR, NHCOR or CONHR;

Y is $CF_3$, F, I, Br, Cl, CN, $CR_3$ or $SnR_3$;

Q is acetamido or trifluoroacetamido;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH; and $R_1$ is $CH_3$, $CH_2F$, $CHF_2$, $CF_3$, $CH_2CH_3$, or $CF_2CF_3$.

In another embodiment, the present invention provides a prodrug of a SARM compound, wherein the SARM compound is represented by a structure of formula V:

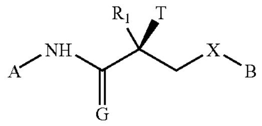

V wherein

X is a bond, O, CH2, NH, Se, PR, NO or NR;

G is O or S;

R1 is CH3, CH2F, CHF2, CF3, CH2CH3, or CF2CF3;

T is OH, OR, —NHCOCH3, or NHCOR;

R is alkyl, haloalkyl, dihaloalkyl, trihaloalkyl, CH2F, CHF2, CF3, CF2CF3, aryl, phenyl, F, I, Br, Cl, alkenyl or OH;

A is a ring selected from:

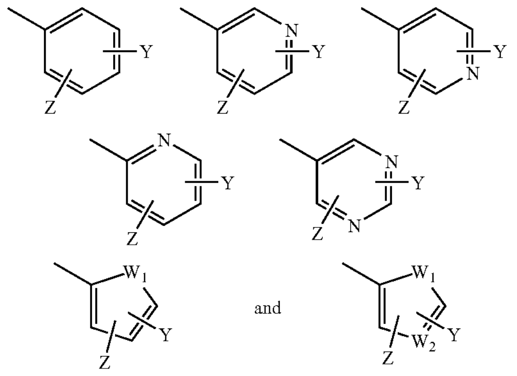

B is a ring selected from:

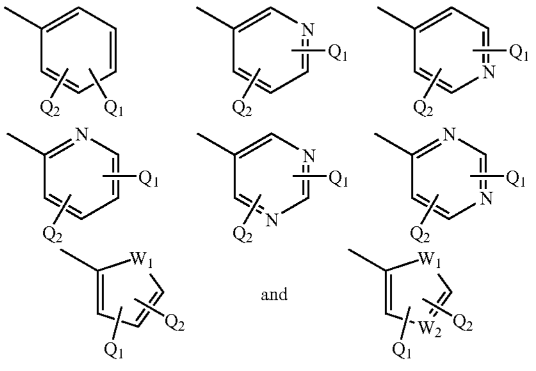

wherein A and B are not simultaneously a benzene ring;

Z is $NO_2$, CN, COOH, COR, NHCOR or CONHR;

Y is CF3, F, I, Br, Cl, CN, CR3 or SnR3;

Q1 and Q2 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO,

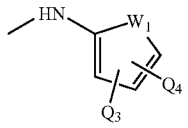

or

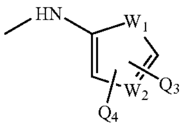

Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHC-SCF3, NHCSR NHSO2CH3, NHSO2R, OR, COR, OCOR, OSO2R, SO2R or SR, SCN, NCS, OCN, or NCO;

W1 is O, NH, NR, NO or S; and

W2 is N or NO.

In another embodiment, the present invention provides a prodrug of a SARM compound, wherein the SARM compound is represented by a structure of formula VI:

VI

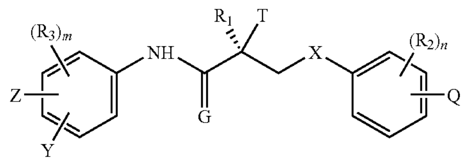

wherein

X is a bond, O, CH2, NH, Se, PR, NO or NR;

G is O or S;

T is OH, OR, —NHCOCH3, or NHCOR;

R is alkyl, haloalkyl, dihaloalkyl, trihaloalkyl, CH2F, CHF2, CF3, CF2CF3, aryl, phenyl, F, I, Br, Cl, alkenyl or OH;

R1 is CH3, CH2F, CHF2, CF3, CH2CH3, or CF2CF3;

R2 is F, Cl, Br, I, CH3, CF3, OH, CN, NO2, NHCOCH3, NHCOCF3, NHCOR, alkyl, arylalkyl, OR, NH2, NHR, NR2, SR, SCN, NCS, OCN, or NCO;

R3 is F, Cl, Br, I, CN, NO2, COR, COOH, CONHR, CF3, SnR3, or R3 together with the benzene ring to which it is attached forms a fused ring system represented by one of the structures:

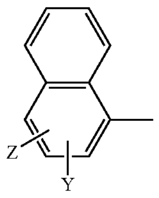

or

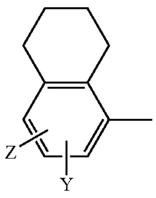

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHC-SCF3, NHCSR, NHSO2CH3, NHSO2R, OH, OR, COR, OCOR, OSO2R, SO2R, or SR; or Q together with the benzene ring to which it is attached is a fused ring system represented by structure A, B or C:

A

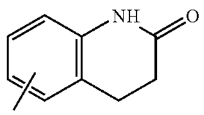

B

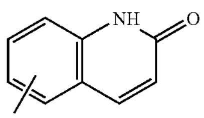

C

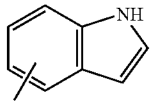

n is an integer of 1-4; and m is an integer of 1-3.

In another embodiment, the present invention provides a prodrug of a SARM compound, wherein the SARM compound is represented by a structure of formula VII:

VII

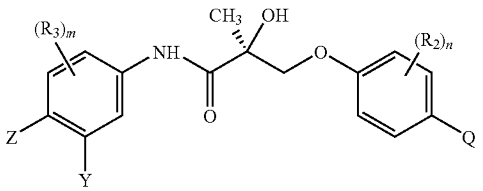

wherein

R2 is F, Cl, Br, I, CH3, CF3, OH, CN, NO2, NHCOCH3, NHCOCF3, NHCOR, alkyl, arylalkyl, OR, NH2, NHR, NR2, SR;

R3 is F, Cl, Br, I, CN, NO2, COR, COOH, CONHR, CF3, or SnR3, or R3 together with the benzene ring to which it is attached forms a fused ring system represented by one of the structures:

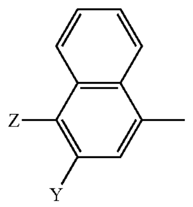

or

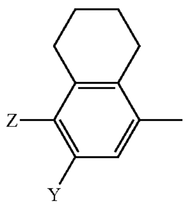

R is alkyl, haloalkyl, dihaloalkyl, trihaloalkyl, CH2F, CHF2, CF3, CF2CF3, aryl, phenyl, F, I, Br, Cl, alkenyl or OH;

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHC-SCF3, NHCSR, NHSO2CH3, NHSO2R, OH, OR, COR, OCOR, OSO2R, SO2R, or SR; or Q together with the benzene ring to which it is attached is a fused ring system represented by structure A, B or C:

A

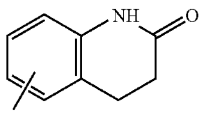

B

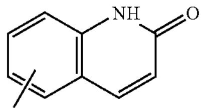

C

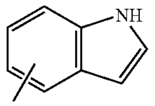

n is an integer of 1-4; and m is an integer of 1-3.

In another embodiment, the present invention provides a prodrug of a SARM compound, wherein the SARM compound is represented by a structure of formula VIII:

VIII

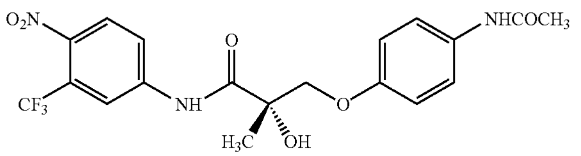

In another embodiment, the present invention provides a prodrug of a SARM compound, wherein the compound is represented by a structure of formula XI:

XI

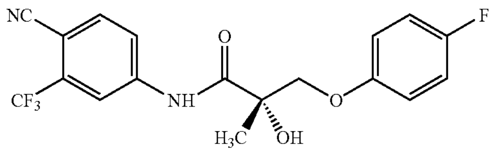

In another embodiment, the present invention provides a prodrug of a SARM compound, wherein the SARM compound is represented by a structure of formula XIII:

XIII

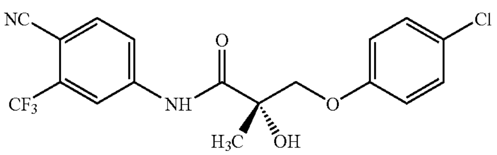

In another embodiment, the present invention provides a prodrug of a SARM compound, wherein the SARM compound is represented by a structure of formula XIV:

XIV

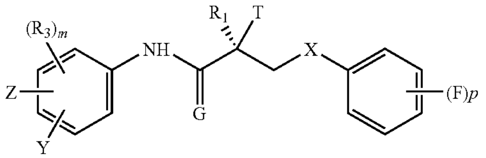

wherein

X is a bond, O, CH2, NH, Se, PR, NO or NR;

G is O or S;

T is OH, OR, —NHCOCH3, or NHCOR;

R is alkyl, haloalkyl, dihaloalkyl, trihaloalkyl, CH2F, CHF2, CF3, CF2CF3, aryl, phenyl, F, I, Br, Cl, alkenyl or OH;

R1 is CH3, CH2F, CHF2, CF3, CH2CH3, or CF2CF3;

R2 is F, Cl, Br, I, CH3, CF3, OH, CN, NO2, NHCOCH3, NHCOCF3, NHCOR, alkyl, arylalkyl, OR, NH2, NHR, NR2, SR, SCN, NCS, OCN, or NCO;

R3 is F, Cl, Br, I, CN, NO2, COR, COOH, CONHR, CF3, SnR3, or R3 together with the benzene ring to which it is attached forms a fused ring system represented by one of the structures:

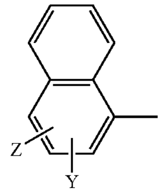

or

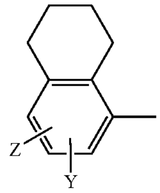

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3; NHCSR, NHSO2CH3, NHSO2R, OH, OR, COR, OCOR, OSO2R, SO2R, or SR; or Q together with the benzene ring to which it is attached is a fused ring system represented by structure A, B or C:

A

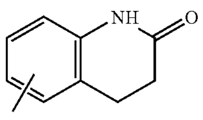

B

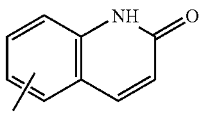

C

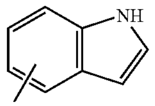

n is an integer of 1-4;

m is an integer of 1-3; and p is an integer between 2-5, inclusive.

In another embodiment, the present invention provides a prodrug of a SARM compound, wherein the SARM compound is represented by a structure of formula XVII:

XVII

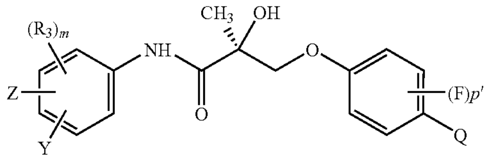

wherein

R2 is F, Cl, Br, I, CH3, CF3, OH, CN, NO2, NHCOCH3, NHCOCF3, NHCOR, alkyl, arylalkyl, OR, NH2, NHR, NR2, SR;

R3 is F, Cl, Br, I, CN, NO2, COR, COOH, CONHR, CF3, or SnR3, or R3 together with the benzene ring to which it is attached forms a fused ring system represented by one of the structures:

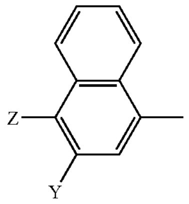

or

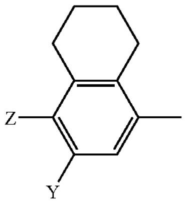

R is alkyl, haloalkyl, dihaloalkyl, trihaloalkyl, CH2F, CHF2, CF3, CF2CF3, aryl, phenyl, F, I, Br, Cl, alkenyl or OH;

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OH, OR, COR, OCOR, OSO2R, SO2R, or SR; or Q together with the benzene ring to which it is attached is a fused ring system represented by structure A, B or C:

A

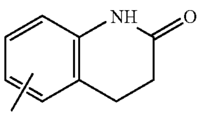

B

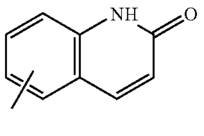

C

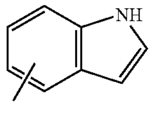

n is an integer of 1-4;

m is an integer of 1-3; and p' is an integer between 1-4, inclusive.

In another embodiment, the present invention provides a prodrug of a SARM compound, wherein the SARM compound is represented by a structure of formula IV:

IV

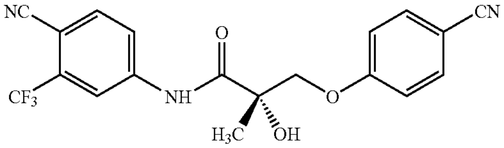

In another embodiment, the present invention provides a composition comprising a prodrug of a SARM of the present invention; and a suitable carrier or diluent. In another embodiment, the present invention provides a pharmaceutical composition comprising an effective amount of a prodrug of a SARM of the present invention; and a pharmaceutically acceptable carrier or diluent.

In another embodiment, the present invention provides a method of suppressing spermatogenesis in a subject, comprising contacting the subject with a prodrug of a SARM, in an amount effective to suppress sperm production.

In another embodiment, the present invention provides a method of contraception of a male subject, comprising contacting the male subject with a prodrug of a SARM, in an amount effective to suppress sperm production in the male subject, thereby effecting contraception of a subject.

In another embodiment, the present invention provides a method of hormone therapy of a subject, comprising contacting the subject with a prodrug of a SARM, in an amount effective to effect a change in an androgen-dependent condition.

In another embodiment, the present invention provides a method of hormone replacement therapy, comprising contacting the subject with a prodrug of a SARM, in an amount effective to effect a change in an androgen-dependent condition.

In another embodiment, the present invention provides a method of treating a subject having a hormone-related condition, comprising contacting the subject with a prodrug of a SARM, in an amount effective to effect a change in a hormone-related condition.

In another embodiment, the present invention provides a method of treating a subject suffering from a prostate cancer in a subject, comprising contacting the subject with a prodrug of a SARM, in an amount effective to treat a prostate cancer in the subject.

In another embodiment, the present invention provides a method of reducing an incidence of a prostate cancer in a subject, comprising contacting the subject with a prodrug of a SARM, in an amount effective to reduce an incidence of a prostate cancer in the subject.

In another embodiment, the present invention provides a method of delaying a progression of a prostate cancer in a subject having prostate cancer, comprising contacting the subject with a prodrug of a SARM, in an amount effective to delay the progression of a prostate cancer in the subject.

In another embodiment, the present invention provides a method of reducing an incidence of a recurrence of a prostate cancer in a subject, comprising contacting the subject with a prodrug of a SARM, in an amount effective to reduce the incidence of a recurrence of a prostate cancer in the subject.

In another embodiment, the present invention provides a method of treating a dry eye condition in a subject, comprising contacting the subject with a prodrug of a SARM, in an amount effective to treat the dry eye condition in the subject.

In another embodiment, the present invention provides a method of reducing an incidence of a dry eye condition in a subject, comprising contacting the subject with a prodrug of a SARM, in an amount effective to reducing an incidence of the dry eye condition in the subject.

In another embodiment, the present invention provides a method of binding an androgen receptor (AR), comprising contacting the AR with a prodrug of a SARM.

In another embodiment, the present invention provides a prodrug of a selective androgen receptor modulator (SARM) compound, wherein the prodrug is represented by a structure of formula II-B:

II-B

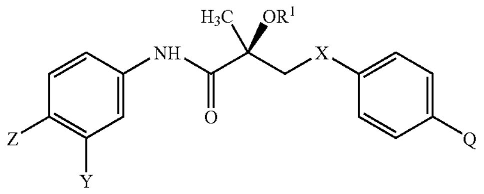

wherein

X is a bond, O, CH2, NH, Se, PR, NO or NR;

Z is NO2, CN, COOH, COR, NHCOR or CONHR;

Y is CF3, F, I, Br, Cl, CN, CR3 or SnR3;

Q is alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OR, COR, OCOR, OSO2R, SO2R, SR, SCN, NCS, OCN, or NCO; or Q together with the benzene ring to which it is attached is a fused ring system represented by structure A, B or C:

A

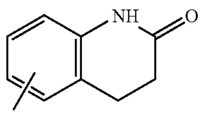

B

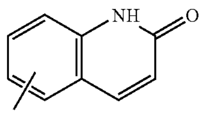

C

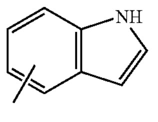

R is alkyl, haloalkyl, dihaloalkyl, trihaloalkyl, CH2F, CHF2, CF3,

CF2CF3, aryl, phenyl, F, I, Br, Cl, alkenyl or OH;

wherein R1 is as defined below, and wherein the SARM compound is bound to any suitable atom of R1.

In another embodiment, the present invention provides a prodrug of a selective androgen receptor modulator (SARM) compound, wherein the prodrug is represented by a structure of formula V-B:

V-B

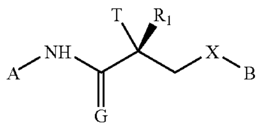

wherein

X is a bond, O, CH2, NH, Se, PR, NO or NR;

G is O or S;

T is CH3, CH2F, CHF2, CF3, CH2CH3, or CF2CF3;

R is alkyl, haloalkyl, dihaloalkyl, trihaloalkyl, CH2F, CHF2, CF3, CF2CF3, aryl, phenyl, F, I, Br, Cl, alkenyl or OH;

A is a ring selected from:

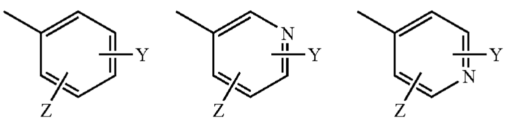

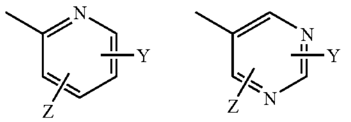

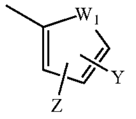

and

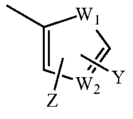

B is a ring selected from:

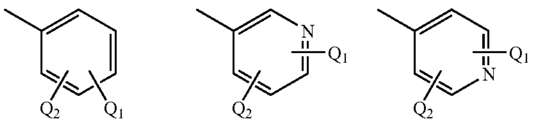

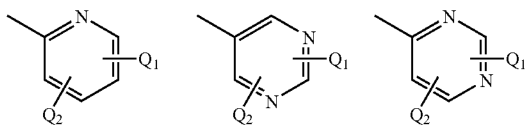

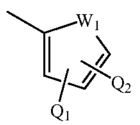

and

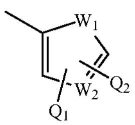

wherein A and B are not simultaneously a benzene ring;

Z is NO2, CN, COOH, COR, NHCOR or CONHR;

Y is CF3, F, I, Br, Cl, CN, CR3 or SnR3;

Q1 and Q2 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO,

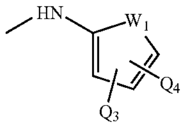

or

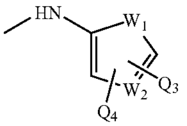

Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

W1 is O, NH, NR, NO or S;

W2 is N or NO, wherein R1 is as defined below, and wherein the SARM compound is bound to any suitable atom of R1.

In another embodiment, the present invention provides a prodrug of a SARM compound, wherein the prodrug is represented by a structure of formula VII-B:

VII-B

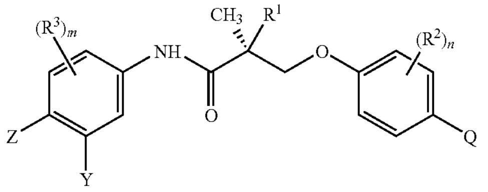

wherein

R2 is F, Cl, Br, I, CH3, CF3, OH, CN, NO2, NHCOCH3, NHCOCF3, NHCOR, alkyl, arylalkyl, OR, NH2, NHR, NR2, SR;

R3 is F, Cl, Br, I, CN, NO2, COR, COOH, CONHR, CF3, or SnR3, or R3 together with the benzene ring to which it is attached forms a fused ring system represented by one of the structures:

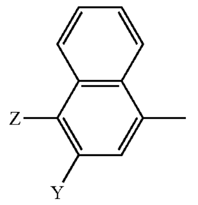

or

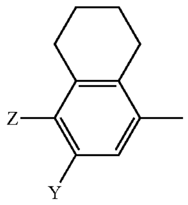

R is alkyl, haloalkyl, dihaloalkyl, trihaloalkyl, CH2F, CHF2, CF3, CF2CF3, aryl, phenyl, F, I, Br, Cl, alkenyl or OH;

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OH, OR, COR, OCOR, OSO2R, SO2R, or SR; or Q together with the benzene ring to which it is attached is a fused ring system represented by structure A, B or C:

A

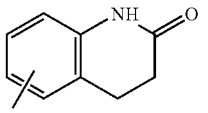

B

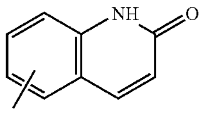

C

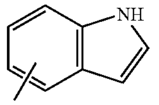

n is an integer of 1-4;

m is an integer of 1-3;

and R1 is as defined below, and wherein the SARM compound is bound to any suitable atom of R1.

In another embodiment, the present invention provides a prodrug of a SARM compound, wherein the prodrug is represented by a structure of formula VIII-B:

VIII-B

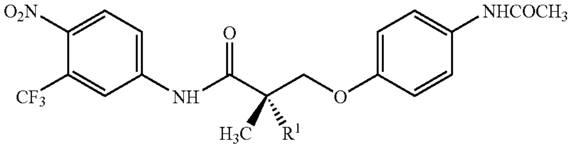

wherein R1 is as defined below, and wherein the SARM compound is bound to any suitable atom of R1.

In another embodiment, the present invention provides a prodrug of a SARM compound, wherein the prodrug is represented by a structure of formula XI-B:

XI-B

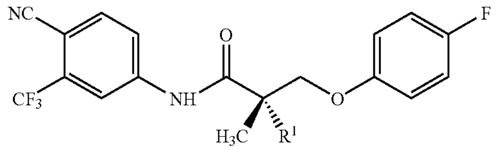

wherein R1 is as defined below, and wherein the SARM compound is bound to any suitable atom of R1.

In another embodiment, the present invention provides a prodrug of a selective androgen receptor modulator (SARM) compound, wherein the prodrug is represented by a structure of formula XIII-B:

XIII-B

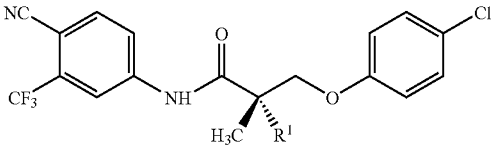

wherein R1 is as defined below; and wherein the SARM compound is bound to any suitable atom of R1.

In another embodiment, the present invention provides a prodrug of a selective androgen receptor modulator (SARM) compound, wherein the prodrug is represented by a structure of formula IV-B:

IV-B

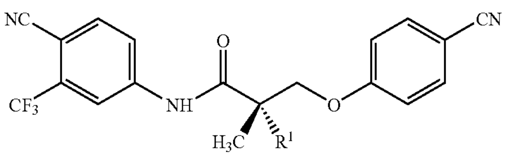

wherein R1 is one of the structures depicted below, and wherein the SARM compound is bound to any suitable atom of R1.

The SARM modification in the above structures designated by a number "B" (referred to as R1) is one of the structures:

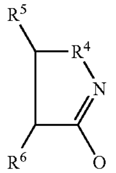
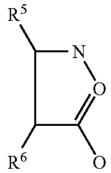
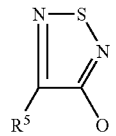
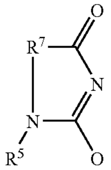
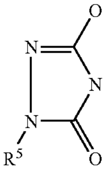
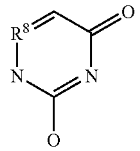
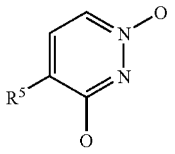
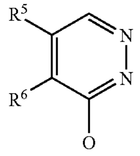
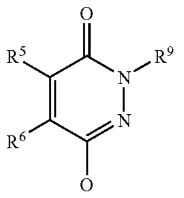
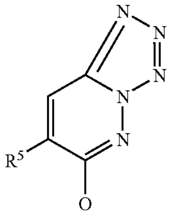
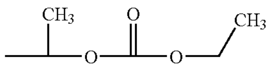
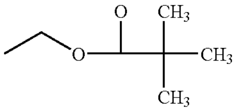
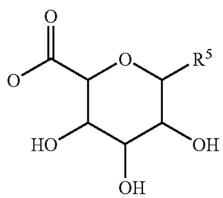

-continued

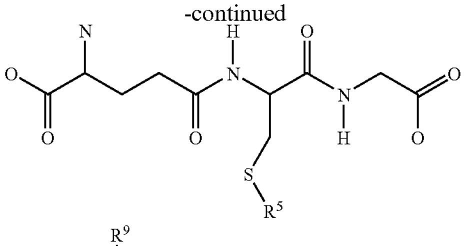

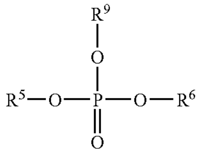
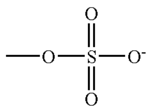

and wherein

R7 is O or C2;

R8 is N or CH;

R5, R6, and R9 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond to the SARM compound at the indicated location,

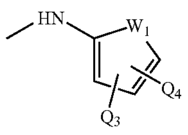
or
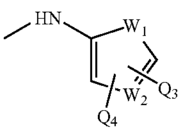

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO.

In another embodiment, the present invention provides a prodrug of a SARM compound, wherein the prodrug is represented by a structure of formula II:

II

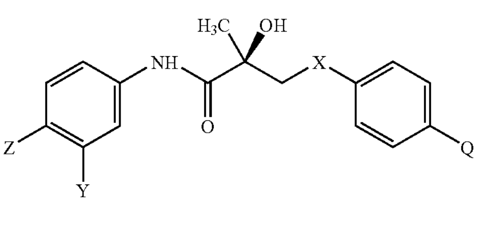

wherein X is a bond, O, CH2, NH, Se, PR, NO or NR;

Z is NO2, CN, COOH, COR, NHCOR, or CONHR;

Y is CF3, F, I, Br, Cl, CN, CR3 or SnR3;

R is alkyl, haloalkyl, dihaloalkyl, trihaloalkyl, CH2F, CHF2, CF3, CF2CF3, aryl, phenyl, F, I, Br, Cl, alkenyl or OH;

and either:

(a) Q is one of the structures:

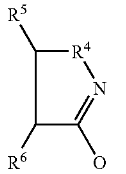
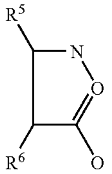
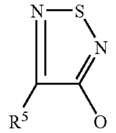
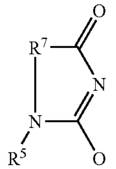
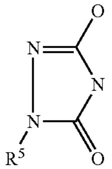
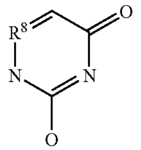
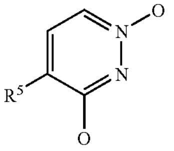
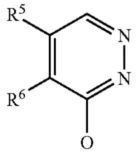
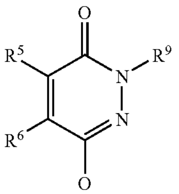
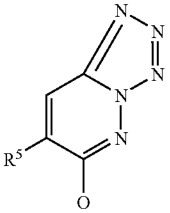
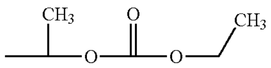
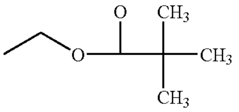
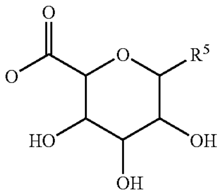
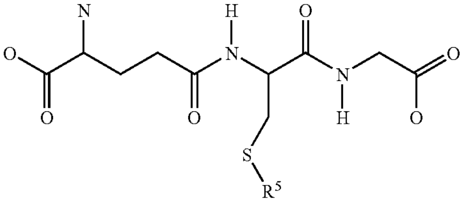
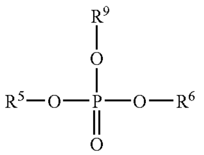
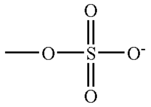

wherein

R7 is O or CH2;

R8 is N or CH;

R5, R6, and R9 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond to the SARM compound at the indicated location,

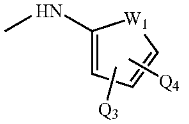

or

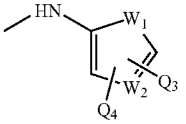

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

wherein the SARM compound is bound to any suitable atom of Q; or (b) Q, together with a B ring to which it is attached, is a fused ring system represented by one of the structures:

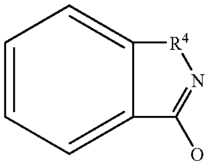
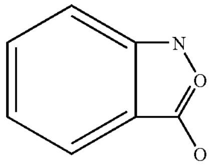
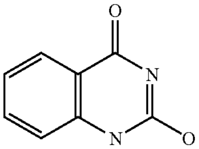
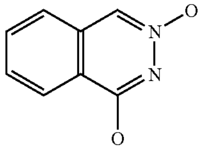
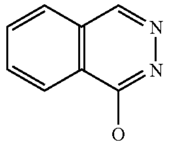
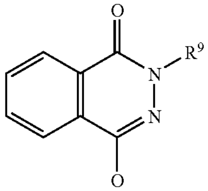

In another embodiment, the present invention provides a prodrug of a SARM compound, wherein the prodrug is represented by a structure of formula L:

L

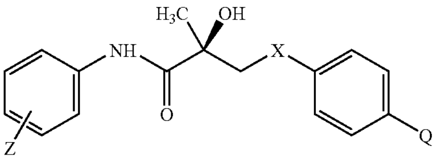

wherein X is a bond, O, CH2, NH, Se, PR, NO or NR;

Q is alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OR, COR, OCOR, OSO2R, SO2R, SR, SCN, NCS, OCN, or NCO; or Q together with the benzene ring to which it is attached is a fused ring system represented by structure A, B or C:

A

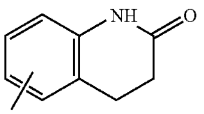

B

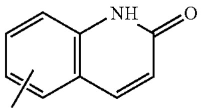

C

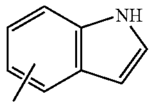

R is alkyl, haloalkyl, dihaloalkyl, trihaloalkyl, CH2F, CHF2, CF3, CF2CF3, aryl, phenyl, F, I, Br, Cl, alkenyl or OH;

and either:

(a) Z is one of the structures:

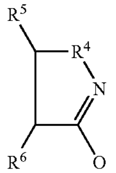

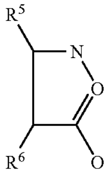

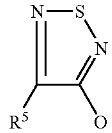

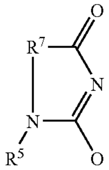

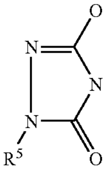

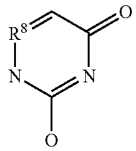

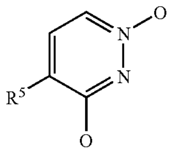

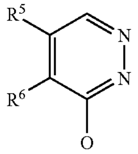

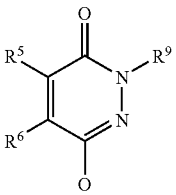

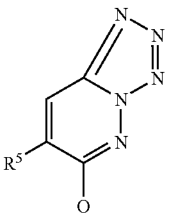

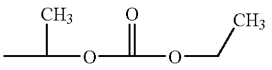

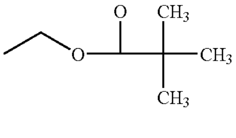

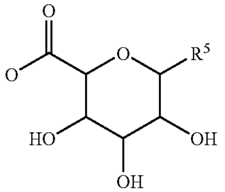

-continued

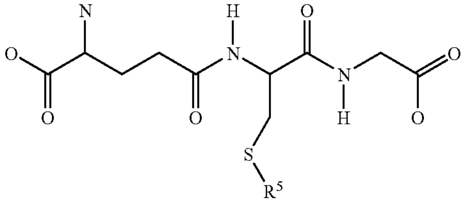

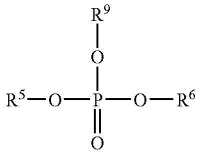

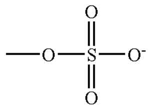

wherein

R7 is O or CH2;

R8 is N or CH;

R5, R6, and R9 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond to the SARM compound at the indicated location,

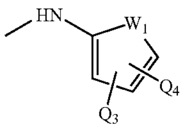

or

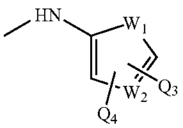

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

wherein the SARM compound is bound to any suitable atom of Z; or (b) Z, together with a B ring to which it is attached, is a fused ring system represented by one of the structures:

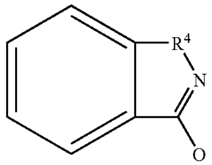

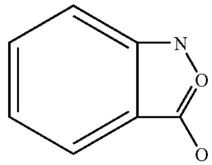

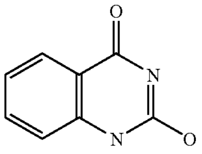

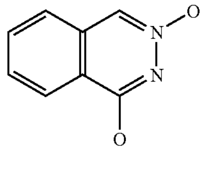

-continued

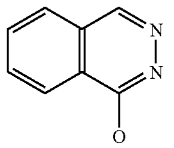

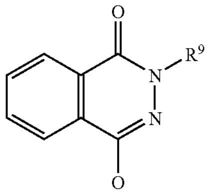

In another embodiment, the present invention provides a prodrug of a SARM compound, wherein the prodrug is represented by a structure of formula LI:

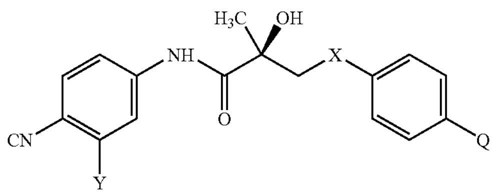

LI wherein

X is a bond, O, CH2, NH, Se, PR, NO or NR;

Z is NO2, CN, COOH, COR, NHCOR, or CONHR;

Y is CF3, F, I, Br, Cl, CN, CR3 or SnR3;

R is alkyl, haloalkyl, dihaloalkyl, trihaloalkyl, CH2F, CHF2, CF3, CF2CF3, aryl, phenyl, F, I, Br, Cl, alkenyl or OH;

and either:

(a) Q is one of the structures:

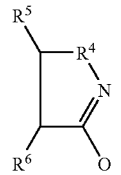

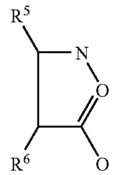

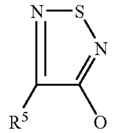

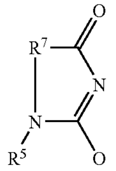

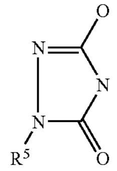

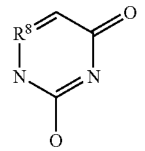

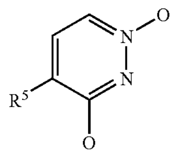

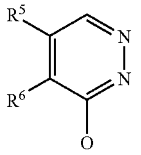

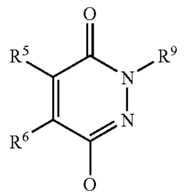

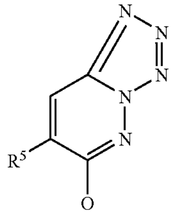

-continued

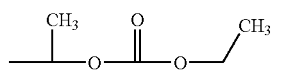

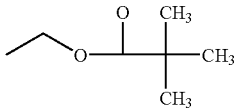

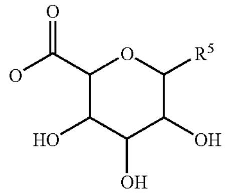

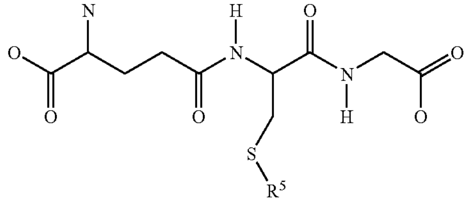

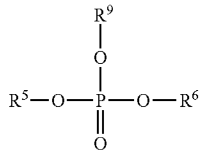

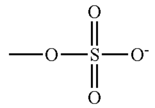

wherein

R7 is O or CH2;

R8 is N or CH;

R5, R6, and R9 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond to the SARM compound at the indicated location,

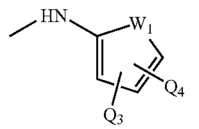

or

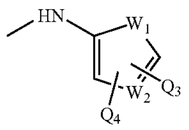

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

wherein the SARM compound is bound to any suitable atom of Q; or (b) Q, together with a B ring to which it is attached, is a fused ring system represented by one of the structures:

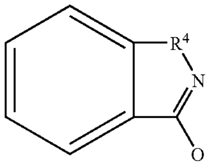
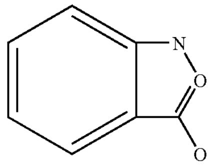
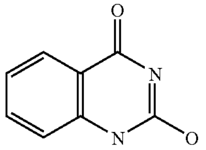
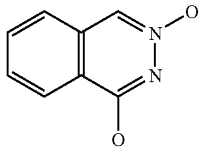
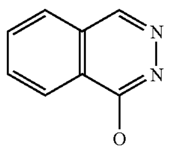
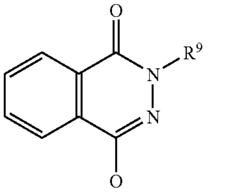

In another embodiment, the present invention provides a prodrug of a SARM compound, wherein the prodrug is represented by a structure of formula LII:

LII

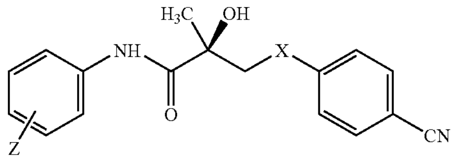

wherein

X is a bond, O, CH2, NH, Se, PR, NO or NR;

R is alkyl, haloalkyl, dihaloalkyl, trihaloalkyl, CH2F, CHF2, CF3, CF2CF3, aryl, phenyl, F, I, Br, Cl, alkenyl or OH;

and either:

(a) Z is one of the structures:

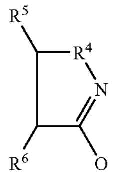
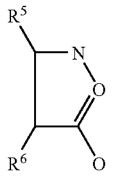
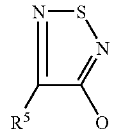
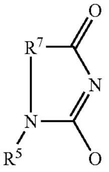
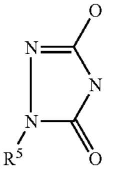
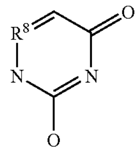
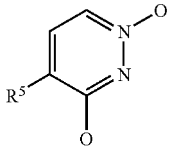
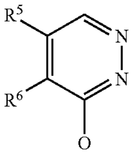

-continued

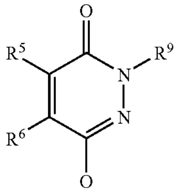
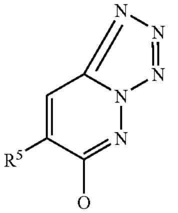
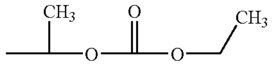
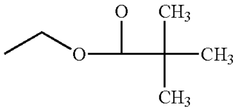
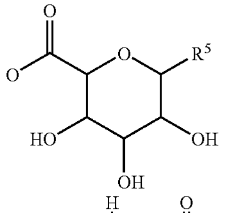
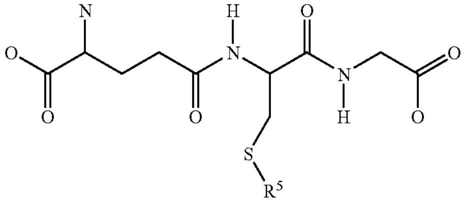
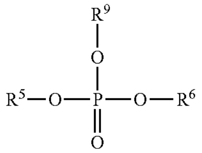
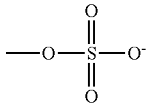

wherein

R7 is O or CH2;

R8 is N or CH;

R5, R6, and R9 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond to the SARM compound at the indicated location,

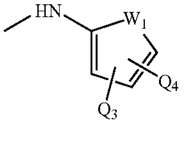
or
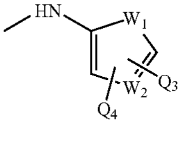

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

wherein the SARM compound is bound to any suitable atom of Z; or (b) Z, together with a B ring to which it is attached, is a fused ring system represented by one of the structures:

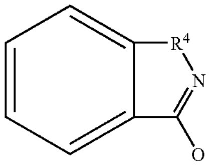

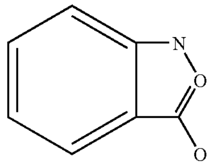

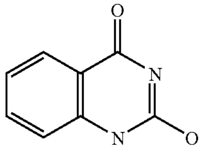

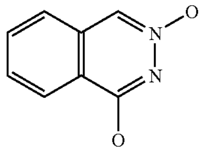

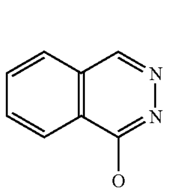

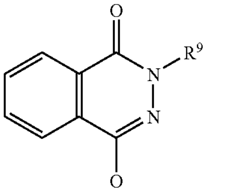

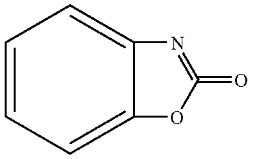

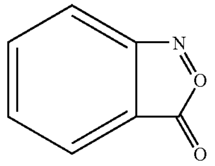

BRIEF DESCRIPTION OF THE FIGURES

The present invention will be understood and appreciated more fully from the following detailed description, taken in conjunction with the appended figures which depict.

DETAILED DESCRIPTION OF THE INVENTION

Figure 1:
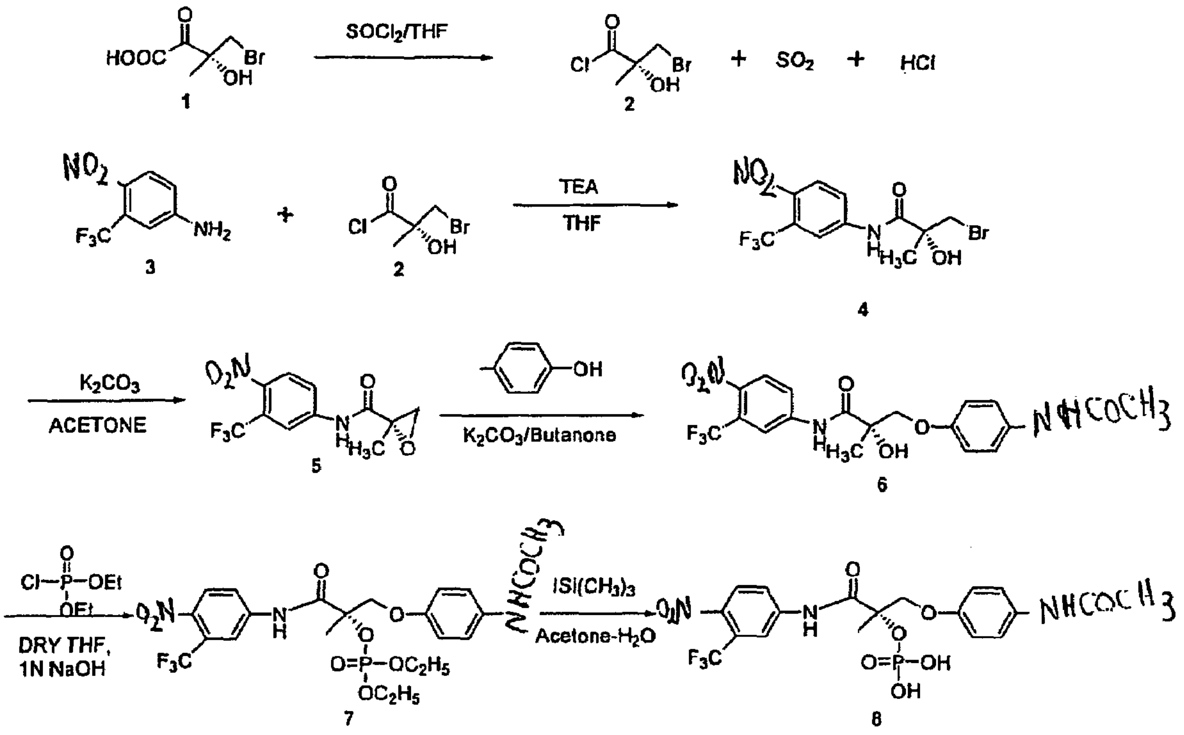
FIG. 1: Synthesis scheme of Compound VIII.

In one embodiment, this invention provides prodrugs of selective androgen receptor modulators (SARM) compounds. Several of the parent SARM compounds have been found to have an androgenic and anabolic activity of a nonsteroidal ligand for the androgen receptor. The parent SARM compounds, either alone or as a composition, are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; c) preventing and/or treating dry eye conditions; f) oral androgen replacement therapy; g) decreasing the incidence of, halting or causing a regression of prostate cancer; and/or h) inducing apoptosis in a cancer cell.

Thus, in one embodiment, the present invention provides a prodrug of a SARM compound, wherein the SARM compound is represented by a structure of formula I:

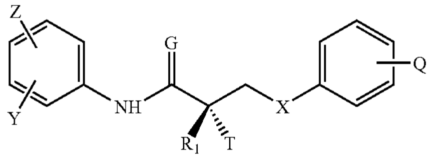

I wherein

G is O or S;

X is O;

T is OH, OR, —$NHCOCH_3$, or NHCOR;

Z is $NO_2$, CN, COOH, COR, NHCOR or CONHR;

Y is $CF_3$, F, I, Br, Cl, CN, $CR_3$ or $SnR_3$;

Q is acetamido or trifluoroacetamido;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH; and $R_1$ is $CH_3$, $CH_2F$, $CHF_2$, $CF_3$, $CH_2CH_3$, or $CF_2CF_3$.

In one embodiment, G in compound I is O. In another embodiment, T in compound I is OH. In another embodiment, $R_1$ in compound I is $CH_3$. In another embodiment, Z in compound I is $NO_2$. In another embodiment, Z in compound I is CN. In another embodiment, Y in compound I is $CF_3$. In another embodiment, Q in compound I is $NHCOCH_3$. In another embodiment, Q in compound I is in the para position. In another embodiment, Z in compound I is in the para position. In another embodiment, Y in compound I is in the meta position. In another embodiment, G in compound I is O, T is OH, $R_1$ is $CH_3$, Z is $NO_2$, Y is $CF_3$, and Q is $NHCOCH_3$. In another embodiment, G in compound I is O, T is OH, Z is CN, Y is $CF_3$, and Q is $NHCOCH_3$.

In another embodiment, the present invention provides a prodrug of a SARM compound, wherein the SARM compound is represented by a structure of formula II:

II

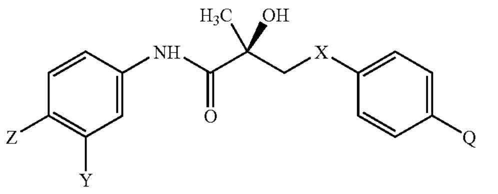

wherein

X is O;

Z is $NO_2$, CN, COOH, COR, NHCOR or CONHR;

Y is $CF_3$, F, I, Br, Cl, CN, $CR_3$ or $SnR_3$;

Q is acetamido or trifluoroacetamido;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH; and $R_1$ is $CH_3$, $CH_2F$, $CHF_2$, $CF_3$, $CH_2CH_3$, or $CF_2CF_3$.

In one embodiment, Z in compound II is $NO_2$. In another embodiment, Z in compound II is CN. In another embodiment, Y in compound II is $CF_3$. In another embodiment, Q in compound II is $NHCOCH_3$. In another embodiment, Z in compound II is $NO_2$, Y is $CF_3$, and Q is $NHCOCH_3$. In another embodiment, Z in compound II is CN, Y is $CF_3$, and Q is $NHCOCH_3$.

In one embodiment, the SARM prodrug of the present invention has in-vivo androgenic and anabolic activity of a nonsteroidal ligand for the androgen receptor. In another embodiment, the SARM prodrug of the present invention is an androgen receptor agonist.

In one embodiment, a prodrug of the present invention has a modification that increases an aqueous solubility of the prodrug relative to the parent SARM compound. In another embodiment, a prodrug of the present invention has a modification that decreases an aqueous solubility of the prodrug relative to the parent SARM compound. In another embodiment, a prodrug of the present invention has a modification that increases a bioavailability of the prodrug relative to the SARM. In one embodiment, the bioavailability is an oral bioavailability. In another embodiment, a prodrug of the present invention has a modification that decreases a toxicity of the prodrug relative to the SARM.

In another embodiment, the present invention provides a prodrug of a SARM compound, wherein the SARM compound is represented by a structure of formula V:

V

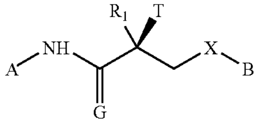

wherein

X is a bond, O, CH2, NH, Se, PR, NO or NR;

G is O or S;

R1 is CH3, CH2F, CHF2, CF3, CH2CH3, or CF2CF3;

T is OH, OR, —NHCOCH3, or NHCOR;

R is alkyl, haloalkyl, dihaloalkyl, trihaloalkyl, CH2F, CHF2, CF3, CF2CF3, aryl, phenyl, F, I, Br, Cl, alkenyl or OH;

A is a ring selected from:

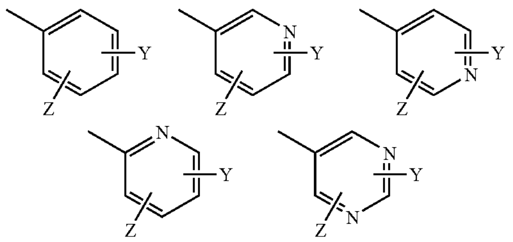

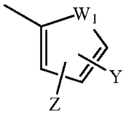

and

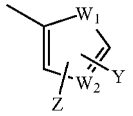

B is a ring selected from:

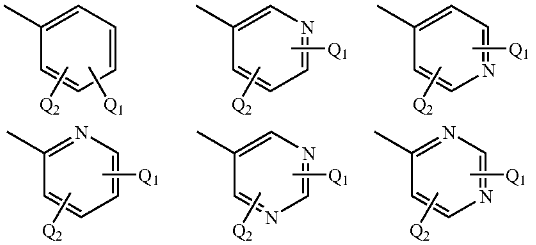

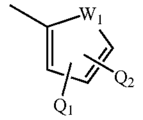

and

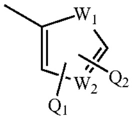

wherein A and B are not simultaneously a benzene ring;

Z is NO2, CN, COOH, COR, NHCOR or CONHR;

Y is CF3, F, I, Br, Cl, CN, CR3 or SnR3;

Q1 and Q2 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO,

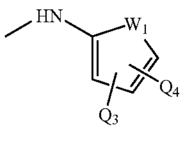

or

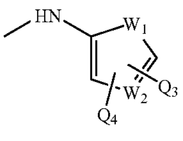

Q3 and Q4 are independently of each other a hydrogen, alkyl, F, I, Br, Cl, CF3, CN, CR3, SnR3, NR2, NHCOCH3, NHCOCF3, NHCOR, s NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

W1 is O, NH, NR, NO or S; and

W2 is N or NO.

In another embodiment, the present invention provides a prodrug of a SARM compound, wherein the SARM compound is represented by a structure of formula VI:

VI

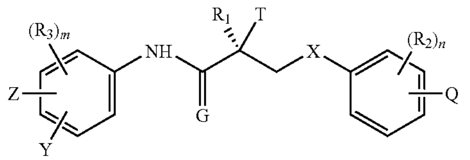

wherein

X is a bond, O, CH2, NH, Se, PR, NO or NR;

G is O or S;

T is OH, OR, —NHCOCH3, or NHCOR;

R is alkyl, haloalkyl, dihaloalkyl, trihaloalkyl, CH2F, CHF2, CF3, CF2CF3, aryl, phenyl, F, I, Br, Cl, alkenyl or OH;

R1 is CH3, CH2F, CHF2, CF3, CH2CH3, or CF2CF3;

R2 is F, Cl, Br, I, CH3, CF3, OH, CN, NO2, NHCOCH3, NHCOCF3, NHCOR, alkyl, arylalkyl, OR, NH2, NHR, NR2, SR, SCN, NCS, OCN, or NCO;

R3 is F, Cl, Br, I, CN, NO2, COR, COOH, CONHR, CF3, SnR3, or R3 together with the benzene ring to which it is attached forms a fused ring system represented by one of the structures:

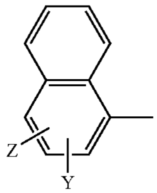

or

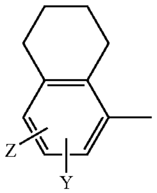

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OH, OR, COR, OCOR, OSO2R, SO2R, or SR; or Q together with the benzene ring to which it is attached is a fused ring system represented by structure A, B or C:

A

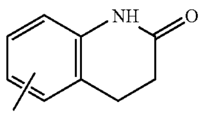

B

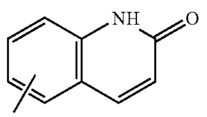

C

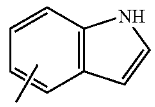

n is an integer of 1-4; and m is an integer of 1-3.

In another embodiment, the present invention provides a prodrug of a SARM compound, wherein the SARM compound is represented by a structure of formula VII:

VII

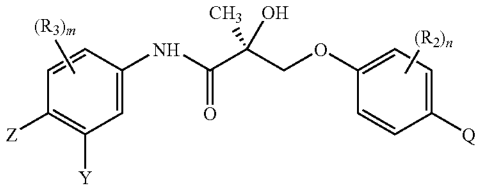

wherein

R2 is F, Cl, Br, I, CH3, CF3, OH, CN, NO2, NHCOCH3, NHCOCF3, NHCOR, alkyl, arylalkyl, OR, NH2, NHR, NR2, SR;

R3 is F, Cl, Br, I, CN, NO2, COR, COOH, CONHR, CF3, or SnR3, or R3 together with the benzene ring to which it is attached forms a fused ring system represented by one of the structures:

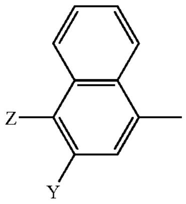

or

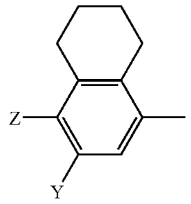

R is alkyl, haloalkyl, dihaloalkyl, trihaloalkyl, CH2F, CHF2, CF3, CF2CF3, aryl, phenyl, F, I, Br, Cl, alkenyl or OH;

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OH, OR, COR, OCOR, OSO2R, SO2R, or SR; or Q together with the benzene ring to which it is attached is a fused ring system represented by structure A, B or C:

A

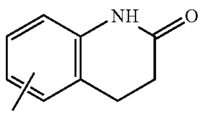

B

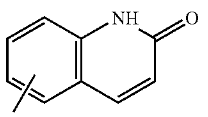

C

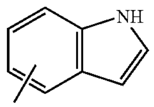

n is an integer of 1-4; and m is an integer of 1-3

In another embodiment, the present invention provides a prodrug of a SARM compound, wherein the SARM compound is represented by a structure of formula VIII:

VIII

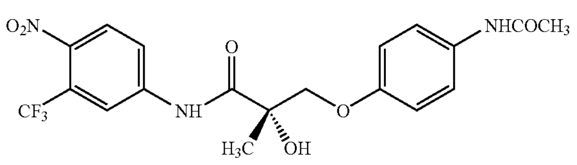

In another embodiment, the present invention provides a prodrug of a SARM compound, wherein the SARM compound is represented by a structure of formula XI:

XI

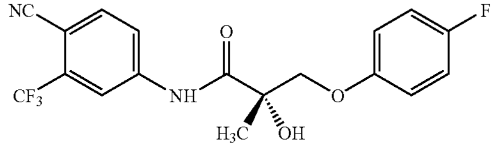

In another embodiment, the present invention provides a prodrug of a SARM compound, wherein the SARM compound is represented by a structure of formula XIII:

XIII

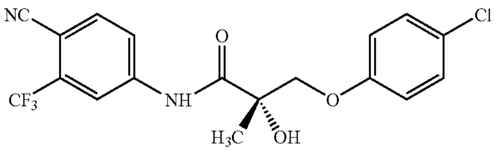

In another embodiment, the present invention provides a prodrug of a SARM compound, wherein the SARM compound is represented by a structure of formula XIV:

XIV

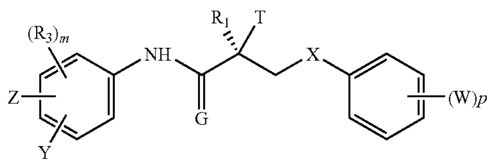

wherein

X is a bond, O, CH2, NH, Se, PR, NO or NR;

G is O or S;

T is OH, OR, —NHCOCH3, or NHCOR;

R is alkyl, haloalkyl, dihaloalkyl, trihaloalkyl, CH2F, CHF2, CF3, CF2CF3, aryl, phenyl, F, I, Br, Cl, alkenyl or OH;

R1 is CH3, CH2F, CHF2, CF3, CH2CH3, or CF2CF3;

W is F, Cl, Br, I, CH3, CF3, OH, CN, NO2, NHCOCH3, NHCOCF3, NHCOR, alkyl, arylalkyl, OR, NH2, NHR, NR2, SR, SCN, NCS, OCN, or NCO;

R3 is F, Cl, Br, I, CN, NO2, COR, COOH, CONHR, CF3, SnR3, or R3 together with the benzene ring to which it is attached forms a fused ring system represented by one of the structures:

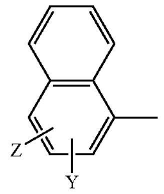

or

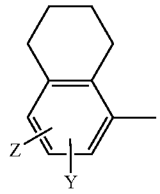

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OH, OR, COR, OCOR, OSO2R, SO2R, or SR; or Q together with the benzene ring to which it is attached is a fused ring system represented by structure A, B or C:

A

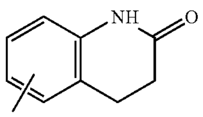

B

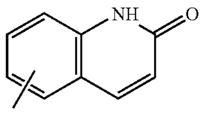

C

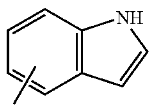

n is an integer of 1-4;

m is an integer of 1-3; and p is an integer between 2-5, inclusive.

In another embodiment, the present invention provides a prodrug of a SARM compound, wherein the SARM compound is represented by a structure of formula XVII:

XVII

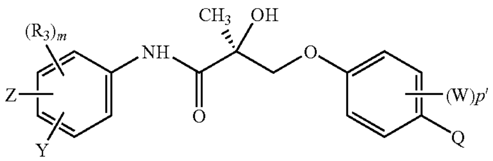

wherein

W is F, Cl, Br, I, CH3, CF3, OH, CN, NO2, NHCOCH3, NHCOCF3, NHCOR, alkyl, arylalkyl, OR, NH2, NHR, NR2, SR;

R3 is F, Cl, Br, I, CN, NO2, COR, COOH, CONHR, CF3, or SnR3, or R3 together with the benzene ring to which it is attached forms a fused ring system represented by one of the structures:

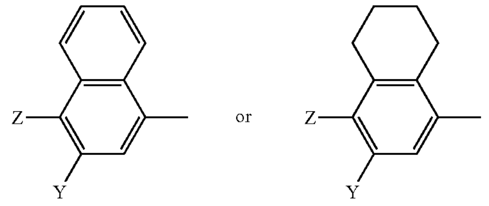

R is alkyl, haloalkyl, dihaloalkyl, trihaloalkyl, CH2F, CHF2, CF3, CF2CF3, aryl, phenyl, F, I, Br, Cl, alkenyl or OH;

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OH, OR, COR, OCOR, OSO2R, SO2R, or SR; or Q together with the benzene ring to which it is attached is a fused ring system represented by structure A, B or C:

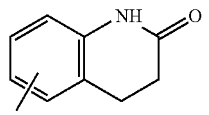

A

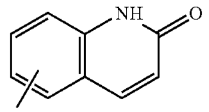

B

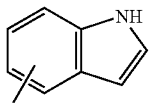

C n is an integer of 1-4;

m is an integer of 1-3; and p' is an integer between 1-4, inclusive.

In another embodiment, the present invention provides a prodrug of a SARM compound, wherein the SARM compound is represented by a structure of formula IV:

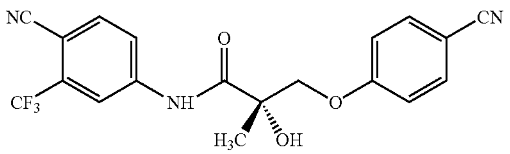

IV

In another embodiment, the parent SARM compound is a compound of one of the above formulas wherein Z is $NO_2$. In another embodiment, the parent SARM compound is a compound of one of the above formulas wherein Z is CN. In another embodiment, the parent SARM compound is a compound of one of the above formulas wherein Z is COOH. In another embodiment, the parent SARM compound is a compound of one of the above formulas wherein Z is COR. In another embodiment, the parent SARM compound is a compound of one of the above formulas wherein Z is NHCOR. In another embodiment, the parent SARM compound is a compound of one of the above formulas wherein Z is CONHR.

In another embodiment, the parent SARM compound is a compound of one of the above formulas wherein Y is $CF_3$. In another embodiment, the parent SARM compound is a compound of one of the above formulas wherein Y is F. In another embodiment, the parent SARM compound is a compound of one of the above formulas wherein Y is I. In another embodiment, the parent SARM compound is a compound of one of the above formulas wherein Y is Br. In another embodiment, the parent SARM compound is a compound of one of the above formulas wherein Y is Cl. In another embodiment, the parent SARM compound is a compound of one of the above formulas wherein Y is CN. In another embodiment, the parent SARM compound is a compound of one of the above formulas wherein Y is $CR_3$. In another embodiment, the parent SARM compound is a compound of one of the above formulas wherein Y is $SnR_3$.

In another embodiment, the parent SARM compound is a compound of one of the above formulas wherein Q is $NHCOCH_3$. In another embodiment, the parent SARM compound is a compound of one of the above formulas wherein Q is F. In another embodiment, the parent SARM compound is a compound of one of the above formulas wherein Q is alkyl. In another embodiment, the parent SARM compound is a compound of one of the above formulas wherein Q is I. In another embodiment, the patent SARM compound is a compound of one of the above formulas wherein Q is Br. In another embodiment, the parent SARM compound is a compound of one of the above formulas wherein Q is Cl. In another embodiment, the parent SARM compound is a compound of one of the above formulas wherein Q is $CF_3$. In another embodiment, the parent SARM compound is a compound of one of the above formulas wherein Q is CN. In another embodiment, the parent SARM compound is a compound of one of the above formulas wherein Q is $CR_3$. In another embodiment, the parent SARM compound is a compound of one of the above formulas wherein Q is $SnR_3$. In another embodiment, the parent SARM compound is a compound of one of the above formulas wherein Q is $NR_2$. In another embodiment, the parent SARM compound is a compound of one of the above formulas wherein Q is $NHCOCF_3$. In another embodiment, the parent SARM compound is a compound of one of the above formulas wherein Q is NHCOR. In another embodiment, the parent SARM compound is a compound of one of the above formulas wherein Q is NHCONHR. In another embodiment, the parent SARM compound is a compound of one of the above formulas wherein Q is NHCOOR. In another embodiment, the parent SARM compound is a compound of one of the above formulas wherein Q is OCONHR. In another embodiment, the parent SARM compound is a compound of one of the above formulas wherein Q is CONHR. In another embodiment, the parent SARM compound is a compound of one of the above formulas wherein Q is $NHCSCH_3$. In another embodiment, the parent SARM compound is a compound of one of the above formulas wherein Q is $NHCSCF_3$. In another embodiment, the parent SARM compound is a compound of one of the above formulas wherein Q is NHCSR. In another embodiment, the parent SARM compound is a compound of one of the above formulas wherein Q is $NHSO_2CH_3$, In another embodiment, the parent SARM compound is a compound of one of the above formulas wherein Q is $NHSO_2R$. In another embodiment, the parent SARM compound is a compound of one of the above formulas wherein Q is OR. In another embodiment, the parent SARM compound is a compound of one of the above formulas wherein Q is COR. In another embodiment, the parent SARM compound is a compound of one of the above formulas wherein Q is OCOR. In another embodiment, the parent SARM compound is a compound of one of the above formulas wherein Q is $OSO_2R$. In another embodiment, the parent SARM compound is a compound of one of the above formulas wherein Q is $SO_2R$. In another embodiment, the parent SARM compound is a compound of one of the above formulas wherein Q is SR. In another embodiment, the parent SARM compound is a compound of one of the above formulas wherein Q is SCN. In another embodiment, the parent SARM compound is a compound of one of the above formulas wherein Q is NCS. In another embodiment, the parent SARM compound is a compound of one of the above formulas wherein Q is OCN. In another embodiment, the parent SARM compound is a compound of one of the above formulas wherein Q is NCO.

In another embodiment, the parent SARM compound is a compound of one of the above formulas wherein R is alkyl In another embodiment, the parent SARM compound is a compound of one of the above formulas wherein R is haloalkyl. In another embodiment, the parent SARM compound is a compound of one of the above formulas wherein R is dihaloalkyl. In another embodiment, the parent SARM compound is a compound of one of the above formulas wherein R is trihaloalkyl. In another embodiment, the parent SARM compound is a compound of one of the above formulas wherein R is $CH_2F$. In another embodiment, the parent SARM compound is a compound of one of the above formulas wherein R is $CHF_2$. In another embodiment, the parent SARM compound is a compound of one of the above formulas wherein R is $CF_3$. In another embodiment, the parent SARM compound is a compound of one of the above formulas wherein R is $CF_2CF_3$. In another embodiment, the parent SARM compound is a compound of one of the above formulas wherein R is aryl. In another embodiment, the parent SARM compound is a compound of one of the above formulas wherein R is phenyl. In another embodiment, the parent SARM compound is a compound of one of the above formulas wherein R is F. In another embodiment, the parent SARM compound is a compound of one of the above formulas wherein R is I. In another embodiment, the parent SARM compound is a compound of one of the above formulas wherein R is Br. In another embodiment, the parent SARM compound is a compound of one of the above formulas wherein R is Cl. In another embodiment, the parent SARM compound is a compound of one of the above formulas wherein R is alkenyl. In another embodiment, the parent SARM compound is a compound of one of the above formulas wherein R is OH.

In another embodiment, the parent SARM compound is a compound of one of the above formulas wherein $R^1$ is $CH_3$. In another embodiment, the parent SARM compound is a compound of one of the above formulas wherein $R^1$ is $CH_2F$. In another embodiment, the parent SARM compound is a compound of one of the above formulas wherein $R^1$ is $CHF_2$. In another embodiment, the parent SARM compound is a compound of one of the above formulas wherein $R^1$ is $CF_3$. In another embodiment, the parent SARM compound is a compound of one of the above formulas wherein $R^1$ is $CH_2CH_3$. In another embodiment, the parent SARM compound is a compound of one of the above formulas wherein $R^1$ is $CF_2CF_3$.

Each substituent of each of X, Y, Z, G, T, Q, R and $R^1$, for each of the above formulas, represents a separate embodiment of the present invention. Further, each position enumerated above of each of the above substituents represents a separate embodiment of the present invention. Further, each number enumerated above of each of the above integers represents a separate embodiment of the present invention.

In one embodiment, a prodrug of the present invention has a modification that alters an aqueous solubility of the prodrug relative to the parent SARM compound. In another embodiment, a prodrug of the present invention has a modification that increases a bioavailability of the prodrug relative to the SARM. In one embodiment, the bioavailability is an oral bioavailability.

In another embodiment, the present invention provides a composition comprising a prodrug of a SARM of the present invention; and a suitable carrier or diluent. In another embodiment, the present invention provides a pharmaceutical composition comprising an effective amount of a prodrug of a SARM of the present invention; and a pharmaceutically acceptable carrier or diluent.

In another embodiment, the present invention provides a method of suppressing spermatogenesis in a subject, comprising contacting the subject with a prodrug of a SARM, in an amount effective to suppress sperm production.

In another embodiment, the present invention provides a method of contraception of a male subject, comprising contacting the male subject with a prodrug of a SARM, in an amount effective to suppress sperm production in the male subject, thereby effecting contraception of a subject.

In another embodiment, the present invention provides a method of hormone therapy of a subject, comprising contacting the subject with a prodrug of a SARM, in an amount effective to effect a change in an androgen-dependent condition.

In another embodiment, the present invention provides a method of hormone replacement therapy, comprising contacting the subject with a prodrug of a SARM, in an amount effective to effect a change in an androgen-dependent condition.

In another embodiment, the present invention provides a method of treating a subject having a hormone-related condition, comprising contacting the subject with a prodrug of a SARM, in an amount effective to effect a change in a hormone-related condition.

In another embodiment, the present invention provides a method of treating a subject having a prostate cancer, comprising contacting the subject with a prodrug of a SARM, in an amount effective to treat a prostate cancer in the subject.

In another embodiment, the present invention provides a method of reducing an incidence of a prostate cancer in a subject, comprising contacting the subject with a prodrug of a SARM, in an amount effective to reduce an incidence of a prostate cancer in the subject.

In another embodiment, the present invention provides a method of delaying a progression of a prostate cancer in a subject having prostate cancer, comprising contacting the subject with a prodrug of a SARM, in an amount effective to delay the progression of a prostate cancer in the subject.

In another embodiment, the present invention provides a method of reducing an incidence of a recurrence of a prostate cancer in a subject, comprising contacting the subject with a prodrug of a SARM, in an amount effective to reduce the incidence of a recurrence of a prostate cancer in the subject.

Furthermore, stimulation of the Androgen Receptor stimulates the production of tears, and thus the SARM prodrugs of the present invention may be used to treat dry eye conditions. Thus, the present invention provides a method of treating a dry eye condition in a subject, comprising contacting the subject with a prodrug of a SARM, in an amount effective to treat the dry eye condition in the subject.

In another embodiment, the present invention provides a method of reducing an incidence of a dry eye condition in a subject, comprising contacting the subject with a prodrug of a SARM, in an amount effective to reducing an incidence of the dry eye condition in the subject.

In another embodiment, the present invention provides a method of binding an androgen receptor (AR), comprising contacting the AR with a prodrug of a SARM.

In another embodiment, the present invention provides a prodrug of a selective androgen receptor modulator (SARM) compound, wherein the prodrug is represented by a structure of formula II-B:

II-B

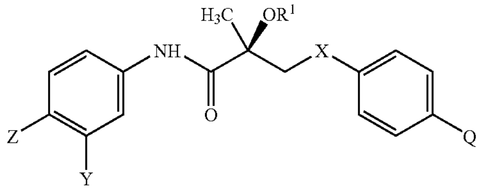

wherein

X is a bond, O, CH2, NH, Se, PR, NO or NR;

Z is NO2, CN, COOH, COR, NHCOR or CONHR;

Y is CF3, F, I, Br, Cl, CN, CR3 or SnR3;

Q is alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OR, COR, OCOR, OSO2R, SO2R, SR, SCN, NCS, OCN, or NCO; or Q together with the benzene ring to which it is attached is a fused ring system represented by structure A, B or C:

A

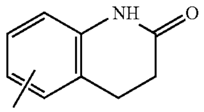

B

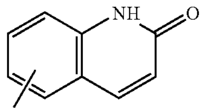

C

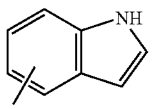

R is alkyl, haloalkyl, dihaloalkyl, trihaloalkyl, CH2F, CHF2, CF3, CF2CF3, aryl, phenyl, F, I, Br, Cl, alkenyl or OH;

wherein R1 is as defined below, and wherein the SARM compound is bound to any suitable atom of R1.

In another embodiment, the present invention provides a prodrug of a selective androgen receptor modulator (SARM) compound, wherein the prodrug is represented by a structure of formula V-B:

V-B

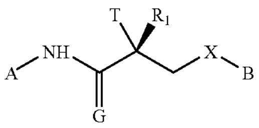

wherein

X is a bond, O, CH2, NH, Se, PR, NO or NR;

G is O or S;

T is CH3, CH2F, CHF2, CF3, CH2CH3, or CF2CF3;

R is alkyl, haloalkyl, dihaloalkyl, trihaloalkyl, CH2F, CHF2, CF3, CF2CF3, aryl, phenyl, F, I, Br, Cl, alkenyl or OH;

A is a ring selected from:

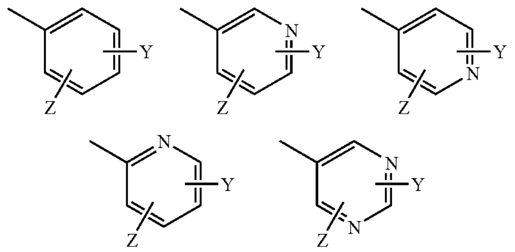

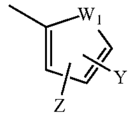

and

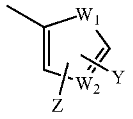

B is a ring selected from:

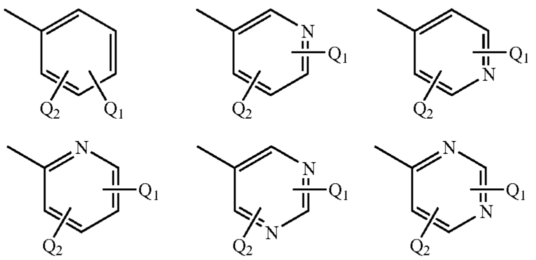

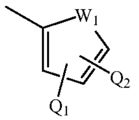

and

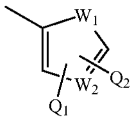

wherein A and B are not simultaneously a benzene ring;

Z is NO2, CN, COOH, COR, NHCOR or CONHR;

Y is CF3, F, I, Br, Cl, CN, CR3 or SnR3;

Q1 and Q2 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO,

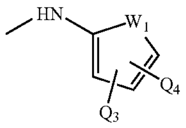

or

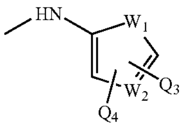

Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

W1 is O, NH, NR, NO or S;

W2 is N or NO, wherein R1 is as defined below, and wherein the SARM compound is bound to any suitable atom of R1.

In another embodiment, the present invention provides a prodrug of a SARM compound, wherein the prodrug is represented by a structure of formula VII-B:

VII-B

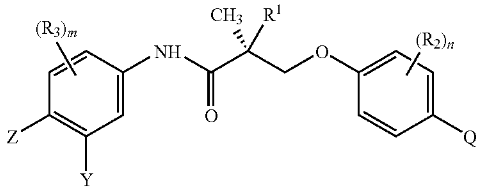

wherein

R2 is F, Cl, Br, I, CH3, CF3, OH, CN, NO2, NHCOCH3, NHCOCF3, NHCOR, alkyl, arylalkyl, OR, NH2, NHR, NR2, SR;

R3 is F, Cl, Br, I, CN, NO2, COR, COOH, CONHR, CF3, or SnR3, or R3 together with the benzene ring to which it is attached forms a fused ring system represented by one of the structures:

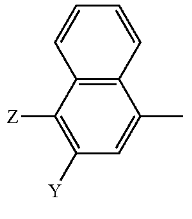

or

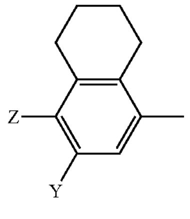

R is alkyl, haloalkyl, dihaloalkyl, trihaloalkyl, CH2F, CHF2, CF3, CF2CF3, aryl, phenyl, F, I, Br, Cl, alkenyl or OH;

Z is NO2, CN, COR, COOH, or CONHR;

Y is CF3, F, Br, Cl, I, CN, or SnR3;

Q is H, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OH, OR, COR, OCOR, OSO2R, SO2R, or SR; or Q together with the benzene ring to which it is attached is a fused ring system represented by structure A, B or C:

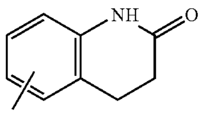

A

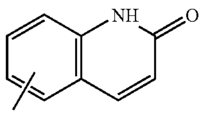

B

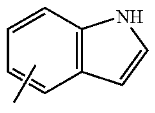

C n is an integer of 1-4;

m is an integer of 1-3;

and R1 is as defined below, and wherein the SARM compound is bound to any suitable atom of R1.

In another embodiment, the present invention provides a prodrug of a SARM compound, wherein the prodrug is represented by a structure of formula VIII-B:

VIII-B

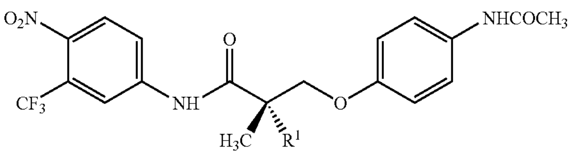

wherein R1 is as defined below, and wherein the SARM compound is bound to any suitable atom of R1.

In another embodiment, the present invention provides a prodrug of a SARM compound, wherein the prodrug is represented by a structure of formula XI-B:

XI-B

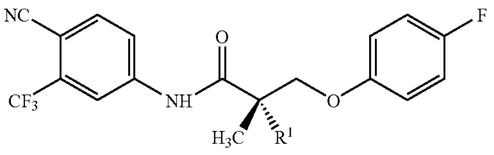

wherein R1 is as defined below, and wherein the SARM compound is bound to any suitable atom of R1.

In another embodiment, the present invention provides a prodrug of a selective androgen receptor modulator (SARM) compound, wherein the prodrug is represented by a structure of formula XIII-B:

XIII-B

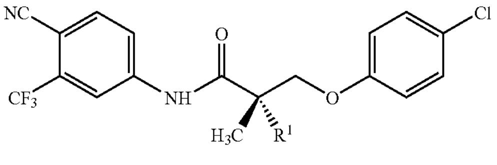

wherein R1 is as defined below; and wherein the SARM compound is bound to any suitable atom of R1.

In another embodiment, the present invention provides a prodrug of a selective androgen receptor modulator (SARM) compound, wherein the prodrug is represented by a structure of formula IV-B:

IV-B

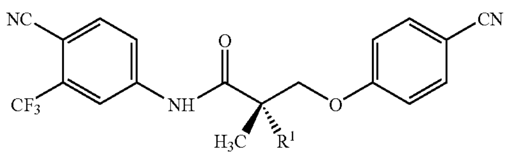

wherein R1 is one of the structures depicted below, and wherein the SARM compound is bound to any suitable atom of R1.

The SARM modification in the above structures designated by a number "B" (referred to as R1) is one of the structures:

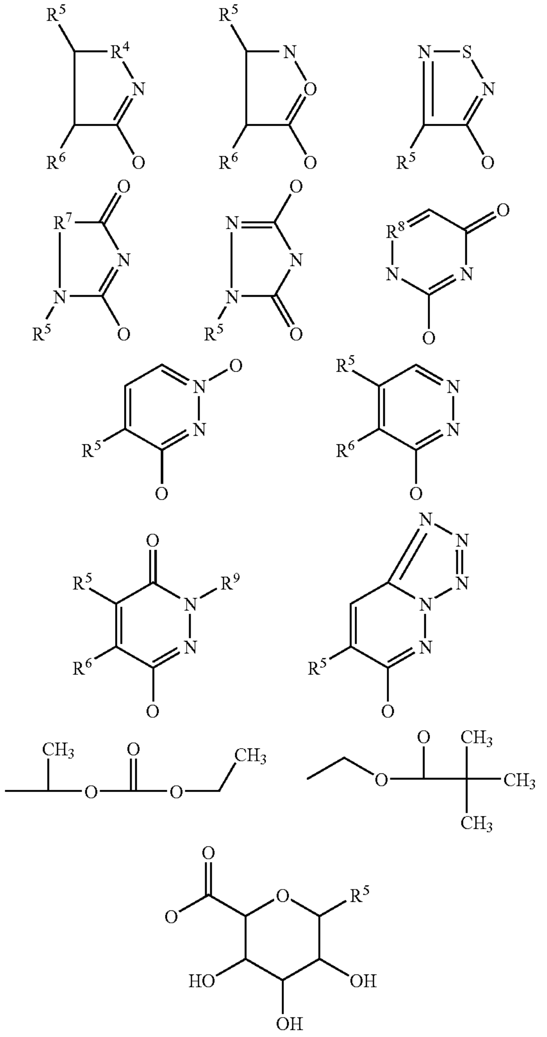

-continued

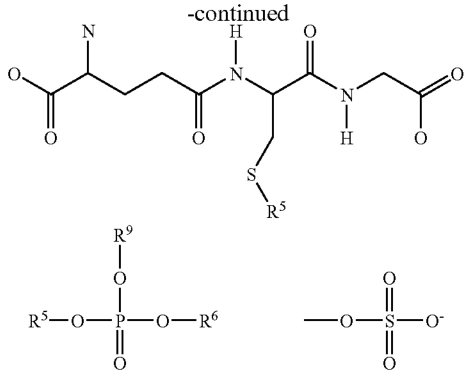

and wherein

R7 is O or CH2;

R8 is N or CH;

R5, R6, and R9 are independently of each other a hydrogen, alkyl, F, I, Br, Cl, CF3, CN, CR3, SnR3, NR2, NHCOCH3, NHCOOF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond, O-linkage, or N-linkage to the SARM compound at the indicated location,

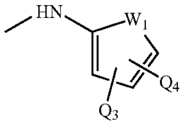

or

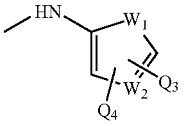

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO.

In another embodiment, the present invention provides a prodrug of a SARM compound, wherein the prodrug is represented by a structure of formula II:

II

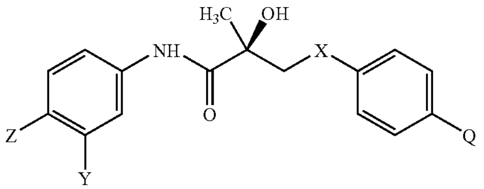

wherein

X is a bond, O, CH2, NH, Se, PR, NO or NR;

Z is NO2, CN, COOH, COR, NHCOR, or CONHR;

Y is CF3, F, I, Br, Cl, CN, CR3 or SnR3;

R is alkyl, haloalkyl, dihaloalkyl, trihaloalkyl, CH2F, CHF2, CF3, CF2CF3, aryl, phenyl, F, I, Br, Cl, alkenyl or OH;

and either:

(a) Q is one of the structures:

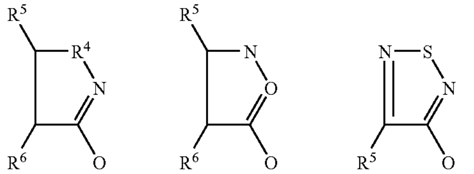

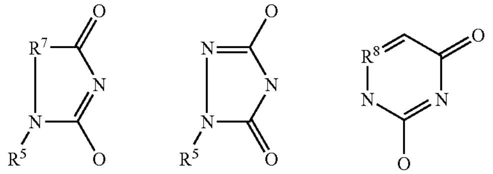

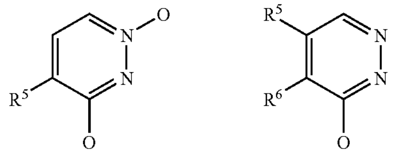

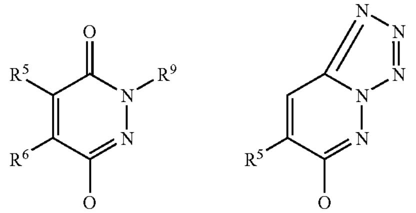

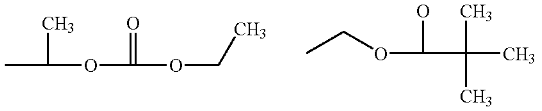

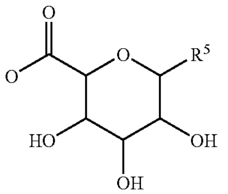

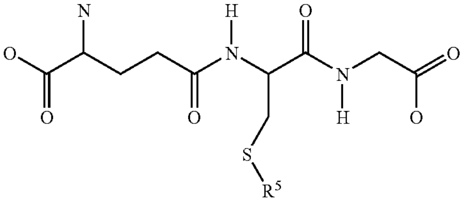

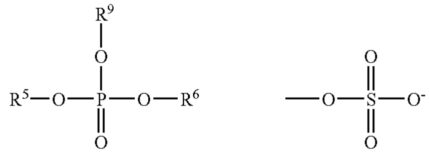

wherein

R7 is O or CH2;

R8 is N or CH;

R5, R6, and R9 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond, O-linkage, or N-linkage to the SARM compound at the indicated location,

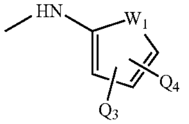

or

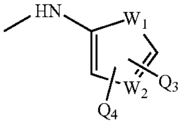

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

wherein the SARM compound is bound to any suitable atom of Q; or (b) Q, together with a B ring to which it is attached, is a fused ring system represented by one of the structures:

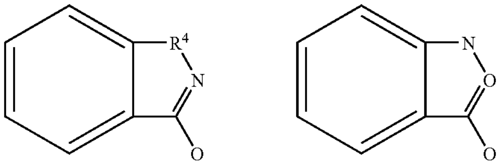

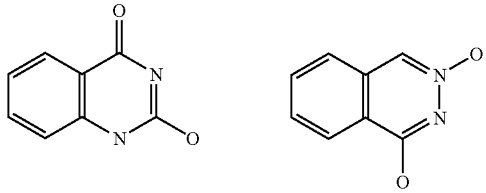

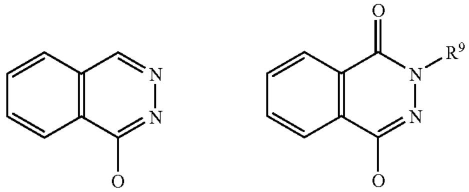

In another embodiment, the present invention provides a prodrug of a SARM compound, wherein the prodrug is represented by a structure of formula L:

L

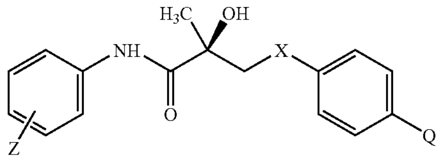

wherein X is a bond, O, CH2, NH, Se, PR, NO or NR;

Q is alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR, NHSO2CH3, NHSO2R, OR, COR, OCOR, OSO2R, SO2R, SR, SCN, NCS, OCN, or NCO; or Q together with the benzene ring to which it is attached is a fused ring system represented by structure A, B or C:

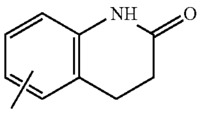
A

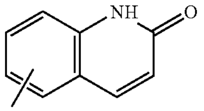
B

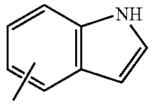
C

R is alkyl, haloalkyl, dihaloalkyl, trihaloalkyl, CH2F, CHF2, CF3, CF2CF3, aryl, phenyl, F, I, Br, Cl, alkenyl or OH; and either:

(a) Z is one of the structures:

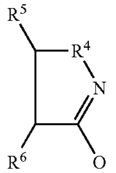
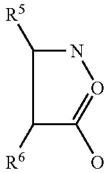
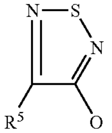
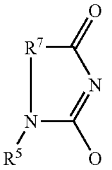
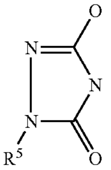
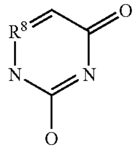
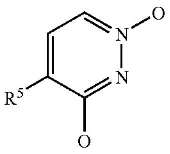
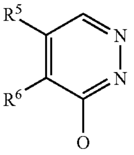
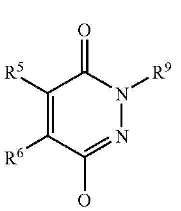
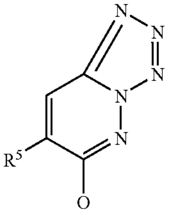
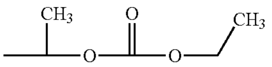
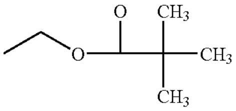
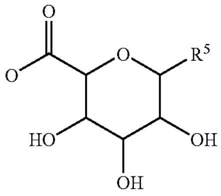

-continued

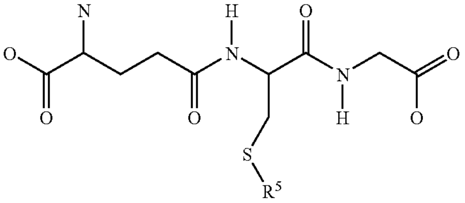

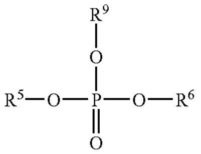
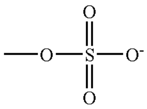

wherein

R7 is O or CH2;

R8 is N or CH;

R5, R6, and R9 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond, O-linkage, or N-linkage to the SARM compound at the indicated location,

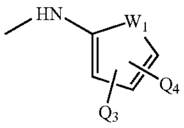
or
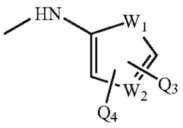

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

wherein the SARM compound is bound to any suitable atom of Z; or (b) Z, together with a B ring to which it is attached, is a fused ring system represented by one of the structures:

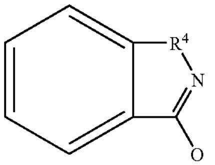
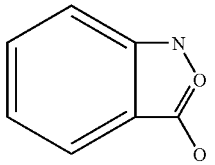
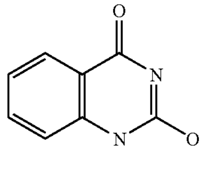
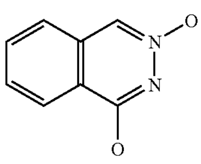

-continued

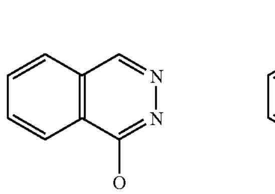

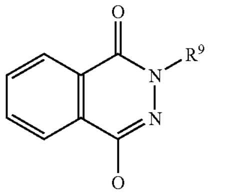

In another embodiment, the present invention provides a prodrug of a SARM compound, wherein the prodrug is represented by a structure of formula LI:

LI

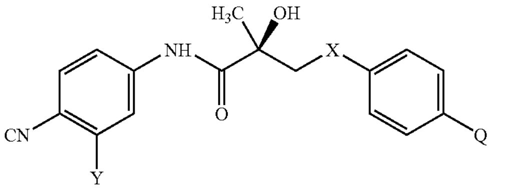

wherein

X is a bond, O, CH2, NH, Se, PR, NO or NR;

Z is NO2, CN, COOH, COR, NHCOR, or CONHR;

Y is CF3, F, I, Br, Cl, CN, CR3 or SnR3;

R is alkyl, haloalkyl, dihaloalkyl, trihaloalkyl, CH2F, CHF2, CF3, CF2CF3, aryl, phenyl, F, I, Br, Cl, alkenyl or OH;

and either:

(a) Q is one of the structures:

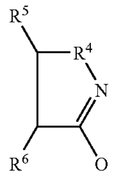

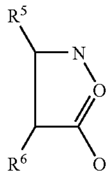

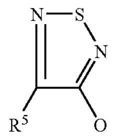

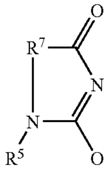

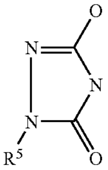

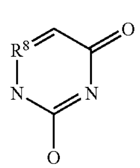

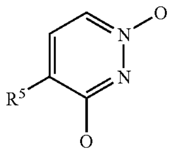

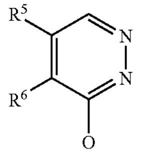

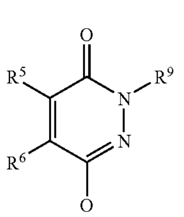

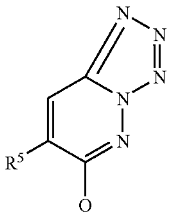

-continued

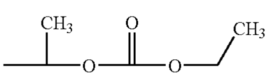

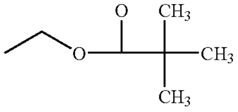

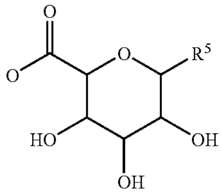

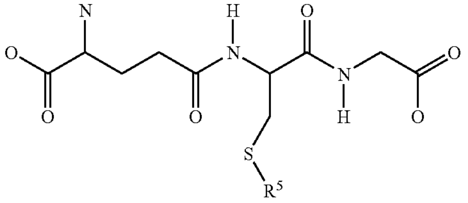

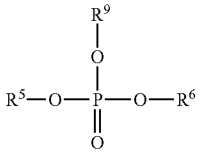

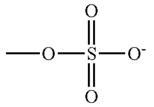

wherein

R7 is O or CH2;

R8 is N or CH;

R5, R6, and R9 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond, O-linkage, or N-linkage to the SARM compound at the indicated location,

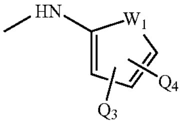

or

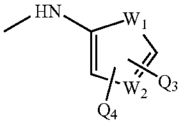

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

wherein the SARM compound is bound to any suitable atom of Q; or (b) Q, together with a B ring to which it is attached, is a fused ring system represented by one of the structures:

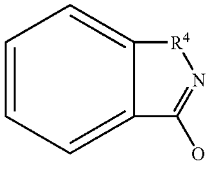
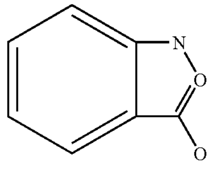
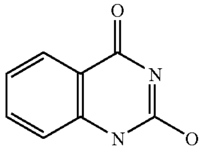
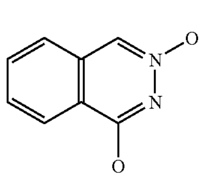
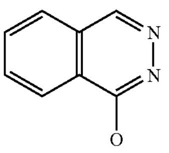
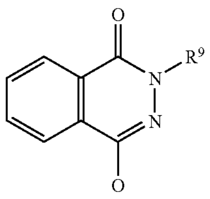

In another embodiment, the present invention provides a prodrug of a SARM compound, wherein the prodrug is represented by a structure of formula LII:

LII

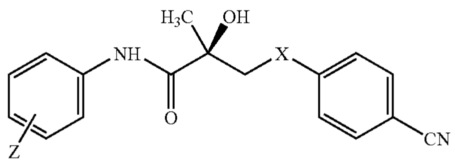

wherein

X is a bond, O, CH2, NH, Se, PR, NO or NR;

R is alkyl, haloalkyl, dihaloalkyl, trihaloalkyl, CH2F, CHF2, CF3, CF2CF3, aryl, phenyl, F, I, Br, Cl, alkenyl or OH; and either:

(a) Z is one of the structures:

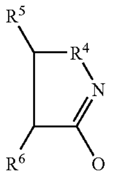
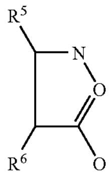
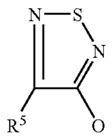
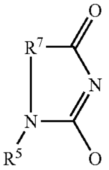
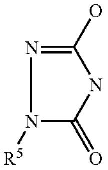
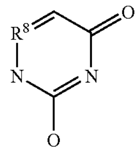
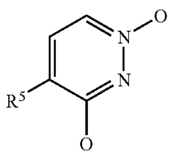
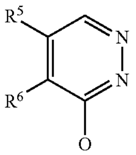

-continued

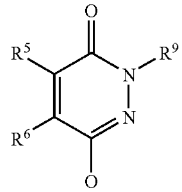
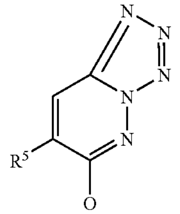
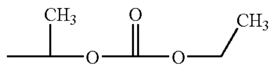
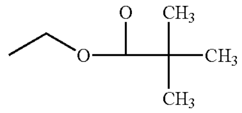
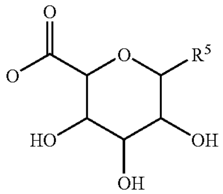
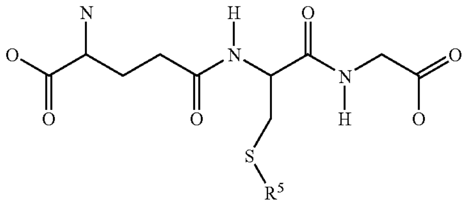
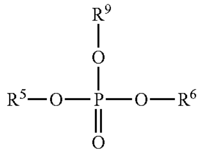
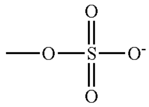

wherein

R7 is O or CH2;

R8 is N or CH;

R5, R6, and R9 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R, SR, SCN, NCS, OCN, NCO, a bond, O-linkage, or N-linkage to the SARM compound at the indicated location,

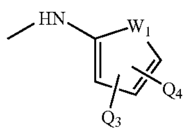

or

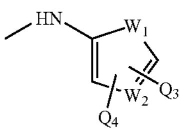

wherein Q3 and Q4 are independently of each other a hydrogen, alkyl, F, I, Br, Cl, CF3, CN, CR3, SnR3, NR2, NHCOCH3, NHCOCF3, NHCOR, NHCONHR, NHCOOR, OCONHR, CONHR, NHCSCH3, NHCSCF3, NHCSR NHSO2CH3, NHSO2R, OR, COR, OCOR, OSO2R, SO2R or SR, SCN, NCS, OCN, or NCO;

wherein the SARM compound is bound to any suitable atom of Z; or (b) Z, together with a B ring to which it is attached, is a fused ring system represented by one of the structures:

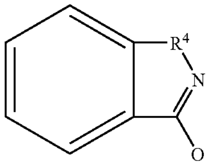
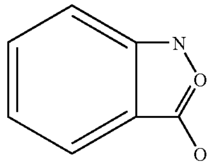
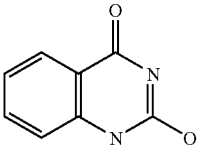
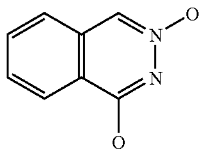
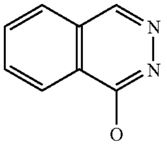
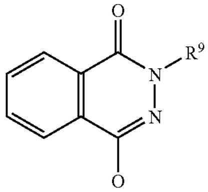

In another embodiment, the present invention provides a synthetic intermediate represented by a structure of formula LIII:

LIII

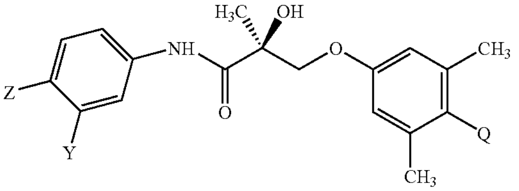

wherein:

Z is $NO_2$, CN, COR, COOH, or CONHR;

Y is $CF_3$, F, Br, Cl, I, CN, or $SnR_3$; and

Q is H, alkyl, F, I, Br, $C_1$, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, or SR; or Q together with the benzene ring to which it is attached is a fused ring system represented by structure A, B or C:

A

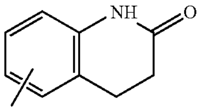

B

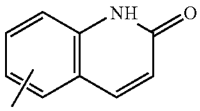

-continued

C

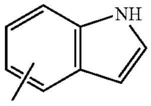

In another embodiment, the present invention provides a prodrug derived from the above synthetic intermediate, wherein a methyl group is replaced by one of the structures:

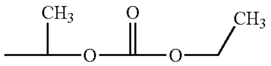
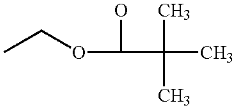
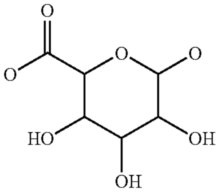
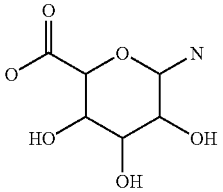
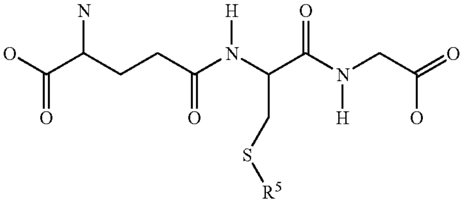
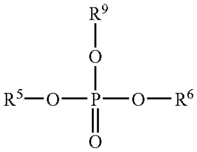

In another embodiment, the present invention provides a synthetic intermediate represented by a structure of formula LIV:

LIV

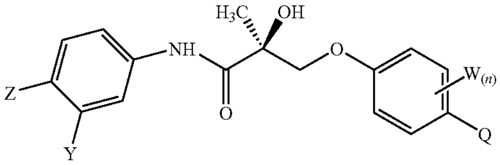

wherein:

Z is $NO_2$, CN, COR, COOH, or CONHR;

Y is $CF_3$, F, Br, Cl, I, CN, or $SnR_3$;

Q is H, alkyl, F, I, Br, Cl, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, or SR; or Q together with the benzene ring to which it is attached is a fused ring system represented by structure A, B or C:

A

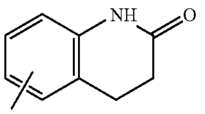

B

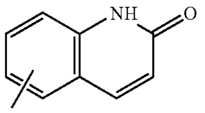

C

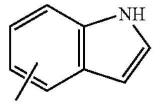

W is $NO_2$ or OH; and

N is 1, 2, 3, or 4.

In another embodiment, the present invention provides a prodrug derived from the above synthetic intermediate, wherein W is replaced by one of the structures:

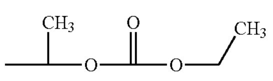

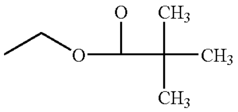

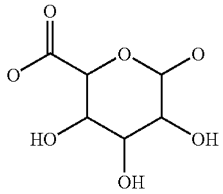

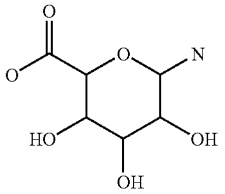

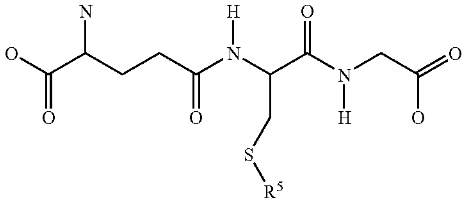

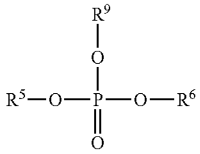

In another embodiment, the present invention provides a synthetic intermediate represented by a structure of formula LV:

LV

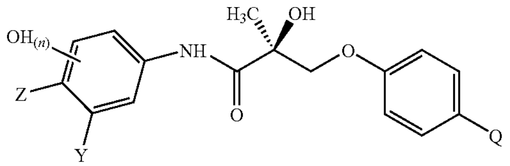

wherein:

Z is $NO_2$, CN, COR, COOH, or CONHR;

Y is $CF_3F$, Br, Cl, I, CN, or $SnR_3$;

Q is H, alkyl, F, I, Br, Cl, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, or SR; or Q together with the benzene ring to which it is attached is a fused ring system represented by structure A, B or C:

A

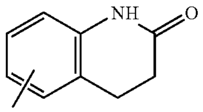

B

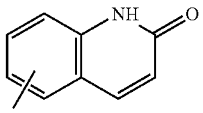

C

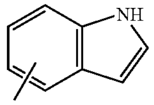

and N is 1, 2, 3, and 4.

In another embodiment, the present invention provides a prodrug derived from the above synthetic intermediate, wherein an OH group is replaced by one of the structures:

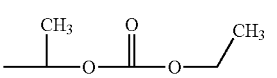

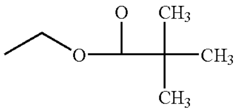

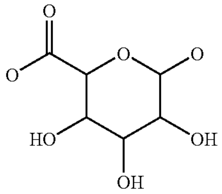

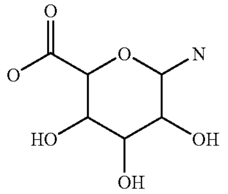

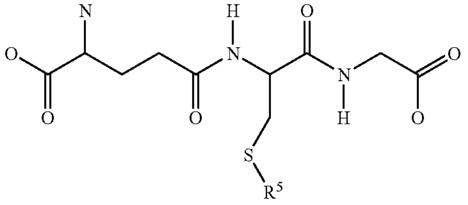

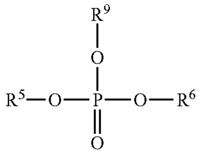

In another embodiment, the SARM prodrug is a compound of one of the above formulas wherein Z is $NO_2$. In another embodiment, the SARM prodrug is a compound of one of the above formulas wherein Z is CN. In another embodiment, the SARM prodrug is a compound of one of the above formulas wherein Z is COOH. In another embodiment, the SARM prodrug is a compound of one of the above formulas wherein Z is COR. In another embodiment, the SARM prodrug is a compound of one of the above formulas wherein Z is NHCOR. In another embodiment, the SARM prodrug is a compound of one of the above formulas wherein Z is CONHR.

In another embodiment, the SARM prodrug is a compound of one of the above formulas wherein Y is $CF_3$. In another embodiment, the SARM prodrug is a compound of one of the above formulas wherein Y is F. In another embodiment, the SARM prodrug is a compound of one of the above formulas wherein Y is I. In another embodiment, the SARM prodrug is a compound of one of the above formulas wherein Y is Br. In another embodiment, the SARM prodrug is a compound of one of the above formulas wherein Y is Cl. In another embodiment, the SARM prodrug is a compound of one of the above formulas wherein Y is CN. In another embodiment, the SARM prodrug is a compound of one of the above formulas wherein Y is $CR_3$. In another embodiment, the SARM prodrug is a compound of one of the above formulas wherein Y is $SnR_3$.

In another embodiment, the SARM prodrug is a compound of one of the above formulas wherein Q is $NHCOCH_3$. In another embodiment, the SARM prodrug is a compound of one of the above formulas wherein Q is F. In another embodiment, the SARM prodrug is a compound of one of the above formulas wherein Q is alkyl. In another embodiment, the SARM prodrug is a compound of one of the above formulas wherein Q is I. In another embodiment, the SARM prodrug is a compound of one of the above formulas wherein Q is Br. In another embodiment, the SARM prodrug is a compound of one of the above formulas wherein Q is Cl. In another embodiment, the SARM prodrug is a compound of one of the above formulas wherein Q is $CF_3$. In another embodiment, the SARM prodrug is a compound of one of the above formulas wherein Q is CN. In another embodiment, the SARM prodrug is a compound of one of the above formulas wherein Q is $CR_3$. In another embodiment, the SARM prodrug is a compound of one of the above formulas wherein Q is $SnR_3$. In another embodiment, the SARM prodrug is a compound of one of the above formulas wherein Q is $NR_2$. In another embodiment, the SARM prodrug is a compound of one of the above formulas wherein Q is $NHCOCF_3$. In another embodiment, the SARM prodrug is a compound of one of the above formulas wherein Q is NHCOR. In another embodiment, the SARM prodrug is a compound of one of the above formulas wherein Q is NHCONHR. In another embodiment, the SARM prodrug is a compound of one of the above formulas wherein Q is NHCOOR. In another embodiment, the SARM prodrug is a compound of one of the above formulas wherein Q is OCONHR. In another embodiment, the SARM prodrug is a compound of one of the above formulas wherein Q is CONHR. In another embodiment, the SARM prodrug is a compound of one of the above formulas wherein Q is $NHCSCH_3$. In another embodiment, the SARM prodrug is a compound of one of the above formulas wherein Q is $NHCSCF_3$. In another embodiment, the SARM prodrug is a compound of one of the above formulas wherein Q is NHCSR. In another embodiment, the SARM prodrug is a compound of one of the above formulas wherein Q is $NHSO_2CH_3$. In another embodiment, the SARM prodrug is a compound of one of the above formulas wherein Q is $NHSO_2R$. In another embodiment, the SARM prodrug is a compound of one of the above formulas wherein Q is OR. In another embodiment, the SARM prodrug is a compound of one of the above formulas wherein Q is COR. In another embodiment, the SARM prodrug is a compound of one of the above formulas wherein Q is OCOR. In another embodiment, the SARM prodrug is a compound of one of the above formulas wherein Q is $OSO_2R$. In another embodiment, the SARM prodrug is a compound of one of the above formulas wherein Q is $SO_2R$. In another embodiment, the SARM prodrug is a compound of one of the above formulas wherein Q is SR. In another embodiment, the SARM prodrug is a compound of one of the above formulas wherein Q is SCN. In another embodiment, the SARM prodrug is a compound of one of the above formulas wherein Q is NCS. In another embodiment, the SARM prodrug is a compound of one of the above formulas wherein Q is OCN. In another embodiment, the SARM prodrug is a compound of one of the above formulas wherein Q is NCO.

In another embodiment, the SARM prodrug is a compound of one of the above formulas wherein R is alkyl In another embodiment, the SARM prodrug is a compound of one of the above formulas wherein R is haloalkyl. In another embodiment, the SARM prodrug is a compound of one of the above formulas wherein R is dihaloalkyl. In another embodiment, the SARM prodrug is a compound of one of the above formulas wherein R is trihaloalkyl. In another embodiment, the SARM prodrug is a compound of one of the above formulas wherein R is $CH_2F$. In another embodiment, the SARM prodrug is a compound of one of the above formulas wherein R is $CHF_2$. In another embodiment, the SARM prodrug is a compound of one of the above formulas wherein R is $CF_3$. In another embodiment, the SARM prodrug is a compound of one of the above formulas wherein R is $CF_2CF_3$. In another embodiment, the SARM prodrug is a compound of one of the above formulas wherein R is aryl. In another embodiment, the SARM prodrug is a compound of one of the above formulas wherein R is phenyl. In another embodiment, the SARM prodrug is a compound of one of the above formulas wherein R is F. In another embodiment, the SARM prodrug is a compound of one of the above formulas wherein R is I. In another embodiment, the SARM prodrug is a compound of one of the above formulas wherein R is Br. In another embodiment, the SARM prodrug is a compound of one of the above formulas wherein R is Cl. In another embodiment, the SARM prodrug is a compound of one of the above formulas wherein R is alkenyl. In another embodiment, the SARM prodrug is a compound of one of the above formulas wherein R is OH.

In another embodiment, the SARM prodrug is a compound of one of the above formulas wherein $R^1$ is $CH_3$. In another embodiment, the SARM prodrug is a compound of one of the above formulas wherein $R^1$ is $CH_2F$. In another embodiment, the SARM prodrug is a compound of one of the above formulas wherein $R^1$ is $CHF_2$. In another embodiment, the SARM prodrug is a compound of one of the above formulas wherein $R^1$ is $CF_3$. In another embodiment, the SARM prodrug is a compound of one of the above formulas wherein $R^1$ is $CH_2CH_3$. In another embodiment, the SARM prodrug is a compound of one of the above formulas wherein $R^1$ is $CF_2CF_3$.

Each substituent of each of X, Y, Z, G, T, Q, R and $R^1$, for each of the above formulas, represents a separate embodiment of the present invention. Further, each position enumerated above of each of the above substituents represents a separate embodiment of the present invention. Further, each number enumerated above of each of the above integers represents a separate embodiment of the present invention.

Each substituent at each of the indicated positions, for each of the structures depicted herein, represents a separate embodiment of the present invention. Each numerical value of n, m, and other numerical indicators in structures depicted herein represents a separate embodiment of the present invention.

The symbol "O" in structures of the present invention, when depicted with one single bond, refers, in one embodiment, to an —OH. In another embodiment, it refers to an O—. Each possibility represents a separate embodiment of the present invention.

In another embodiment, the present invention provides a prodrug of one of the parent SARM compounds depicted below (in the section "Selective Androgen Receptor Modulators"), wherein the prodrug modification is attached as depicted for the above prodrugs.

In another embodiment, the present invention provides a method of increasing a bioavailability of a SARM compound, comprising attaching to a chiral carbon of the SARM one of the structures:

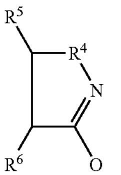
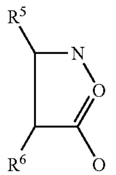
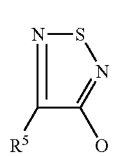
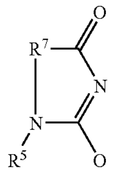
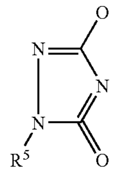
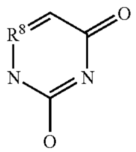
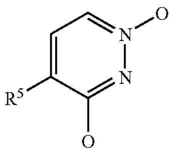
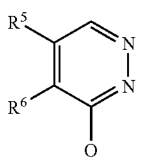
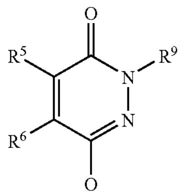
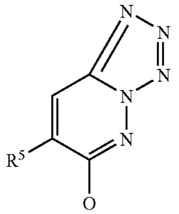
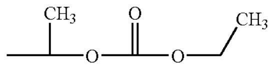
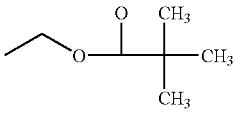
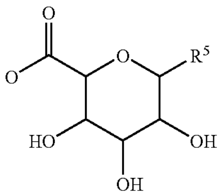
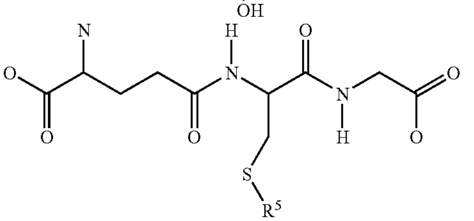
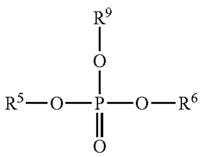
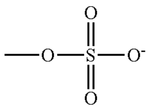

In one embodiment, "bioavailability" refers to a tissue-specific bioavailability. In another embodiment, "bioavailability" refers to any other type of bioavailability known in the art. Each possibility represents a separate embodiment of the present invention.

In another embodiment, the present invention provides a method of increasing a bioavailability of a SARM compound, comprising attaching to an A ring or a B ring of said SARM one of the structures described above as attached to the chiral carbon.

In another embodiment, the present invention provides a method of altering a solubility of a SARM compound, comprising attaching to a chiral carbon of said SARM one of the structures one of the structures described above in the method of increasing bioavailability.

In another embodiment, the present invention provides a method of altering a solubility of a SARM compound, comprising attaching to a chiral carbon of said SARM one of the structures one of the structures described above in the method of increasing bioavailability.

In another embodiment, the present invention provides a method of decreasing a toxicity of a SARM compound, comprising attaching to a chiral carbon of said SARM one of the structures described above in the method of increasing bioavailability.

In another embodiment, the present invention provides a method of decreasing a toxicity of a SARM compound, comprising attaching to an A ring or a B ring of said SARM one of the structures described above in the method of increasing bioavailability.

In another embodiment, the present invention provides a prodrug in which one of the parent SARM compounds is modified by adding an oxazolone, an isoxazolone, an oxazol, or an isoxazol, e.g. of the following structures:

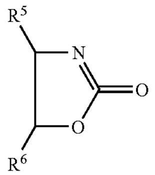
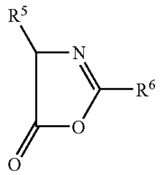
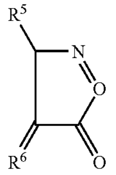

"Chiral carbon" refers, in one embodiment, to the carbon adjacent to the carbonyl carbon on the backbone of the SARM compound.

Definitions

In one embodiment, the substituent R denotes, where not otherwise indicated, an alkyl, haloalkyl, dihaloalkyl, trihaloalkyl, $CH_2F$, $CHF_2$, $CF_3$, $CF_2CF_3$; aryl, phenyl, F, Cl, Br, I, alkenyl, or hydroxyl (OH).

The term "prodrug" refers, in one embodiment, to a substance which can be converted in-vivo into a biologically active agent by such reactions as hydrolysis, esterification, desterification, activation, salt formation and the like. In another embodiment, "prodrug" refers to a derivative of a drug that exhibits an increased aqueous solubility. In another embodiment, "prodrug" refers to a derivative of a drug that exhibits a decreased aqueous solubility. In another embodiment, "prodrug" refers to a derivative of a drug that exhibits an increased bioavailability. In another embodiment, "prodrug" refers to a derivative of a drug that exhibits a decreased toxicity. In another embodiment, "prodrug" refers to a derivative of a drug that exhibits an improved partitioning to a particular body tissue or biological fluid. In another embodiment, "prodrug" refers to a derivative of a drug that exhibits altered pharmaceutical properties relative to the parent compound. In another embodiment, "prodrug" refers to a derivative of a drug that exhibits an altered pharmacological property relative to the parent compound. The SARM compound from which the prodrug is derived is referred to as a "parent SARM compound" or "parent compound."

In another embodiment, "prodrug" refers to a derivative of a drug that exhibits an enhanced delivery characteristic relative to the parent compound. In one embodiment, the enhanced delivery characteristic is an increased concentration in a target tissue. In another embodiment, increased transport to a specific tissue occurs via a particular transport mechanism. In another embodiment, the enhanced delivery characteristic is a decreased concentration in a non-target tissue. In another embodiment, the prodrug modification prevents exposure of tissue where active drug could be absorbed into systemic circulation, through limiting exposure of that tissue to active drug.

In another embodiment, the prodrug is enzymatically activated by an enzyme (e.g. bioreductive enzymes or enzymes prevalent in hypoxic tissue such as DT diaphorase, NADPH reductase, xanthine dehydrogenase, etc). In another embodiment, the prodrug is enzymatically activated in a target tissue by an tissue-specific or disease-specific enzyme present therein (e.g. PSA, PSMA, bacterial or viral enzymes, etc.). In another embodiment, the prodrug is enzymatically by an abzyme.

In another embodiment, the prodrug modification minimizes first pass metabolism. In another embodiment, the prodrug modification masks an organoleptic property of the parent compound. In other embodiment, the prodrug modification enhanced an other formulation attribute (e.g. a physicochemical property for analytical reasons, formulations or manufacturing reasons, etc.).

In another embodiment, the prodrug modification confers upon the parent compound a specific pharmacokinetic property. In one embodiment, the property is an extended release. In another embodiment the property is a compatibility with a route of administration. In another embodiment the property is an absorption phase.

Each of the above types of prodrugs represents a separate embodiment of the present invention.

In another embodiment, "prodrug" refers to any other definition of "prodrug" known in the art. Each definition represents a separate embodiment of the present invention.

An "alkyl" group refers to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen (e.g. F, Cl, Br, I), hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, e.g. by F, Cl, Br or I. A "halogen" refers to elements of Group VII or the periodic table, e.g. F, Cl, Br or I.

An "aryl" group refers to an aromatic group having at least one carbocyclic aromatic group or heterocyclic aromatic group, which may be unsubstituted or substituted by one or more groups selected from halogen (e.g. F, Cl, Br, I), haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naplithyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. An "alkenyl" group refers to a group having at least one carbon to carbon double bond.

An "arylalkyl" group refers to an alkyl bound to an aryl, wherein alkyl and aryl are as defined above. An example of an aralkyl group is a benzyl group.

In one embodiment, the invention relates to the use of an analog of the prodrug. In another embodiment, the invention relates to the use of a derivative thereof. In another embodiment, the invention relates to the use of an isomer thereof. In another embodiment, the invention relates to the use of a metabolite thereof. In another embodiment, the invention relates to the use of a pharmaceutically acceptable salt thereof. In another embodiment, the invention relates to the use of a pharmaceutical product thereof. In another embodiment, the invention relates to the use of a hydrate thereof. In another embodiment, the invention relates to the use of an N-oxide thereof. In another embodiment, the invention relates to the use of a polymorph thereof. In another embodiment, the invention relates to the use of a crystal thereof.

In another embodiment, the invention relates to the use of any of a combination of an analog, derivative, isomer, metabolite, pharmaceutically acceptable salt, pharmaceutical product, hydrate, or N-oxide, polymorph or crystal of the SARM compounds of the present invention.

As defined herein, the term "isomer" includes, but is not limited to, optical isomers and analogs, structural isomers and analogs, conformational isomers and analogs, and the like.

In one embodiment, this invention encompasses the use of various optical isomers of the SARM prodrugs It will be appreciated by those skilled in the art that the SARM prodrugs of the present invention contain at least one chiral center. Accordingly, the SARM prodrugs used in the methods of the present invention may exist in, and be isolated in, optically-active or racemic forms. Some prodrugs may also exhibit polymorphism. It is to be understood that the present invention encompasses any racemic, optically-active, polymorphic, or stereroisomeric form, or mixtures thereof, which form possesses properties useful in the methods as described herein. In one embodiment, the SARM prodrugs are the pure (R)-isomers. In another embodiment, the SARM prodrugs are the pure (S)-isomers. In another embodiment, the SARM prodrugs are a mixture of the (R) and the (S) isomers. In another embodiment, the SARM prodrugs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes pharmaceutically acceptable salts of amino-substituted prodrugs with organic and inorganic acids, for example, citric acid and hydrochloric acid. The invention also includes N-oxides of the amino substituents of the prodrugs described herein. Pharmaceutically acceptable salts can also be prepared from the phenolic prodrugs by treatment with inorganic bases, for example, sodium hydroxide. Also, esters of the phenolic prodrugs can be made with aliphatic and aromatic carboxylic acids, for example, acetic acid and benzoic acid esters.

This invention further includes derivatives of the SARM prodrugs The term "derivatives" includes but is not limited to ether derivatives, acid derivatives, amide derivatives, ester derivatives and the like. In addition, this invention further includes hydrates of the SARM prodrugs. The term "hydrate" includes but is not limited to hemihydrate, monohydrate, dihydrate, trihydrate and the like.

This invention further includes metabolites of the SARM prodrugs. The term "metabolite" means any substance produced from another substance by metabolism or a metabolic process.

This invention further includes pharmaceutical products of the SARM prodrugs. The term "pharmaceutical product" means a composition suitable for pharmaceutical use (pharmaceutical composition), as defined herein.

This invention further includes crystals of the SARM prodrugs. Furthermore, this invention provides polymorphs of the SARM prodrugs. The term "crystal" means a substance in a crystalline state. The term "polymorph" refers to a particular crystalline state of a substance, having particular physical properties such as X-ray diffraction, IR spectra, melting point, and the like "Suitable," when describing an atom, refers, in one embodiment, to an atom with appropriate reactivity to bind at the indicated location. In another embodiment, "suitable" refers to a sterically accessible atom. In another embodiment, "suitable" refers to an atom which can be conjugated without compromising an biological activity (e.g. ability to be hydrolyzed) of the chemical group. In another embodiment, "suitable" refers to any other definition of the term that would be understood by practioner of chemistry. Each possibility represents a separate embodiment of the present invention.

Biological Activity of Selective Androgen Receptor Modulator Prodrugs

SARM compounds are a novel class of androgen receptor targeting agents, that have been shown to be useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; g) decreasing the incidence of, halting or causing a regression of prostate cancer; and/or h) inducing apoptosis in a cancer cell. This section describes properties of the parent SARM compounds from which prodrugs are derived. The prodrugs are designed, in one embodiment, to be biologically processed to yield the parent SARM compound, or another SARM compound with AR binding activity, in the subject.

As used herein, receptors for extracellular signaling molecules are collectively referred to as "cell signaling receptors". Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glueocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cell, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction).

In one embodiment, the present invention is directed to prodrugs of SARM compounds that are agonist compounds. A receptor agonist is a substance which binds receptors and activates them. Thus, in one embodiment, the SARM compounds of the present invention are useful in binding to and activating steroidal hormone receptors. In one embodiment, the agonist compounds of the present invention is an agonist which binds the androgen receptor. In another embodiment, the compounds has high affinity for the androgen receptor. In another embodiment, the agonist also has anabolic activity. In another embodiment, the present invention provides prodrugs of SARM compounds that have agonistic and anabolic activity of a nonsteroidal compounds for the androgen receptor.

In another embodiment, the present invention is directed to prodrugs of SARM compounds that are antagonist compounds. A receptor antagonist is a substance which binds receptors and inactivates them. Thus, in one embodiment, the SARM compounds of the present invention bind and inactivate steroidal hormone receptors. In one embodiment, the antagonist compounds of the present invention is an antagonist which binds the androgen receptor. In another embodiment, the compounds has high affinity for the androgen receptor.

In yet another embodiment, the parent SARM compounds of the present invention can be classified as partial AR agonist/antagonists. The SARMs are AR agonists in some tissues, to cause increased transcription of AR-responsive genes (e.g. muscle anabolic effect). In other tissues, these compounds serve as inhibitors at the AR to prevent agonistic effects of the native androgens.

Assays to determine whether the parent SARM compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the parent SARM compounds to inhibit the growth of AR containing tissue.

As shown in Examples 3-6, SARM compounds stimulate the AR and have selective anabolic and, in some cases, androgenic activity. Thus, administration of SARM prodrugs that are converted in the subject to SARM compounds is an effective strategy for treating conditions disclosed herein.

The compounds of the present invention bind either reversibly or irreversibly to an AR. In one embodiment, the AR is an AR of a mammal. In another embodiment, the AR is an AR of a human. In one embodiment, the SARM compounds bind reversibly to the AR of a mammal, for example a human. Reversible binding of a compound to a receptor means, in one embodiment, that the compound can detach from the receptor after binding.

In another embodiment, the SARM compounds bind irreversibly to the androgen receptor of a mammal, for example a human. Thus, in one embodiment, the compounds of the present invention may contain a functional group (e.g. affinity label) that allows alkylation of the androgen receptor (i.e. covalent bond formation). Thus, in this case, the SARM compounds are alkylating agents that bind irreversibly to the receptor and, accordingly, cannot be displaced by a steroid, such as the endogenous ligands DHT and testosterone. An "alkylating agent" is defined herein as an agent that alkylates (forms a covalent bond) with a cellular component, such as DNA, RNA or enzyme. It is a highly reactive chemical that introduces alkyl radicals into biologically active molecules and thereby prevents their proper functioning. The alkylating moiety is an electrophilic group that interacts with nucleophilic moieties in cellular components.

According to one embodiment of the present invention, a method is provided for binding the SARM compounds of the present invention to an androgen receptor by contacting the receptor with a SARM prodrug and/or its analog, derivative, isomer, metabolite, pharmaceutically acceptable salt, pharmaceutical product, hydrate, N-oxide, polymorph, crystal or any combination thereof, under conditions effective to cause the SARM compounds to bind the androgen receptor. The binding of the SARM compounds to the androgen receptor enables the prodrugs of the present invention to be useful as a male contraceptive and in a number of hormone therapies. The agonist compounds bind to and activate the androgen receptor. The antagonist compounds bind to and inactivate the androgen receptor.

Androgen-dependent conditions which may be treated according to the present invention include those conditions which are associated with aging, such as hypogonadism, sarcopenia, erythropoiesis, osteoporosis, and any other conditions determined to be dependent upon low androgen (e.g., testosterone) levels.

In another embodiment, the present invention provides a a method of inducing apoptosis in a cancer cell, comprising the step of contacting the cell with with the selective androgen receptor modulator compound of the present invention and/or its analog, derivative, isomer, metabolite, pharmaceutically acceptable salt, pharmaceutical product, hydrate, N-oxide, prodrug, polymorph, crystal or any combination thereof, in an amount effective to induce apoptosis in said cancer cell.

As defined herein, "contacting" means that the SARM compound of the present invention is introduced into a sample containing the enzyme in a test tube, flask, tissue cultureor CHip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In another embodiment, the term "contacting" means that the SARM compound of the present invention is introduced into a subject receiving treatment, and the SARM compound is allowed to come in contact with the androgen receptor in vivo.

"Osteoporosis" refers, in one embodiment, to a thinning of the bones with reduction in bone mass due to depletion of calcium and bone protein. In another embodiment, osteoporosis predisposes a person to fractures, which are often slow to heal and heal poorly. Unchecked osteoporosis can lead to changes in posture, physical abnormality, and decreased mobility.

"BPH (benign prostate hyperplasia)" is, in one embodiment, a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

The term "depression" refers to an illness that involves the body, mood and thoughts, that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

The term "hair loss", medically known as alopecia, refers, in one embodiment, a common type of male-pattern baldness. Baldness typically begins with patch hair loss on the scalp and sometimes progresses to complete baldness and even loss of body hair. Hair loss affects both males and females.

"Anemia" refers to the condition of having less than the normal number of red blood cells or less than the normal quantity of hemoglobin in the blood. The oxygen-carrying capacity of the blood is, therefore, decreased. Persons with anemia may feel tired and fatigue easily, appear pale, develop palpitations and become usually short of breath. Anemia is caused by four basic factors: a) hemorrhage (bleeding); b) hemolysis (excessive destruction of red blood cells); c) underproduction of red blood cells; and d) not enough normal hemoglobin. There are many forms of anemia, including aplastic anemia, benzene poisoning, Fanconi anemia, hemolytic disease of the newborn, hereditary spherocytosis, iron deficiency anemia, osteopetrosis, pernicious anemia, sickle cell disease, thalassemia, myelodysplastic syndrome, and a variety of bone marrow diseases. As contemplated herein, the SARM compounds of the present invention are useful in preventing and/or treating any one or more of the above-listed forms of anemia.

"Obesity" refers to the state of being well above one's normal weight. Traditionally, a person is considered to be obese if they are more than 20 percent over their ideal weight. Obesity is defined, in another embodiment, as having a Body to Mass Index (BMI) of 30 or above. Obesity is often multi-factorial, based on both genetic and behavioral factors. Overweight due to obesity is a significant contributor to health problems. It increases the risk of developing a number of diseases including: Type 2 (adult-onset) diabetes; high blood pressure (hypertension); stroke (cerebrovascular accident or CVA); heart attack (myocardial infarction or MI); heart failure (congestive heart failure); cancer (certain forms such as cancer of the prostate and cancer of the colon and rectum); gallstones and gallbladder disease (cholecystitis); Gout and gouty arthritis; osteoarthritis (degenerative arthritis) of the knees, hips, and the lower back; sleep apnea (failure to breath normally during sleep, lowering blood oxygen); and Pickwickian syndrome (obesity, red face, underventilation and drowsiness). As contemplated herein, the term "obesity" includes any one of the above-listed obesity-related conditions and diseases. Thus the prodrugs of SARM compounds of the present invention are useful in preventing and/or treating obesity and any one or more of the above-listed obesity-related conditions and diseases.

Selective Androgen Receptor Modulators:

The SARM compounds of the present invention are, in one embodiment, a novel class of AR targeting agents that demonstrate androgenic or anti-androgenic and anabolic activity. In another embodiment, the SARM compounds of the present invention are a novel class of non-steroidal ligands for the AR.

In another embodiment, the SARM compounds of the present invention may be categorized into subgroups depending on their biological activity. For example, several SARM compounds have an agonistic effect on muscle or bone, whereas others have an antagonistic effect.

The AR is a ligand-activated transcriptional regulatory protein that mediates induction of male sexual development and function through its activity with endogenous androgens (male sex hormones). The androgens (e.g. DHT and testosterone) are steroids that are produced in the body by the testis and the cortex of the adrenal gland. Thus, in one embodiment, SARMS are AR ligands that differ from previously known AR ligands in that SARMS are non-steroidal.

A receptor agonist is, in one embodiment, a substance that binds a receptor and activates it. A receptor partial agonist is, in one embodiment, a substance that binds a receptor and partially activates it. A receptor antagonist is, in one embodiment, a substance that binds a receptor and inactivates it. In one embodiment, the SARM compounds of the present invention have a tissue-selective effect, wherein one agent may be an agonist, partial agonist and/or antagonist, depending on the tissue. For example, the SARM compound may stimulate muscle tissue and at the same time inhibit prostate tissue. In one embodiment, the SARMs of the present invention are AR agonists. In another embodiment, the SARMs are AR antagonists. Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds inhibit the growth of AR containing tissue.

In another embodiment, the SARM compounds of the present invention can be classified as partial AR agonist/antagonists. The SARMs are AR agonists in some tissues, causing increased transcription of AR-responsive genes (e.g. muscle anabolic effect). In other tissues, these compounds serve as competitive inhibitors of testosterone and/or dihydrotestosterone (DHT) on the AR to prevent agonistic effects of the native androgens. Each type of SARM represents a separate embodiment of the present invention.

In one embodiment, the SARM compounds of the present invention bind reversibly to the AR. In another embodiment, the SARM compounds bind irreversibly to the AR. The compounds of the present invention may, in one embodiment, contain a functional group (affinity label) that allows alkylation of the AR (i.e. covalent bond formation). Thus, in this case, the compounds bind irreversibly to the receptor and, accordingly, cannot be displaced by a steroid, such as the endogenous ligands DHT and testosterone.

In one embodiment of the present invention, the SARM compound is administered to the subject. In another embodiment, an analogue of the SARM is administered. In another embodiment, a derivative of the SARM is administered. In another embodiment, an isomer of the SARM is administered. In another embodiment, a metabolite of the SARM is administered. In another embodiment, a pharmaceutically acceptable salt of the SARM is administered. In another embodiment, a pharmaceutical product of the SARM is administered. In another embodiment, a hydrate of the SARM is administered. In another embodiment, an N-oxide of the SARM is administered. In another embodiment, the methods of the present invention comprise administering any of a combination of an analogue, derivative, isomer, metabolite, pharmaceutically acceptable salt, pharmaceutical product, hydrate or N-oxide of the SARM. Each possibility represents a separate embodiment of the present invention.

The term "isomer" refers, in one embodiment, an optical isomer. In another embodiment, "isomer" refers to an analog. In another embodiment, "isomer" refers to a structural isomer. In another embodiment, "isomer" refers to a structural analog. In another embodiment, "isomer" refers to a conformational isomer. In another embodiment, "isomer" refers to a conformational analog. In another embodiment, "isomer" refers to any other type of isomer known in the art. Each type of isomer represents a separate embodiment of the present invention.

In another embodiment, this invention encompasses the use of various optical isomers of the SARM compound. It will be appreciated by those skilled in the art that the SARMs of the present invention contain at least one chiral center. Accordingly, the SARMs used in the methods of the present invention may exist in, and be isolated in, optically active or racemic forms. Some compounds may also exhibit polymorphism. It is to be understood that the present invention encompasses any racemic, optically active, polymorphic, or sterereoisomeric form, or mixtures thereof, which form possesses properties useful in the treatment of androgen-related conditions described herein In one embodiment, the SARMs are the pure (R)-isomers. In another embodiment, the SARMs are the pure (S)-isomers. In another embodiment, the SARMs are a mixture of the (R) and (S) isomers. In another embodiment, the SARMs are a racemic mixture comprising an equal amount of the (R) and (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes, in another embodiment, pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes, in another embodiment, derivatives of the SARM compounds. The term “derivatives” includes but is not limited to ether derivatives, acid derivatives, amide derivatives, ester derivatives and the like. In addition, this invention further includes hydrates of the SARM compounds. The term “hydrate” includes but is not limited to hemi-hydrate, monohydrate, dihydrate, trihydrate and the like.

This invention further includes, in another embodiment, metabolites of the SARM compounds. The term “metabolite” refers, in one embodiment, to any substance produced from another substance by metabolism or a metabolic process.

This invention further includes, in one embodiment, pharmaceutical products of the SARM compounds. The term “pharmaceutical product” refers, in one embodiment, to a composition suitable for pharmaceutical use (pharmaceutical composition), as defined herein.

In one embodiment, the SARM compound of the present invention is a compound represented by the structure of formula I:

I

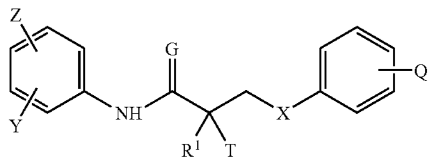

wherein

G is O or S;

X is a bond, O, $CH_2$, NH, Se, PR, NO or NR;

T is OH, OR, —$NHCOCH_3$, or NHCOR;

Z is $NO_2$, CN, COOH, COR, NHCOR or CONHR;

Y is $CF_3$, F, I, Br, Cl, CN, $CR_3$ or $SnR_3$;

Q is alkyl, F, I, Br, Cl, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, or NCO;

or Q together with the benzene ring to which it is attached is a fused ring system represented by structure A, B or C:

A

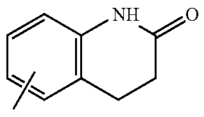

B

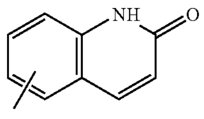

-continued

C

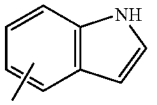

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R^1$ is $CH_3$, $CH_2F$, $CHF_2$, $CF_3$, $CH_2CH_3$, or $CF_2CF_3$.

In another embodiment, the SARM compound of the present invention is represented by the structure of formula (II),

II

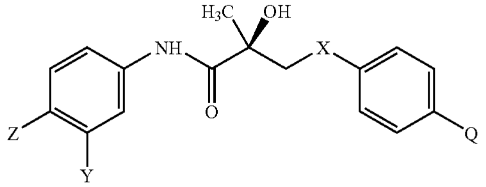

wherein

X is a bond, O, $CH_2$, NH, Se, PR, NO or NR;

Z is $NO_2$, CN, COOH, COR, NHCOR or CONHR;

Y is $CF_3$, F, I, Br, Cl, CN, $CR_3$ or $SnR_3$;

Q is alkyl, F, I, Br, Cl, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, or NCO;

or Q together with the benzene ring to which it is attached is a fused ring system represented by structure A, B or C;

A

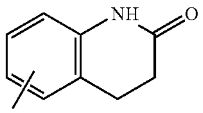

B

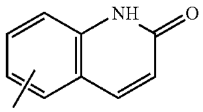

C

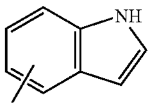

and R is alkyl, haloalkyl, dihaloalkyl, trihaloalkyl, $CH_2F$, $CHF_2$, $CF_3$, $CF_2CF_3$, aryl, phenyl, F, I, Br, Cl, alkenyl or OH.

In one embodiment, the SARM compound is a compound of formula II wherein X is O. In another embodiment, the SARM compound is a compound of formula II wherein Z is $NO_2$. In another embodiment, the SARM compound is a compound of formula II wherein Z is CN. In another embodiment, the SARM compound is a compound of formula II wherein Y is $CF_3$. In another embodiment, the SARM compound is a compound of formula II wherein Q is $NHCOCH_3$. In another embodiment, the SARM compound is a compound of formula II wherein Q is F.

In one embodiment, the substituent R in the compound of formula II is an alkyl group. In another embodiment, the substituent R is a haloalkyl group. In another embodiment, the substituent R is a dihaloalkyl group. In another embodiment, the substituent R is a trihaloalkyl group. In another embodiment, the substituent R is a $CH_2F$ moiety. In another embodiment, the substituent R is a $CHF_2$ moiety. In another embodiment, the substituent R is a $CF_3$ moiety. In another embodiment, the substituent R is a $CF_2CF_3$ moiety. In another embodiment, the substituent R is an aryl group. In another embodiment, the substituent R is a phenyl group. In another embodiment, the substituent R is F. In another embodiment, the substituent R is I. In another embodiment, the substituent R is a Br. In another embodiment, the substituent R is Cl. In another embodiment, the substituent R is an alkenyl group. In another embodiment, the substituent R is an OH moiety. Each substituent represents a separate embodiment of the present invention.

In another embodiment, the SARM compound of the present invention is a compound represented by the structure of formula III:

III

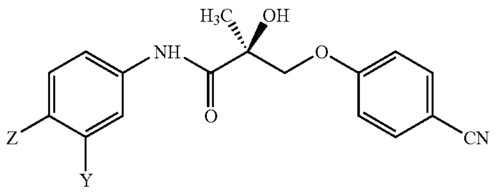

wherein

Z is $NO_2$, CN, COR, or CONHR; and

Y is I, $CF_3$, Br, Cl, or $SnR_3$.

In one embodiment, Z in compound (III) is $NO_2$. In another embodiment, Z in compound (III) is CN. In another embodiment, Y in compound (II) is $CF_3$. In another embodiment, Q in compound (III) is CN.

In another embodiment, the SARM compound is a compound represented by a structure of formula IV:

IV

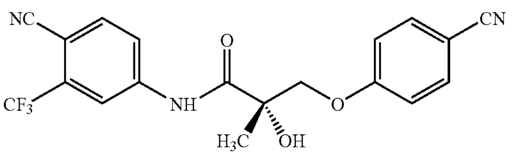

In another embodiment, the SARM compound of the present invention is a compound represented by the structure of formula V:

V

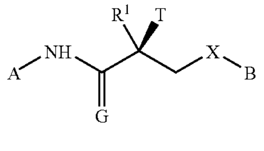

wherein

X is a bond, O, $CH_2$, NH, Se, PR, NO or NR;

G is O or S;

$R^1$ is $CH_3$, $CH_2F$, $CHF_2$, $CF_3$, $CH_2CH_3$, or $CF_2CF_3$;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, F, I, Br, Cl, alkenyl or OH;

A is a ring selected from:

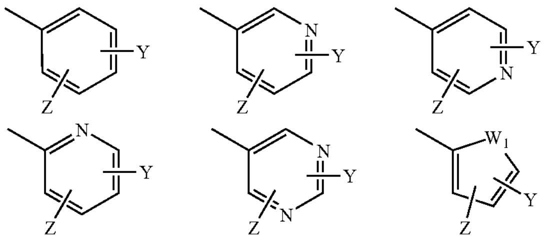

and

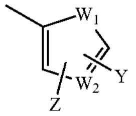

B is a ring selected from:

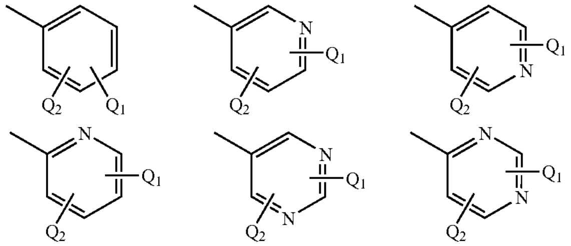

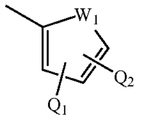

and

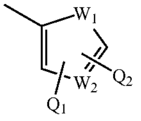

wherein

A and B are not simultaneously a benzene ring;

Z is $NO_2$, CN, COOH, COR, NHCOR or CONHR;

Y is $CF_3$, F, I, Br, Cl, CN, $CR_3$ or $SnR_3$;

$Q_1$ and $Q_2$ are independently of each other a hydrogen, alkyl, F, I, Br, Cl, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, NCO,

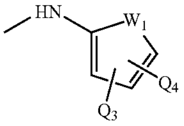

or

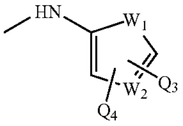

$Q_3$ and $Q_4$ are independently of each other a hydrogen, alkyl, F, I, Br, Cl, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, or NCO;

$W_1$ is O, NH, NR, NO or S; and $W_2$ is N or NO.

In one embodiment, the SARM compound is a compound of formula V wherein X is O. In another embodiment, the SARM compound is a compound of formula V wherein G is O. In another embodiment, the SARM compound is a compound of formula V wherein T is OH. In another embodiment, the SARM compound is a compound of formula V wherein $R^1$ is $CH_3$. In another embodiment, the SARM compound is a compound of formula V wherein Z is $NO_2$. In another embodiment, the SARM compound is a compound of formula V wherein Z is CN. In another embodiment, the SARM compound is a compound of formula V wherein Y is $CF_3$. In another embodiment, the SARM compound is a compound of formula V wherein $Q_1$ is $NHCOCH_3$. In another embodiment, the SARM compound is a compound of formula V wherein $Q_1$ is F.

The substituents Z and Y can be, in one embodiment, in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents $Q_1$ and $Q_2$ can be, in one embodiment, in any position of the ring carrying these substituents (hereinafter "B ring"). In one embodiment, the substitutent $Q_1$ is in the para position of the B ring. In another embodiment, the substituent is $Q_2$ is H. In another embodiment, the substitutent $Q_1$ is in the para position of the B ring and the substituent is $Q_2$ is H. In another embodiment, the substitutent $Q_1$ is $NHCOCH_3$ and is in the para position of the B ring, and the substituent is $Q_2$ is H.

Each substituent of each of the above variables represents a separate embodiment of the present invention. Further, each position enumerated above of each of the above substituents represents a separate embodiment of the present invention.

In another embodiment, the SARM compound of the present invention is a compound represented by the structure of formula VI:

VI

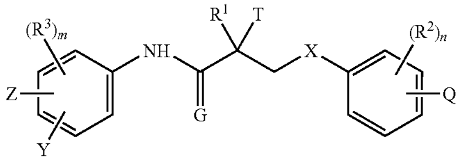

wherein

X is a bond, O, $CH_2$, NH, Se, PR, NO or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, F, I, Br, Cl, alkenyl or OH;

$R^1$ is $CH_3$, $CH_2F$, $CHF_2$, $CF_3$, $CH_2CH_3$, or $CF_2CF_3$;

$R^2$ is F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $NR_2$, SR, SCN, NCS, OCN, NCO;

$R^3$ is F, Cl, Br, I, CN, $NO_2$, COR, COOH, CONHR, $CF_3$, or $SnR_3$;

or $R^3$ together with the benzene ring to which it is attached forms a fused ring system represented by the structure:

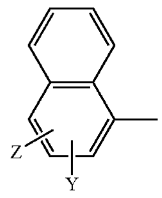

or

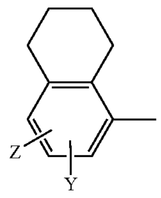

Z is $NO_2$, CN, COR, COOH, or CONHR;

Y is $CF_3$, F, Br, Cl, I, CN, or $SnR_3$;

Q is H, alkyl, F, I, Br, Cl, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, or SR;

or Q together with the benzene ring to which it is attached is a fused ring system represented by structure A, B or C:

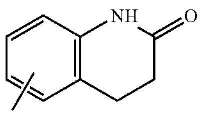

A

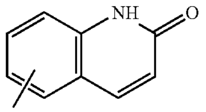

B

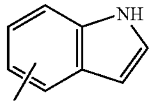

C n is an integer of 1, 2, 3, of 4; and m is an integer of 1, 2, or 3.

In one embodiment, the SARM compound is a compound of formula VI wherein X is O. In another embodiment, the SARM compound is a compound of formula VI wherein G is O. In another embodiment, the SARM compound is a compound of formula VI wherein Z is $NO_2$. In another embodiment, the SARM compound is a compound of formula VI wherein Z is CN. In another embodiment, the SARM compound is a compound of formula VI wherein Y is $CF_3$. In another embodiment, the SARM compound is a compound of formula VI wherein Q is $NHCOCH_3$. In another embodiment, the SARM compound is a compound of formula VI wherein Q is F. In another embodiment, the SARM compound is a compound of formula VI wherein T is OH. In another embodiment, the SARM compound is a compound of formula VI wherein $R_1$ is $CH_3$. In another embodiment, the SARM compound is a compound of formula VI wherein Q is F and $R_2$ is $CH_3$. In another embodiment, the SARM compound is a compound of formula VI wherein Q is F and $R_2$ is Cl.

The substituents Z, Y, and $R_3$ can be, in one embodiment, in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents Q and $R_2$ can be, in one embodiment, in any position of the ring carrying these substituents (hereinafter "B ring"). In one embodiment, the substitutent Q is in the para position of the B ring. In another embodiment, the substitutent Q is in the para position of the B ring. In another embodiment, the substitutent Q is $NHCOCH_3$ and is in the para position of the B ring.

In one embodiment, when the integers m and n are greater than one, the substituents $R^2$ and $R^3$ are not limited to one particular substituent, and can be any combination of the substituents listed above.

Each substituent of each of the above variables represents a separate embodiment of the present invention. Further, each position enumerated above of each of the above substituents represents a separate embodiment of the present invention. Further, each number enumerated above of each of the above integers represents a separate embodiment of the present invention.

In another embodiment, the SARM compound of the present invention is a compound represented by the structure of formula VII:

VII

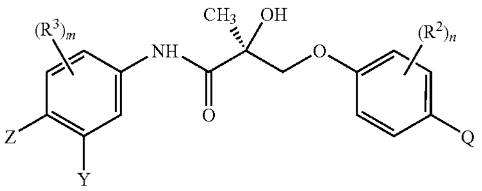

wherein $R^2$ is F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $NR_2$, or SR;

$R^3$ is F, Cl, Br, I, CN, $NO_2$, COR, COOH, CONHR, $CF_3$, or $SnR_3$;

or $R^3$ together with the benzene ring to which it is attached forms a fused ring system represented by the structure:

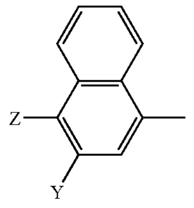

or

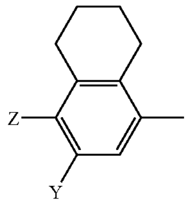

R is alkyl, haloalkyl, dihaloalkyl, trihaloalkyl, $CH_2F$, $CHF_2$, $CF_3$, $CF_2CF_3$, aryl, phenyl, F, I, Br, Cl, alkenyl or OH;

Z is $NO_2$, CN, COR, COOH, or CONHR;

Y is $CF_3$, F, Br, Cl, I, CN, or $SnR_3$;

Q is H, alkyl, F, I, Br, $C_1$, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, or SR;

or Q together with the benzene ring to which it is attached is a fused ring system represented by structure A, B or C:

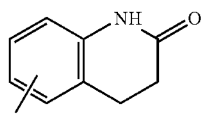

A

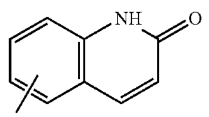

B

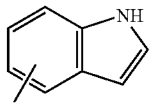

C n is an integer of 1-4; and m is an integer of 1-3.

In another embodiment, the SARM is a compound of formula VII wherein Z is $NO_2$. In another embodiment, the SARM is a compound of formula VII wherein Z is CN. In another embodiment, the SARM is a compound of formula VII wherein Y is $CF_3$. In another embodiment, the SARM is a compound of formula VII wherein Q is $NHCOCH_3$. In another embodiment, the SARM is a compound of formula VII wherein Q is F. In another embodiment, the SARM is a compound of formula VII wherein Q is F and $R^2$ is $CH_3$. In another embodiment, the SARM is a compound of formula VII wherein Q is F and $R^2$ is Cl.

The substituents Z, Y and $R^3$ can be in, in one embodiment, any position of the A ring, and the substituents Q and $R^2$ can be, in one embodiment, in any position of B ring, as described above for compound VI. Furthermore, as discussed above, when the integers m and n are greater than one, the substituents $R^2$ and $R^3$ are not limited to one particular substituent, and can be any combination of the substituents listed above.

Each substituent of each of the above variables represents a separate embodiment of the present invention. Further, each position enumerated above of each of the above substituents represents a separate embodiment of the present invention. Further, each number enumerated above of each of the above integers represents a separate embodiment of the present invention.

In another embodiment, the SARM compound of the present invention is a compound represented by the structure of formula VIII.

VIII

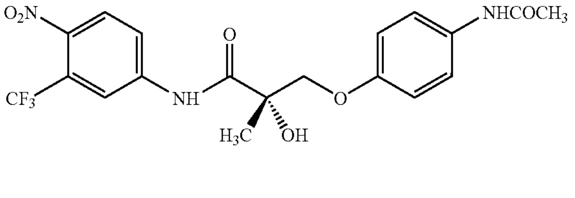

In another embodiment, the SARM compound of the present invention is a compound represented by the structure of formula IX.

IX

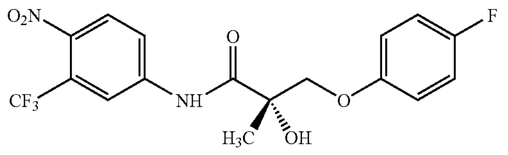

In another embodiment, the SARM compound of the present invention is a compound represented by the structure of formula X.

X

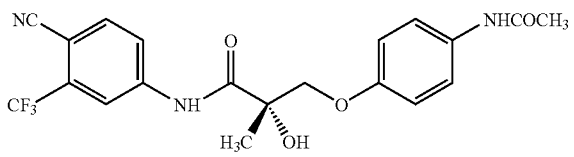

In another embodiment, the SARM compound of the present invention is a compound represented by the structure of formula XI.

XI

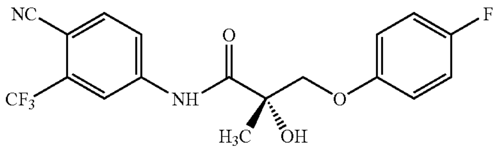

In another embodiment, the SARM compound of the present invention is a compound represented by the structure of formula XII.

XII

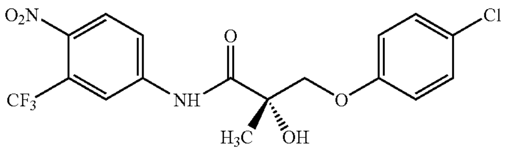

In another embodiment, the SARM compound of the present invention is a compound represented by the structure of formula XIII.

XIII

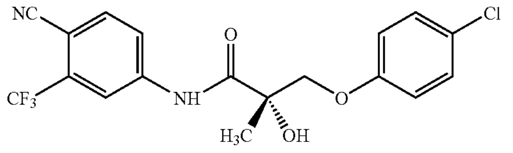

In another embodiment, the SARM compound is a compound represented by a structure of formula XIV:

XIV

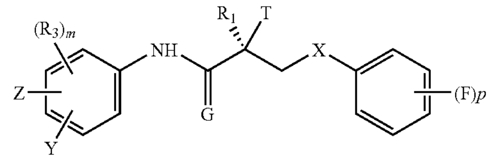

In one embodiment, p is 2. In another embodiment, p is 3. In another embodiment, p is 4. In another embodiment, p is 5. The rest of the substituents are as defined above for formula VI.

In another embodiment, the SARM compound is a compound represented by a structure of formula XV:

XV

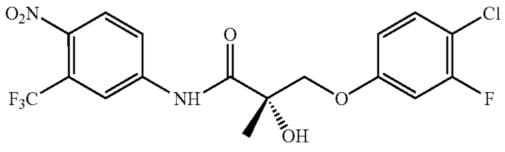

In another embodiment, the SARM compound is a compound represented by a structure of formula XVI:

XVI

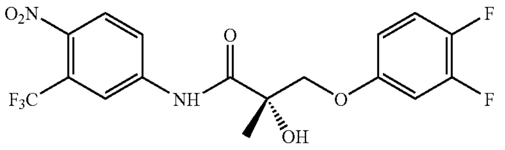

In another embodiment, the SARM compound is a compound represented by a structure of formula XVII:

XVII

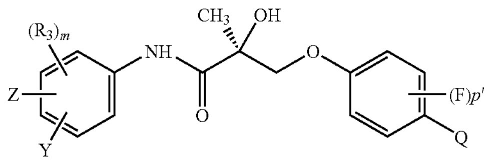

In another embodiment, p is 1. In one embodiment, p is 2. In another embodiment, p is 3. In another embodiment, p is 4. The rest of the substituents are as defined above for formula VII.

In another embodiment, the SARM compound is a compound represented by a structure of formula XVIII:

XVIII

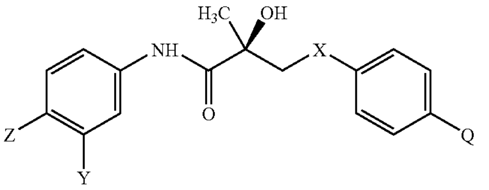

In one embodiment, the SARM is a compound of formula XVIII wherein Q is acetamido ($NHCOH_3$). In another embodiment, the SARM is a compound of formula XVIII wherein Q is trifluoroacetamido ($NHCOCF_3$).

In another embodiment, the SARM is a compound of formula XVIII wherein Z is $NO_2$. In another embodiment, the SARM is a compound of formula XVIII wherein Z is CN. In another embodiment, the SARM is a compound of formula XVIII wherein Z is COR. In another embodiment, the SARM is a compound of formula XVIII wherein Z is CONHR.

In another embodiment, the SARM is a compound of formula XVIII wherein Y is $CF_3$. In another embodiment, the SARM is a compound of formula XVIII wherein Y is I. In another embodiment, the SARM is a compound of formula XVIII wherein Y is Br. In another embodiment, the SARM is a compound of formula XVIII wherein Y is Cl. In another embodiment, the SARM is a compound of formula XVIII wherein Y is $SnR_3$.

In another embodiment, the SARM is a compound of formula XVIII wherein R is an alkyl group. In another embodiment, the SARM is a compound of formula XVIII wherein R is OH.

Each substituent of each of the above variables represents a separate embodiment of the present invention. Further, each position enumerated above of each of the above substituents represents a separate embodiment of the present invention.

In another embodiment, the SARM compound is a compound represented by a structure of formula XIX:

XIX

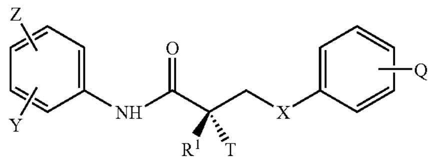

wherein

X is O, $CH_2$, NH, Se, PR, NO Or NR;

T is OH, OR, —$NHCOCH_3$, or NHCOR;

Z is $NO_2$, CN, COOH, COR, NHCOR or CONHR;

Y is $CF_3$, F, I, Br, Cl, CN, $CR_3$ or $SnR_3$;

Q is alkyl, F, I, Br, Cl, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR;

or Q together with the benzene ring to which it is attached is a fused ring system represented by structure A, B or C:

A

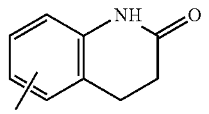

B

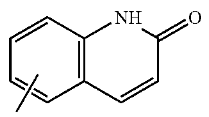

C

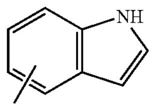

R is alkyl, haloalkyl, dihaloalkyl, trihaloalkyl, $CH_2F$, $CHF_2$, $CF_3$, $CF_2CF_3$, aryl, phenyl, F, I, Br, Cl, alkenyl or OH; and $R^1$ is $CH_3$, $CH_2F$, $CHF_2$, $CF_3$, $CH_2CH_3$, or $CF_2CF_3$.

Each substituent of each of the above variables represents a separate embodiment of the present invention. Further, each position enumerated above of each of the above substituents represents a separate embodiment of the present invention.

In one embodiment, the SARM compound is a compound of one of the above formulas wherein X is O. In another embodiment, the SARM compound is a compound of one of the above formulas wherein X is a bond. In another embodiment, the SARM compound is a compound of one of the above formulas wherein X is $CH_2$. In another embodiment, the SARM compound is a compound of one of the above formulas wherein X is NH. In another embodiment, the SARM compound is a compound of one of the above formulas wherein X is Se. In another embodiment, the SARM compound is a compound of one of the above formulas wherein X is PR. In another embodiment, the SARM compound is a compound of one of the above formulas wherein X is NO. In another embodiment, the SARM compound is a compound of one of the above formulas wherein X is NR.

In one embodiment, the SARM compound is a compound of one of the above formulas wherein G is O. In another embodiment, the SARM compound is a compound of one of the above formulas wherein G is S.

In one embodiment, the SARM compound is a compound of one of the above formulas wherein T is OH. In another embodiment, the SARM compound is a compound of one of the above formulas wherein T is OR. In another embodiment, the SARM compound is a compound of one of the above formulas wherein T is $NHCOCH_3$. In another embodiment, the SARM compound is a compound of one of the above formulas wherein T is NHCOR.

In another embodiment, the SARM compound is a compound of one of the above formulas wherein Z is $NO_2$. In another embodiment, the SARM compound is a compound of one of the above formulas wherein Z is CN. In another embodiment, the SARM compound is a compound of one of the above formulas wherein Z is COOH. In another embodiment, the SARM compound is a compound of one of the above formulas wherein Z is COR. In another embodiment, the SARM compound is a compound of one of the above formulas wherein Z is NHCOR. In another embodiment, the SARM compound is a compound of one of the above formulas wherein Z is CONHR.

In another embodiment, the SARM compound is a compound of one of the above formulas wherein Y is $CF_3$. In another embodiment, the SARM compound is a compound of one of the above formulas wherein Y is F. In another embodiment, the SARM compound is a compound of one of the above formulas wherein Y is I. In another embodiment, the SARM compound is a compound of one of the above formulas wherein Y is Br. In another embodiment, the SARM compound is a compound of one of the above formulas wherein Y is Cl. In another embodiment, the SARM compound is a compound of one of the above formulas wherein Y is CN. In another embodiment, the SARM compound is a compound of one of the above formulas wherein Y is $CR_3$. In another embodiment, the SARM compound is a compound of one of the above formulas wherein Y is $SnR_3$.

In another embodiment, the SARM compound is a compound of one of the above formulas wherein Q is $NHCOCH_3$. In another embodiment, the SARM compound is a compound of one of the above formulas wherein Q is F. In another embodiment, the SARM compound is a compound of one of the above formulas wherein Q is alkyl. In another embodiment, the SARM compound is a compound of one of the above formulas wherein Q is I. In another embodiment, the SARM compound is a compound of one of the above formulas wherein Q is Br. In another embodiment, the SARM compound is a compound of one of the above formulas wherein Q is Cl. In another embodiment, the SARM compound is a compound of one of the above formulas wherein Q is $CF_3$. In another embodiment, the SARM compound is a compound of one of the above formulas wherein Q is CN. In another embodiment, the SARM compound is a compound of one of the above formulas wherein Q is $CR_3$. In another embodiment, the SARM compound is a compound of one of the above formulas wherein Q is $SnR_3$. In another embodiment, the SARM compound is a compound of one of the above formulas wherein Q is $NR_2$. In another embodiment, the SARM compound is a compound of one of the above formulas wherein Q is $NHCOCF_3$. In another embodiment, the SARM compound is a compound of one of the above formulas wherein Q is NHCOR. In another embodiment, the SARM compound is a compound of one of the above formulas wherein Q is NHCONHR. In another embodiment, the SARM compound is a compound of one of the above formulas wherein Q is NHCOOR. In another embodiment, the SARM compound is a compound of one of the above formulas wherein Q is OCONHR. In another embodiment, the SARM compound is a compound of one of the above formulas wherein Q is CONHR. In another embodiment, the SARM compound is a compound of one of the above formulas wherein Q is $NHCSCH_3$. In another embodiment, the SARM compound is a compound of one of the above formulas wherein Q is $NHCSCF_3$. In another embodiment, the SARM compound is a compound of one of the above formulas wherein Q is NHCSR. In another embodiment, the SARM compound is a compound of one of the above formulas wherein Q is $NHSO_2CH_3$. In another embodiment, the SARM compound is a compound of one of the above formulas wherein Q is $NHSO_2R$. In another embodiment, the SARM compound is a compound of one of the above formulas wherein Q is OR. In another embodiment, the SARM compound is a compound of one of the above formulas wherein Q is COR. In another embodiment, the SARM compound is a compound of one of the above formulas wherein Q is OCOR. In another embodiment, the SARM compound is a compound of one of the above formulas wherein Q is $OSO_2R$. In another embodiment, the SARM compound is a compound of one of the above formulas wherein Q is $SO_2R$. In another embodiment, the SARM compound is a compound of one of the above formulas wherein Q is SR. In another embodiment, the SARM compound is a compound of one of the above formulas wherein Q is SCN. In another embodiment, the SARM compound is a compound of one of the above formulas wherein Q is NCS. In another embodiment, the SARM compound is a compound of one of the above formulas wherein Q is OCN. In another embodiment, the SARM compound is a compound of one of the above formulas wherein Q is NCO.

In another embodiment, the SARM compound is a compound of one of the above formulas wherein Q together with the benzene ring to which it is attached is a fused ring system represented by structure A, B or C:

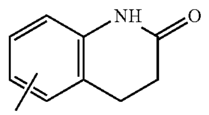

A

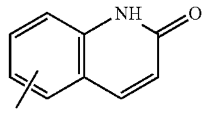

B

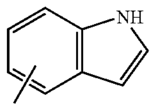

C

In another embodiment, the SARM compound is a compound of one of the above formulas wherein R is alkyl. In another embodiment, the SARM compound is a compound of one of the above formulas wherein R is haloalkyl. In another embodiment, the SARM compound is a compound of one of the above formulas wherein R is dihaloalkyl. In another embodiment, the SARM compound is a compound of one of the above formulas wherein R is trihaloalkyl In another embodiment, the SARM compound is a compound of one of the above formulas wherein R is $CH_2F$. In another embodiment, the SARM compound is a compound of one of the above formulas wherein R is $CHF_2$. In another embodiment, the SARM compound is a compound of one of the above formulas wherein R is $CF_3$. In another embodiment, the SARM compound is a compound of one of the above formulas wherein R is $CF_2CF_3$. In another embodiment, the SARM compound is a compound of one of the above formulas wherein R is aryl. In another embodiment, the SARM compound is a compound of one of the above formulas wherein R is phenyl. In another embodiment, the SARM compound is a compound of one of the above formulas wherein R is F. In another embodiment, the SARM compound is a compound of one of the above formulas wherein R is I. In another embodiment, the SARM compound is a compound of one of the above formulas wherein R is Br. In another embodiment, the SARM compound is a compound of one of the above formulas wherein R is Cl. In another embodiment, the SARM compound is a compound of one of the above formulas wherein R is alkenyl. In another embodiment, the SARM compound is a compound of one of the above formulas wherein R is OH.

In another embodiment, the SARM compound is a compound of one of the above formulas wherein $R^1$ is $CH_3$. In another embodiment, the SARM compound is a compound of one of the above formulas wherein $R^1$ is $CH_2F$. In another embodiment, the SARM compound is a compound of one of the above formulas wherein $R^1$ is $CHF_2$. In another embodiment, the SARM compound is a compound of one of the above formulas wherein $R^1$ is $CF_3$. In another embodiment, the SARM compound is a compound of one of the above formulas wherein $R^1$ is $CH_2CH_3$. In another embodiment, the SARM compound is a compound of one of the above formulas wherein $R^1$ is $CF_2CF_3$.

Each substituent of each of X, Y, Z, G, T, Q, R and $R^1$, for each of the above formulas, represents a separate embodiment of the present invention. Further, each position enumerated above of each of the above substituents represents a separate embodiment of the present invention. Further, each number enumerated above of each of the above integers represents a separate embodiment of the present invention In another embodiment, the SARM compound is a compound represented by a structure of formula XX:

XX

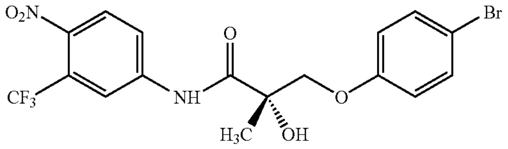

In another embodiment, the SARM compound is a compound represented by a structure of formula XXI:

XXI

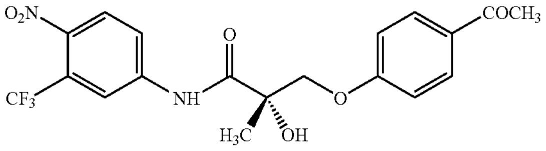

In another embodiment, the SARM compound is a compound represented by a structure of formula XXII:

XXII

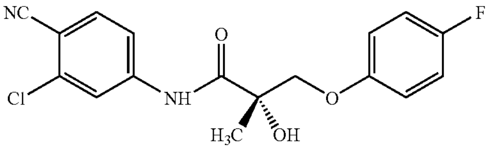

In another embodiment, the SARM compound is a compound represented by a structure of formula XXIII:

XXIII

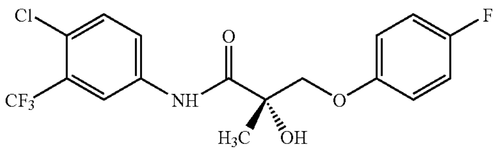

In another embodiment, the SARM compound is a compound represented by a structure of formula XXIV:

XXIV

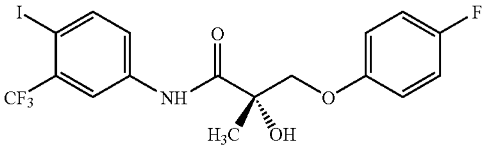

In another embodiment, the SARM compound is a compound represented by a structure of formula XXV:

XXV

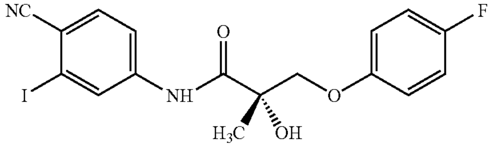

In another embodiment, the SARM compound is a compound represented by a structure of formula (XXVI):

XXVI

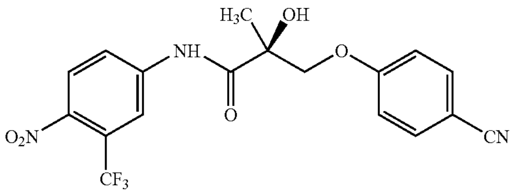

In another embodiment, the SARM compound is a compound represented by a structure of formula (XXVII):

XXVII

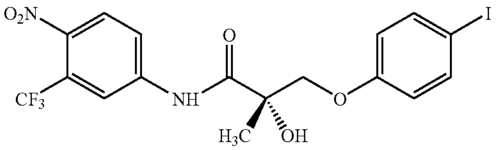

In another embodiment, the SARM compound is a compound represented by a structure of formula (XXVIII):

XXVIII

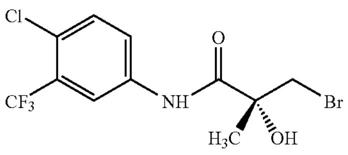

In another embodiment, the SARM compound is a compound represented by a structure of formula (XXIX):

XXIX

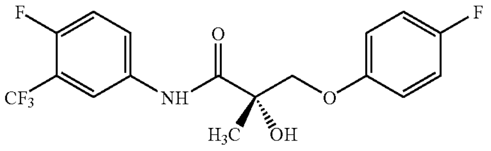

In another embodiment, the SARM compound is a compound represented by a structure of formula (XXX):

XXX

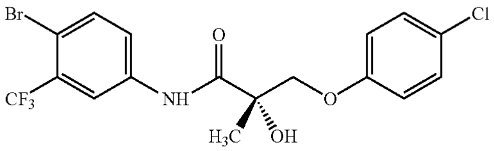

In another embodiment, the SARM compound is a compound represented by a structure of formula (XXXI):

XXXI

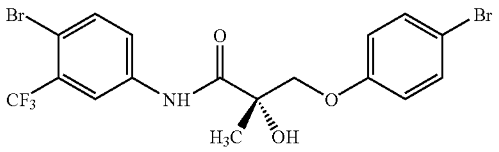

In another embodiment, the SARM compound is a compound represented by a structure of formula (XXXII):

XXXII

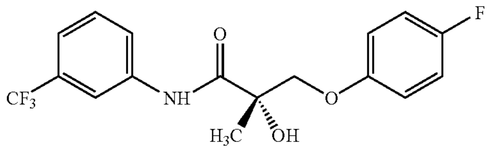

In another embodiment, the SARM compound is a compound represented by a structure of formula (XXXIII):

XXXIII

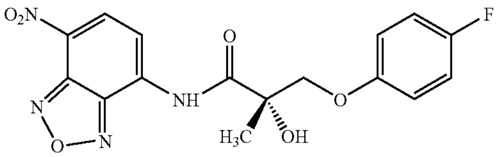

In another embodiment, the SARM compound is a compound represented by a structure of formula (XXXIV):

XXXIV

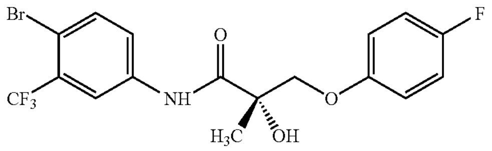

In another embodiment, the SARM compound is a compound represented by a structure of formula (XXXV):

XXXV

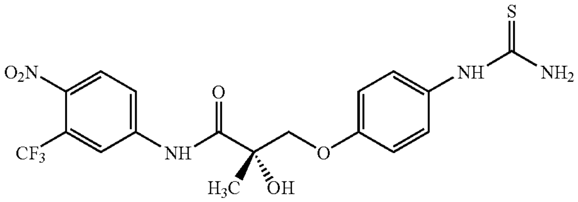

In another embodiment, the SARM compound is a compound represented by a structure of formula (XXXVI):

XXXVI

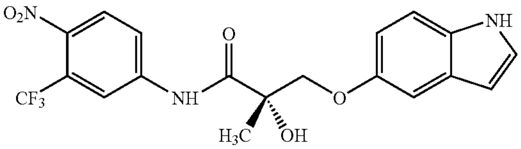

In another embodiment, the SARM compound is a compound represented by a structure of formula (XXXVII):

XXXVII

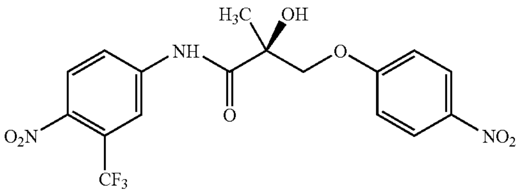

In another embodiment, the SARM compound is a compound represented by a structure of formula (XXXVIII):

XXXVIII

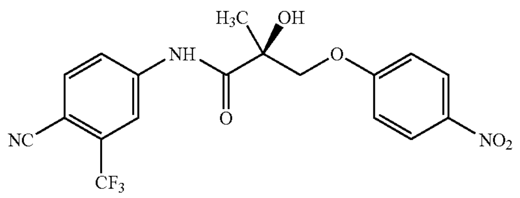

In another embodiment, the SARM compound is a compound represented by a structure of formula (XXXIX):

XXXIX

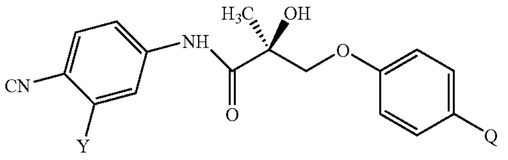

In another embodiment, the SARM compound is a compound of formula XXIX wherein Q is F. In another embodiment, the SARM compound is a compound of formula XXIX wherein Q is Cl. In another embodiment, the SARM compound is a compound of formula XXIX wherein Q is Br. In another embodiment, the SARM compound is a compound of formula XXIX wherein Q is I. In another embodiment, the SARM compound is a compound of formula XXIX wherein Q is $NHCOCH_3$. In another embodiment, the SARM compound is a compound of formula XXIX wherein Q is $NHCOCF_3$.

In another embodiment, the SARM compound is a compound of formula XXIX wherein Y is I. In another embodiment, the SARM compound is a compound of formula XXIX wherein Y is $CF_3$. In another embodiment, the SARM compound is a compound of formula XXIX wherein Y is Br. In another embodiment, the SARM compound is a compound of formula XXIX wherein Y is Cl. In another embodiment, the SARM compound is a compound of formula XXIX wherein Y is $SnR_3$. Each substituent of each of Y and Q for formula XXIX represents a separate embodiment of formula XXIX.

In another embodiment, the SARM compound is a compound represented by a structure of formula (XL):

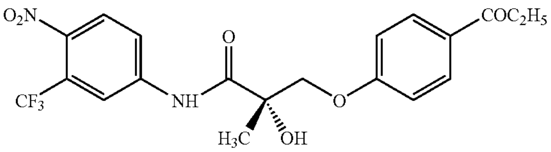

In another, embodiment, the SARM compound is a compound represented by a structure of formula (L):

L

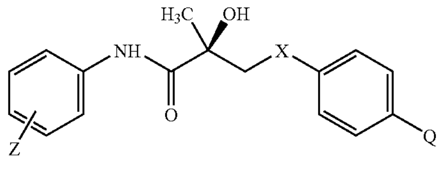

In another embodiment, the SARM compound is a compound of formula L wherein Q is F. In another embodiment, the SARM compound is a compound of formula L wherein Q is Cl. In another embodiment, the SARM compound is a compound of formula L wherein Q is Br. In another embodiment, the SARM compound is a compound of formula L wherein Q is I. In another embodiment, the SARM compound is a compound of formula L wherein Q is $NHCOCH_3$. In another embodiment, the SARM compound is a compound of formula L wherein Q is $NHCOCF_3$.

In another embodiment, the SARM compound is a compound of formula L wherein Z is $NO_2$. In another embodiment, the SARM compound is a compound of formula L wherein Z is CN. In another embodiment, the SARM compound is a compound of formula L wherein Z is COOH. In another embodiment, the SARM compound is a compound of formula L wherein Z is COR. In another embodiment, the SARM compound is a compound of formula L wherein Z is NHCOR. In another embodiment, the SARM compound is a compound of formula L wherein Z is CONHR. Each substituent of each of Z and Q for formula L represents a separate embodiment of formula L.

In another embodiment, the SARM compound is a compound represented by a structure of formula (LI):

LI

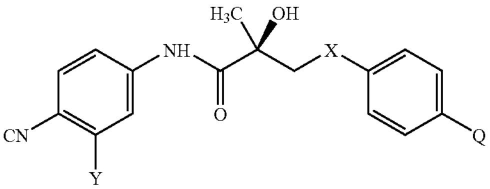

In another embodiment, the SARM compound is a compound of formula LI wherein Q is F. In another embodiment, the SARM compound is a compound of formula LI wherein Q is Cl. In another embodiment, the SARM compound is a compound of formula LI wherein Q is Br. In another embodiment, the SARM compound is a compound of formula LI wherein Q is I. In another embodiment, the SARM compound is a compound of formula LI wherein Q is $NHCOCH_3$. In another embodiment, the SARM compound is a compound of formula LI wherein Q is $NHCOCF_3$.

In another embodiment, the SARM compound is a compound of formula LI wherein Y is I. In another embodiment, the SARM compound is a compound of formula LI wherein Y is $CF_3$. In another embodiment, the SARM compound is a compound of formula LI wherein Y is Br. In another embodiment, the SARM compound is a compound of formula LI wherein Y is Cl. In another embodiment, the SARM compound is a compound of formula LI wherein Y is $SnR_3$. Each substituent of each of Y and Q for formula LI represents a separate embodiment of formula LI.

In another embodiment, the SARM compound is a compound represented by a structure of formula (LII):

LII

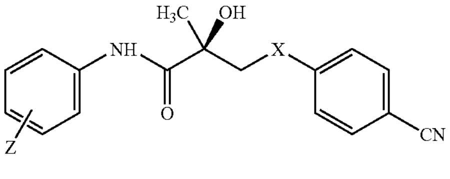

In another embodiment, the SARM compound is a compound of formula LII wherein Z is $NO_2$. In another embodiment, the SARM compound is a compound of formula LII wherein Z is CN. In another embodiment, the SARM compound is a compound of formula LII wherein Z is COOH. In another embodiment, the SARM compound is a compound of formula LII wherein Z is COR. In another embodiment, the SARM compound is a compound of formula LII wherein Z is NHCOR. In another embodiment, the SARM compound is a compound of formula LII wherein Z is CONHR. Each substituent of each of Z and Q for formula LII represents a separate embodiment of formula LII.

An "alkyl" group refers, in one embodiment, to a saturated aliphatic hydrocarbon, including straight chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from F, I, Br, Cl, hydroxy, alkoxy carbonyl, amido, alkylamido, dialkylamido, nitro, amino, alkylamino, dialkylamino, carboxyl, thio and thioalkyl.

An "alkenyl" group refers, in one embodiment, to an unsaturated hydrocarbon, including straight chain, branched chain and cyclic groups having one or more double bond. The alkenyl group may have one double bond, two double bonds, three double bonds etc. Examples of alkenyl groups are ethenyl, propenyl, butenyl, cyclohexenyl etc. The alkenyl group may be unsubstituted or substituted by one or more groups selected from F, I, Br, Cl, hydroxy, alkoxy carbonyl, amido, alkylamido, dialkylamido, nitro, amino, alkylamino, dialkylamino, carboxyl, thio and thioalkyl.

A "haloalkyl" group refers, in one embodiment, to an alkyl group as defined above, which is substituted by one or more halogen atoms, e.g. by F, Cl, Br or I.

An "aryl" group refers, in one embodiment, to an aromatic group having at least one carbocyclic aromatic group or heterocyclic aromatic group, which may be unsubstituted or substituted by one or more groups selected from F, I, Br, Cl, haloalkyl, hydroxy, alkoxy carbonyl, amido, alkylamido, dialkylamido, nitro, amino, alkylamino, dialkylamino, carboxy or thio or thioalkyl. Non-limiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers, in one embodiment, to an OH group. An "alkenyl" group refers to a group having at least one carbon-carbon double bond. A halo group refers, in one embodiment, to F, Cl, Br or I An "arylalkyl" group refers, in one embodiment, to an alkyl bound to an aryl, wherein alkyl and aryl are as defined above. An example of an arylalkyl group is a benzyl group Pharmaceutical Compositions "Pharmaceutical composition" means, in one embodiment, a therapeutically effective amount of the active ingredient, i.e. the SARM compound, together with a pharmaceutically acceptable carrier or diluent. A "therapeutically effective amount" refers, in one embodiment, to that amount which provides a therapeutic effect for a given condition and administration regimen.

The pharmaceutical compositions containing the SARM agent can be administered to a subject by any method known to a person skilled in the art, such as parenterally, paracancerally, transmucosally, transdermally, intra-muscularly, intravenously, intra-dermally, subcutaneously, intra-peritonealy, intra-ventricularly, intra-cranially, intra-vaginally or intra-tumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to the SARM active compound and the inert carrier or diluent, a hard gelating capsule.

Further, in another embodiment, the pharmaceutical compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intra-muscularly, and are thus formulated in a form suitable for intra-muscular administration.

Further, in another embodiment, the pharmaceutical compositions are administered topically to body surfaces, and are thus formulated in a form suitable for topical administration. Suitable topical formulations include gels, ointments, creams, lotions, drops and the like For topical administration, the SARM agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of SARM agent over a period of time.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intra-muscular injection) include sodium chloride solution, Ringer's dextrose, dextrose and sodium chloride, lactated Ringer's and fixed oils. Intravenous vehicles include fluid and nutrient replenishers, electrolyte replenisliers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled release compositions, i.e. compositions in which the SARM compound is released over a period of time after administration. Controlled or sustained release compositions include formulation in lipophilic depots (e.g. fatty acids, waxes, oils). In another embodiment, the composition is an immediate release composition, i.e. a composition in which all of the SARM compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, micro-emulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions that contain an active component is well understood in the art, for example by mixing, granulating, or tablet-forming processes. The active therapeutic ingredient is often mixed with excipients that are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary, methods into suitable forms for administration, such as tablets, coated tablets, hard or soft gelatin capsules, aqueous, alcoholic or oily solutions. For parenteral administration, the SARM agents or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

As used herein, the term "administering" refers to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

In another embodiment, the term "contacting" means that the SARM compound of the present invention is introduced into a subject receiving treatment, and the SARM compound is allowed to come in contact with the AR in vivo.

In one embodiment, the methods of the present invention comprise administering a SARM compound as the sole active ingredient. However, also encompassed within the scope of the present invention are methods for treating and/or preventing bone-related disorders, which comprise administering the SARM compounds in combination with one or more therapeutic agents. These agents include, but are not limited to: LHRH analogs, reversible anti-androgens, anti-estrogens, anticancer drugs, 5-alpha reductase inhibitors, aromatase inhibitors, progestins, agents acting through other nuclear hormone receptors, selective estrogen receptor modulators (SERM), progesterone, estrogen, PDE5 inhibitors, apomorphine, bisphosphonate, and one or more additional SARMS.

Thus, in one embodiment, the methods of the present invention comprise administering the SARM compound in combination with an LHRH analog. In another embodiment, the methods of the present invention comprise administering a SARM compound in combination with a reversible anti-androgen. In another embodiment, the methods of the present invention comprise administering a SARM compound in combination with an anti-estrogen. In another embodiment, the methods of the present invention comprise administering a SARM compound in combination with an anticancer drug. In another embodiment, the methods of the present invention comprise administering a SARM compound in combination with a 5-alpha reductase inhibitor. In another embodiment, the methods of the present invention comprise administering a SARM compound in combination with an aromatase inhibitor. In another embodiment, the methods of the present invention comprise administering a SARM compound in combination with a progestin. In another embodiment, the methods of the present invention comprise administering a SARM compound in combination with an agent acting through other nuclear hormone receptors. In another embodiment, the methods of the present invention comprise administering a SARM compound in combination with a selective estrogen receptor modulator (SERM). In another embodiment, the methods of the present invention comprise administering a SARM compound in combination with a progesterone. In another embodiment, the methods of the present invention comprise administering a SARM compound in combination with an estrogen. In another embodiment, the methods of the present invention comprise administering a SARM compound in combination with a PDE5 inhibitor. In another embodiment, the methods of the present invention comprise administering a SARM compound in combination with apomorphine. In another embodiment, the methods of the present invention comprise administering a SARM compound in combination with a bisphosphonate. In another embodiment, the methods of the present invention comprise administering a SARM compound, in combination with one or more additional SARMS.

The following examples are presented in order to more fully illustrate the preferred embodiments of the invention. They should in no way be construed, however, as limiting the broad scope of the invention

EXPERIMENTAL DETAILS SECTION

Example 1

Synthesis of SARM Compounds

The synthesis of Compound VIII is described in below. The synthesis of Compound XI is described concurrently, although different starting materials were used, as described in the following paragraphs.

Step 1: Synthesis of (2R)-1-Methacryloylpyrrolidin-2-carboxylic Acid (Precursor Compound A)

D-Proline (14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2N NaOH solution (71 mL) were simultaneously added over 40 min to the aqueous solution of D-proline in an ice bath. The temperature of the mixture was kept at 10-11° C. during the addition of the metacryloly chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite, and evaporated in vacuo to give the crude product as a colorless oil. Recrystallization of the oil from ethyl ether and hexanes afforded 16.2 (68%) of the desired compound as colorless crystals: mp 102-103° C. (lit. [214] mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$)δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C═O), 1647 (CO, COOH), 1584, 1508, 1459, 1369, 1348, 1178 $cm^{-1}$; $[\alpha]_D^{26}$+80.8° (c=1, MeOH); Anal. Calcd. for $C_9H_{13}NO_3$: C, 59.00; H, 7.15; N, 7.65. Found: C 59.13; H, 7.19; N, 7.61.

Step 2: Synthesis of (3R,8aR)-3-Bromomethyl-3-methyl-tetrahydro-pyrrolo[2,1c][1,4]oxazine-1,4-dione (Precursor compound B)

A solution of NBS (23.5 g, 0.132 mol) in 100 mL of DMF was added dropwise to a stirred solution of (Compound A) (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152-154° C. (lit. [214] mp 107-109° C. for the S-isomer); $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, $CHH_a$), 3.86 (d, J=11.4 Hz, 1H, $CHH_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C═O), 1687 (C═O), 1448, 1377, 1360, 1308, 1227, 1159, 1062 $cm^{-1}$; $[\alpha]_D^{26}$+124.5° (c=1.3, chloroform); Anal. Calcd. for $C_9H_{12}BrNO_3$: C; 41.24; H, 4.61; N, 5.34. Found: C 41.46, H 4.64, N 5.32.

Step 3: Synthesis of (2R)-3-Bromo-2-hydroxy-2-methylpropanoic Acid (Compound #1 in FIG. 1)

A mixture of bromolactone (Compound B) (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite, and evaporated in vacuo to dryness. Recrystallization from toluene afforded 10.2 g (86%) of the desired compound as colorless crystals: mp 107-109° C. (lit. [214] mp 109-113° C. for the S-isomer); $^1H$ NMR (300 MHz, DMSO-$d_6$) δ 3.63 (d, J=10.1 Hz, 1H, $CHH_a$), 3.52 (d,J=10.1 Hz, 1H, $CHH_b$), 1.35 (s, 3H, Me); IR (KBr) 3434 (OH), 3300-2500 (COOH), 1730 (C═O), 1449, 1421, 1380, 1292, 1193, 1085 $cm^{-1}$; $[\alpha]_D^{26}$+10.5° (c=2.6, MeOH); Anal. Calculated. for $C_4H_7BrO_3$: C 26.25, H 3.86. Found: C 26.28, H 3.75.

Step 4: Synthesis of N-[4-Nitro-3-(trifluoromethyl) phenyl]-(2R)-3-bromo-2-hydroxy-2-methylpropanamide (Compound #4 in FIG. 1).

Thionyl chloride (8.6 g, 72 mmol) was added dropwise under argon to a solution of bromoacid (compound #1 in FIG. 1) (11.0 g, 60 mmol) in 70 mL of dimethyl acetamide (DMA) at −5 to −10° C. (For the synthesis of Compound XI, tetrahydrofuran (THF) was used in place of DMA). The resulting mixture was stirred for 2 h under the same conditions to yield compound #2 of FIG. 1. A solution of 4-nitro-3-trifluoromethyl-aniline (compound #3 in FIG. 1; 12.4 g, 60 mmol) in 80 mL of DMA was added dropwise to the above solution, and the resulting mixture was stirred overnight at room temperature. (For the synthesis of Compound XI, a mixture of tetrylammonium bromide (TEA) and THF was used in place of DMA). The solvent was removed on Rotavapor using high vacuum oil pump; the residue was diluted with saturated $NaHCO_3$ solution, and extracted with ethyl ether (100 mL×3). Combined extracts were dried over anhydrous $Na_2SO_4$, filtered through Celite, and purified by flash chromatography on silica gel, using methylene chloride as eluent to afford 18.0 g (80%) of the desired compound: mp 98-100° C. ($R_f$=0.2, silica gel, $CH_2Cl_2$); $^1H$ NMR (300 MHz, DMSO-$d_6$) δ 10.54 (s, 1H, NH), 8.54 (d, J=2.1 Hz, 1H, ArH), 8.34 (dd, J=9.0 Hz, J=2.1 Hz, 1H, ArH), 8.18 (d, J=9.0 Hz, 1H, ArH), 637 (s, 1H, OH), 3.82 (d, J=10.4 Hz, 1H, $CHH_a$), 3.58 (d, J=10.4 Hz, 1H, $CHH_b$), 1.48 (s, 3H, Me); $^{13}C$ NMR (75 MHz, DMSO-$d_6$) δ 173.6 (C═O), 143.0, 127.2, 123.2, 122.6 (q, J=33.0 Hz), 122.0 (q, J=271.5 Hz), 118.3 (q, J=6.0 Hz), 74.4, 41.4, 24.9; IR (KBr) 3344 (OH), 1680 (C═O), 1599, 1548 (C═C, Ar), 1427, 1363, 1161 $cm^{-1}$; MS (ESI): m/z 370.8 $(M)^+$; Anal. Calculated for $C_{11}H_{10}BrN_2O_4$: C, 35.60, H 2.72, N 7.55. Found: C 35.68; H, 2.72, N 7.49.

Step 5: N-[4-nitro-3-trifluoromethyl)phenyl]-(2S)-3-[4-(acetylamino) phenoxy]-2-hydroxy-2-methylpropanamide (Compound VIII; compound #6 in FIG. 1).

Compound VIII was prepared from compound #4 as follows: Compound #4 (0.37 g, 1.0 mmol), 4-acetamidophenol (0.23 g, 1.5 mmol), $K_2CO_3$ (0.28 g, 2.0 mmol), and 10% of benzyltributylammonium chloride as a phase transfer catalyst in 20 mL of methyl ethyl ketone were heated at reflux overnight under argon. In this reaction, bromohydrin was converted to an epoxide, and the epoxide opened to give the same desired ether product. (For the synthesis of Compound XI, this reaction was performed in two steps: in the first step, the epoxide was formed using acetone as the solvent. Then, the displacement reaction was performed using butanone as the solvent). The reaction was followed by thin-layer chromatography (TLC), and the resulting mixture was filtered through Celite and concentrated in vacuo to dryness. Purification by flash column chromatography on silica gel (hexanes-ethyl acetate, 3:1) yielded 0.38 g (86%) ($R_f$=0.18 hexanes-ethyl acetate, 3:1) of the desired compound as a light yellow powder: mp 70-74° C.; The solid can be recrystalized from ethyl acetate and hexane); $^1H$ NMR (300 MHz, DMSO-$d_6$) δ 10.62 (s, 1H, NH), 9.75 (s, 1H, NH), 8.56 (d, J=1.9 Hz, 1H, ArH), 8.36 (dd, J=9.1 Hz, J=1.9 Hz, 1H, ArH), 8.18 (d, J=9.1 Hz, 1H, ArH), 7.45-7.42 (m, 2H, ArH), 6.85-6.82 (m, 2H, ArH), 6.25 (s, 1H, OH), 4.17 (d, J=9.5 Hz, 1H, $CHH_a$), 3.94 (d, J=9.5 Hz, 1H, $CHH_b$), 1.98 (s, 3H, Me), 1.43 (s, 3H, Me); $^{13}C$ NMR (75 MHz, DMSO-$d_6$) δ 174.6 (C═O), 167.7, 154.2, 143.3, 141.6, 132.8, 127.4, 123.0, 122.7 (q, J=33.0 Hz), 122.1 (q, J=271.5 Hz), 120.1, 118.3 (q, J=6.0 Hz), 114.6, 74.9, 73.8, 23.8, 23.0; IR (KBr) 3364 (OH), 1668 (C═O), 1599, 1512 (C═C, Ar), 1457, 1415, 1351, 1323, 1239, 1150 1046 $cm^{-1}$; MS (ESI): m/z 464.1 $(M+Na)^+$; Anal. Calculated for $C_{19}H_{18}F_3N_3O_6$: C 51.71, H 4.11, N 9.52. Found: C 52.33, H 4.40, N 9.01.

The synthesis of the various SARM compounds was accomplished using variations of the reaction scheme described. For example, to synthesize SARM compounds containing para-CN, meta-trifluoromethyl substituents on the A ring, such as Compounds IV, XI, and XIII, 4-cyano-3-trifluoromethyl-aniline was utilized in place of 4-nitro-3-trifluoromethyl-aniline.

Bromo-intermediates were used which allowed various phenolic compounds to displace the bromide to give the desired ether product. For example, to synthesize SARM compounds containing a para-F substituent on the B ring, such as Compounds IX and XI, 4-fluorophenol was utilized in place of 4-acetamidophenol.

Figure 2:
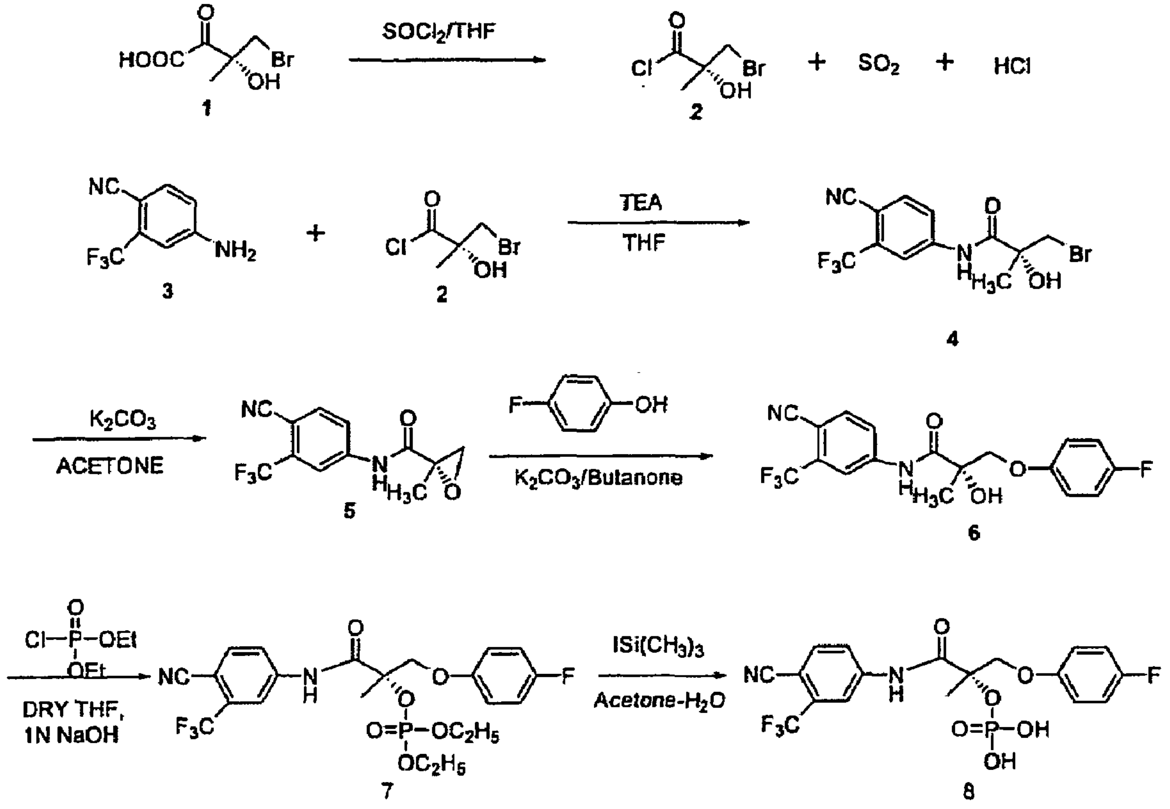
FIG. 2: Synthesis scheme of a Compound XI and its prodrug.

For example, the synthesis of Compound XI is depicted in FIG. 2 (steps 1-6).

Example 2

Synthesis of SARM Pro-Drugs

SARM compounds were used as starting point to synthesize phosphoric acid ester-modified and phosphoric acid-diethyl ester-modified prodrugs. The following protocol describes the preparation of SARM prodrugs from Compound XI. The protocol is generalizable, however, to all SARM compounds of the present invention.

Phosphoric acid 1-(4-cyano-3-trifluoromethyl-phenylcarbamoyl)-2-(4-fluoro-phenoxy)-1-methyl-ethyl ester diethyl ester (structure 7 in FIG. 2) was synthesized as follows: To a stirred mixture of N-(4-Cyano-3-trifluorometllyl-phenyl)-3-(4-fluoro-phenoxy)-2-hydroxy-2-methyl-propionamide (structure 6; Compound XI; 1.792 g, 4.6872 mmol) in anhydrous THF (10 mL) and 1N NaOH/THF (18.2 mL), under argon atmosphere, was added dropwise a solution of diethyl chlorophosphate (5.4 mL, 37.5 mmol) in THF (25 mL) over 30 min. The reaction mixture was stirred overnight (15 h) at room temperature and to this, was added 2N NaOH aqueous solution. The obtained clear solution was stirred at room temperature for 30 min. Ethyl acetate was added to the reaction mixture, and the phases were separated. The organic phase was washed with 0.1N NaOH, and the combined aqueous phases were brought to pH 5 and extracted with ethyl acetate. The collected organic phases were washed with water and dried over anhydrous $Na_2SO_4$. The solvent was removed under vacuum, and the crude residue was purified by flash chromatography using 10%-50% EtOAc/Hexane to obtain Phosphoric acid 1-(4-cyano-3-trifluoromethyl-phenylcarbamoyl)-2-(4-fluoro-phenoxy)-1-methyl-ethyl ester diethyl ester (structure 7 in FIG. 2) as an oily mass (1.495 g, 61.5%). $^1$H NMR(500 MHz, DMSO-$d_6$) δ 10.42 (s, 1H, NH), 8.38 (d, J=1.5 Hz, 1H, ArH), 8.24 (d, J=8.5 Hz, 1H, ArH), 8.15 (d, J=9.0 Hz, 1H, ArH), 7.13-7.09 (m, 2H, ArH), 6.97-6.95 (m, 2H, ArH), 4.46 (d, J=10.5 Hz, 1H, —$CH_2$), 4.41 (d, J=10.5 Hz, 1H, —$CH_2$), 4.13-4.02 (m, 4H, 2*—$CH_2$), 1.77 (s, 3H, —$CH_3$), 1.22 (t, J=7 Hz, 7 Hz, 3H, —$CH_3$), Phosphoric acid mono-[1-(4-cyano-3-trifluoromethyl-phenylcarbamoyl)-2-(4-fluoro-phenoxy)-1-methyl-ethyl]ester (structure 8 in FIG. 2) was synthesized from structure 7 as follows: To a stirred cold solution of structure 7 (0.353 g, 0.6809 mmol) in anhydrous methylene chloride (10 mL), was added dropwise iodotrimethylsilane (0.817 g, 4.0854 mmol) under a argon atmosphere and at 0° C. The mixture was stirred for 1 h at 0° C. and for 1 h at room temperature. The solvent was eliminated under vacuum, and the residue was cooled to 0° C. and treated with a mixture of acetone (25 mL) and $H_2O$ (1 mL) to hydrolyse the intermediate silyl ester. After stirring at 0° C. for 1 h, the reaction mixture was stirred at room temperature overnight (16 hours). The solvent was removed under vacuum, and the residue was extracted with ethyl acetate and dried over anhydrous $Na_2SO_4$. Solvents were removed under vacuum and the residue was treated with methylene chloride (10 mL) and the solvents again removed under vacuum to obtain Phosphoric acid mono-[1-(4-cyano-3-trifluoromethyl-phenylcarbamoyl)-2-(4-fluoro-phenoxy)-1-methyl-ethyl] ester (structure 8; 0.309 g, 98%) as a dark red solid. $^1$H NMR(300 MHz, DMSO-$d_6$) δ 11.60-11.59 (bs, 2H, OH), 10.59 (s, 1H, NH), 8.36 (s, 1H, ArH), 8.19-8.11 (m, 2H, ArH), 7.12-7.06 (m, 2H, ArH), 6.96-6.92 (m, 2H, ArH), 4.39 (d, J=9.6 Hz, 1H, —$CH_2$), 4.27 (d, J=9.9 Hz, 1H, —$CH_2$) & 1.74 (s, 3H, —$CH_3$). Mass (ESI) m/z: 462 $(M-H)^+$, 461.

Example 3

SARM Compounds Exhibit a Higher Ratio of Anabolic to Androgenic Activity than Testosterone The SARM compounds described herein and their prodrugs were designed, synthesized and evaluated for in-vitro and in-vivo pharmacologic activity. The in-vitro androgen receptor binding affinity and ability to maintain androgen dependent tissue growth in castrated animals was studied. Androgenic activity was monitored as the ability of the SARM compounds to maintain and/or stimulate the growth of the prostate and seminal vesicles, as measured by weight. Anabolic activity was monitored as the ability of the SARM compounds to maintain and/or stimulate the growth of the levator ani muscle, as measured by weight.

The in-vitro activity of the SARM compounds, specifically Compound VIII, demonstrated high androgen receptor binding affinity ($K_i$=7.5 nM). Animal studies with the SARM compounds, specifically Compound VIII, demonstrated that it is a potent androgenic and anabolic nonsteroidal agent. Four groups of rats were used for these studies: (1) intact controls, (2) castrated controls, (3) castrated animals treated with testosterone propionate (100 μg/day), and (4) castrated animals treated with Compound VIII (1000 μg/day). Testosterone and Compound VIII were delivered at a constant rate for 14 days via subcutaneous osmotic pumps.

Figure 3:
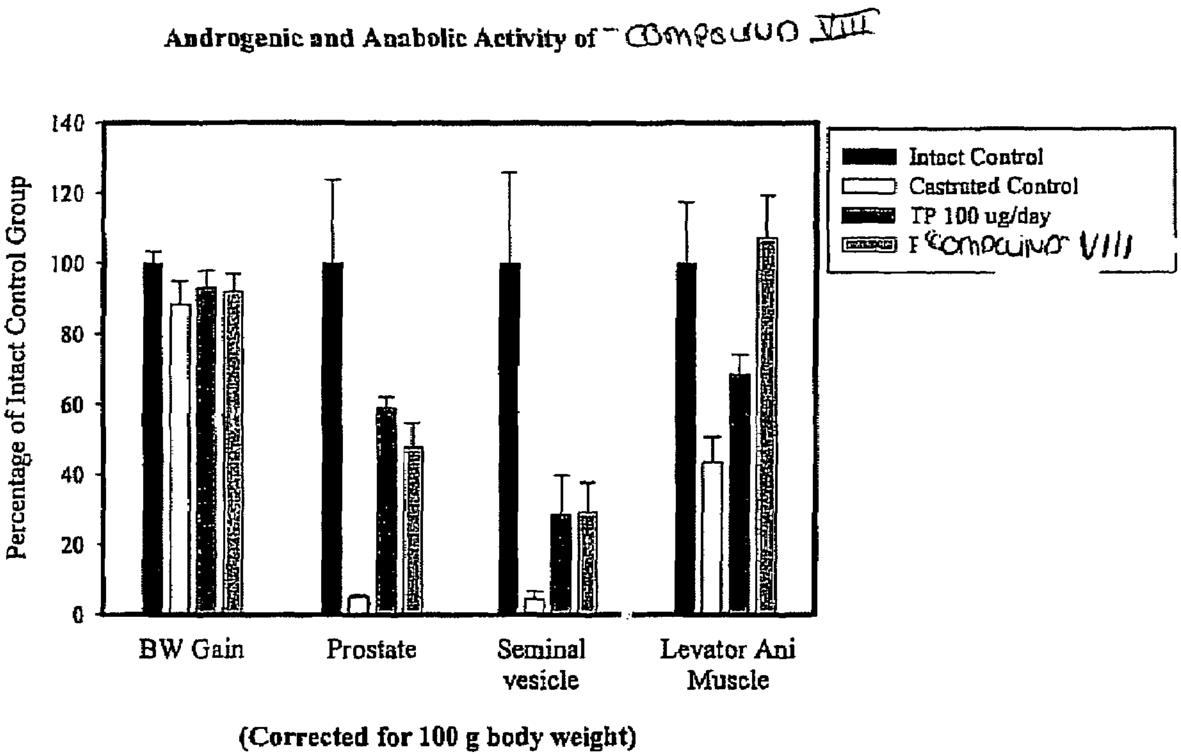
FIG. 3: Androgenic and Anabolic activity of Compound VIII Rats were left untreated (intact control), castrated (castrated control), treated with testosterone propionate (TP), or treated with Compound VIII, and the body weight gain as well as the weight of androgen-responsive tissues (prostate, semimal vesicles and levator ani muscle) was determined.

The results of these studies are shown in FIG. 3. Castration significantly reduced the weight of androgenic (e.g., prostate and seminal vesicles) and anabolic (e.g., levator ani muscle) tissues, but had little effect on animal body weight (BW). Treatment of castrated animals with testosterone propionate or Compound VIII maintained the weight of androgenic tissues to the same degree. Compound VIII had similar androgenic activity as testosterone propionate (i.e., the prostate and seminal vesicle weights were the same), but much greater efficacy as an anabolic agent. Compound VIII showed greater anabolic activity than testosterone propionate at the doses tested (i.e., the levator ani muscle maintained the same weight as intact control animals and was greater than that observed for testosterone).

These findings demonstrate tissue-selective androgenic and anabolic activity (i.e., differing androgenic and anabolic potency) of SARM compounds for the androgen receptor.

Example 4

Selective Anabolic Activity is a General Property of SARMs

The in-vivo efficacy and acute toxicity of four novel nonsteroidal androgens (Compounds IX, VIII, XXI and XL) was examined. In-vitro assays established that these compounds bind the androgen receptor with high affinity. The structures and names of the four compounds are presented below:

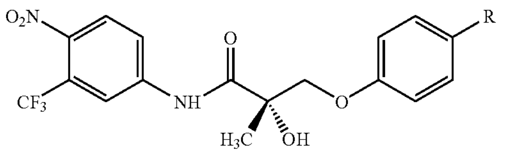

Compound IX R = F
Compound VIII R = $NHCOCH_3$
Compound XXI R = $COCH_3$
Compound XL R = $COC_2H_5$

Experimental Methods

Materias. The S-isomers of Compounds IX, VIII, XXI and XL and the R-isomer of Compound IX were synthesized as described in Example 1. Testosterone propionate (TP), polyethylene glycol 300 (PEG300, reagent grade) and neutral buffered formalin (10% w/v) were purchased from Sigma Chemical Company (St Louis, Mo.). Alzet osmotic pumps (model 2002) were purchased from Alza Corp. (Palo Alto, Calif.).

Animals. Immature male Sprague-Dawley rats, weighing 90 to 100 g, were purchased from Harlan Biosciences (Indianapolis, Ind.) The animals were maintained on a 12-hour light-dark cycle with food and water available ad libitum. The animal protocol was reviewed and approved by the Institutional Laboratory Animal Care and Use Committee.

Study Design. Rats were randomly distributed into twenty-nine (29) groups, with 5 animals per group. Treatment groups are described in Table 1. One day prior to the start of drug treatment, animals in groups 2 through 29 were individually removed from the cage, weighed and anesthetized with an intraperitoneal dose of ketamine/xylazine (87/13 mg/kg; approximately 1 mL per kg). When appropriately anesthetized (i.e., no response to toe pinch), the animals' ears were marked for identification purposes. Animals were then placed on a sterile pad and their abdomen and scrotum washed with betadine and 70% alcohol. The testes were removed via a midline scrotal incision, with sterile suture being used to ligate supra-testicular tissue prior to surgical removal of each testis. The surgical wound site was closed with sterile stainless steel wound clips, and the site cleaned with betadine. The animals were allowed to recover on a sterile pad (until able to stand) and then returned to their cage.

TABLE 1

Animals Groups and Experimental Design

| Group # | Castrated? | Drug | Dose | # of animals |
|---|---|---|---|---|
| 1 | No | None | None | 5 |
| 2 | Yes | None | Vehicle only | 5 |
| 3 | Yes | Testosterone | 0.1 mg/day | 5 |
| 4 | Yes | Testosterone | 0.3 mg/day | 5 |
| 5 | Yes | Testosterone | 0.5 mg/day | 5 |
| 6 | Yes | Testosterone | 0.75 mg/day | 5 |
| 7 | Yes | Testosterone | 1.0 mg/day | 5 |
| 8 | Yes | R-IX | 1.0 mg/day | 5 |
| 9 | Yes | S-IX | 0.1 mg/day | 5 |
| 10 | Yes | S-IX | 0.3 mg/day | 5 |
| 11 | Yes | S-IX | 0.5 mg/day | 5 |
| 12 | Yes | S-IX | 0.75 mg/day | 5 |
| 13 | Yes | S-IX | 1.0 mg/day | 5 |
| 14 | Yes | S-XXI | 0.1 mg/day | 5 |
| 15 | Yes | S-XXI | 0.3 mg/day | 5 |
| 16 | Yes | S-XXI | 0.5 mg/day | 5 |
| 17 | Yes | S-XXI | 0.75 mg/day | 5 |
| 18 | Yes | S-XXI | 1.0 mg/day | 5 |
| 19 | Yes | S-XL | 0.1 mg/day | 5 |
| 20 | Yes | S-XL | 0.3 mg/day | 5 |
| 21 | Yes | S-XL | 0.5 mg/day | 5 |
| 22 | Yes | S-XL | 0.75 mg/day | 5 |
| 23 | Yes | S-XL | 1.0 mg/day | 5 |
| 24 | Yes | S-VIII | 0.1 mg/day | 5 |
| 25 | Yes | S-VIII | 0.3 mg/day | 5 |
| 26 | Yes | S-VIII | 0.5 mg/day | 5 |
| 27 | Yes | S-VIII | 0.75 mg/day | 5 |
| 28 | Yes | S-VIII | 1.0 mg/day | 5 |
| 29 | Yes | None | Vehicle only | 5 |

Twenty-four hours later, animals in groups 2 through 29 were re-anesthetized with ketamine/xylazine, and an Alzet osmotic pump(s) (model 2002) was placed subcutaneouly in the scapular region. In this instance, the scapular region was shaved and cleaned (betadine and alcohol) and a small incision (1 cm) made using a sterile scalpel. The osmotic pump was inserted and the wound closed with a sterile stainless steel wound clip. Animals were allowed to recover and were returned to their cage. Osmotic pumps contained the appropriate treatment (designated in Table 1) dissolved in polyethylene glycol 300 (PEG300). Osmotic pumps were filled with the appropriate solution one day prior to implantation. Animals were monitored daily for signs of acute toxicity to drug treatment (e.g., lethargy, rough coat).

After 14 days of drug treatment, rats were anesthetized with ketamine/xylazine. Animals were then sacrificed by exsanguinations under anesthesia. A blood sample was collected by venipuncture of the abdominal aorta, and submitted for complete blood cell analysis. A portion of the blood was placed in a separate tube, centrifuged at 12,000 g for 1 minute, and the plasma layer removed and frozen at −20° C. The ventral prostates, seminal vesicles, levator ani muscle, liver, kidneys, spleen, lungs, and heart were removed, cleared of extraneous tissue, weighed, and placed in vials containing 10% neutral buffered formalin. Preserved tissues were sent to GTx, Inc. for histopathological analysis.

For data analysis, the weights of all organs were normalized to body weight, and analyzed for any statistical significant difference by single-factor ANOVA. The weights of prostate and seminal vesicle were used as indexes for evaluation of androgenic activity, and the levator ani muscle weight was used to evaluate the anabolic activity.

Results

The androgenic and anabolic activities of the S isomers of Compounds IX, VIII, XXI and XL, and the R isomer of compound IX were examined in a castrated rat model after 14 days of administration. Testosterone propionate, at increasing doses, was used as the positive control of anabolic and androgenic effects.

Figure 4:
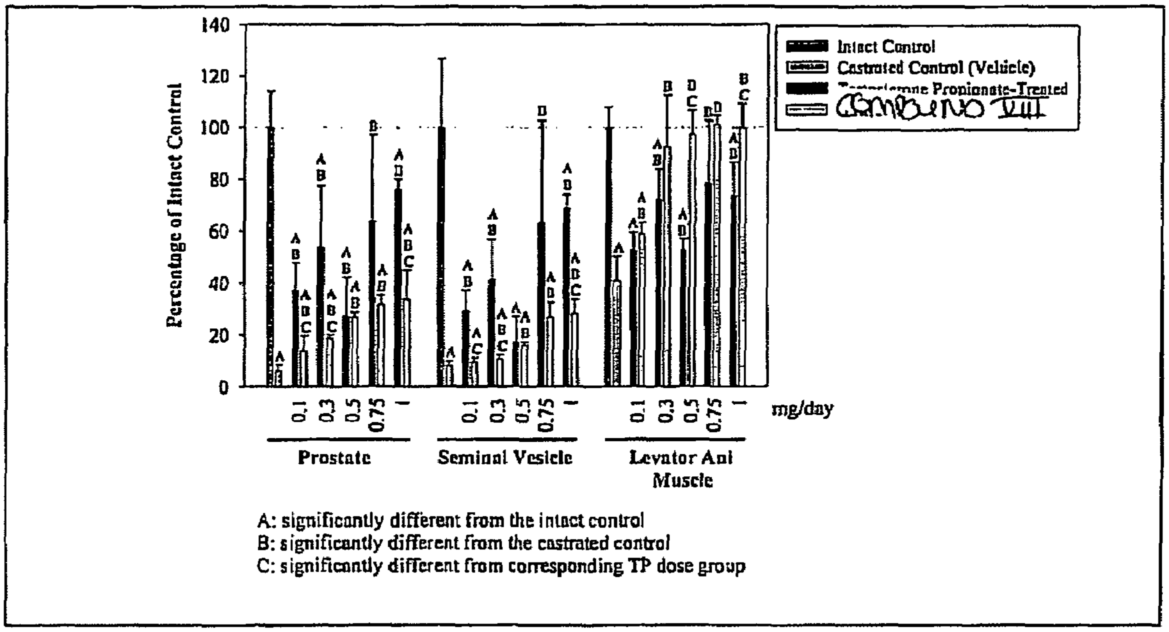
FIG. 4: Androgenic and Anabolic activity of Compound VIII. Rats were left untreated (intact control), castrated (castrated control), treated with 0.1, 0.3, 0.5, 0.75 and 1.0 mg/day TP, or treated with 0.1, 0.3, 0.5, 0.75 and 1.0 mg/day Compound VIII, and the weight of androgen-responsive tissues (prostate, semimal vesicles and levator ani muscle) was determined.
Figure 5:
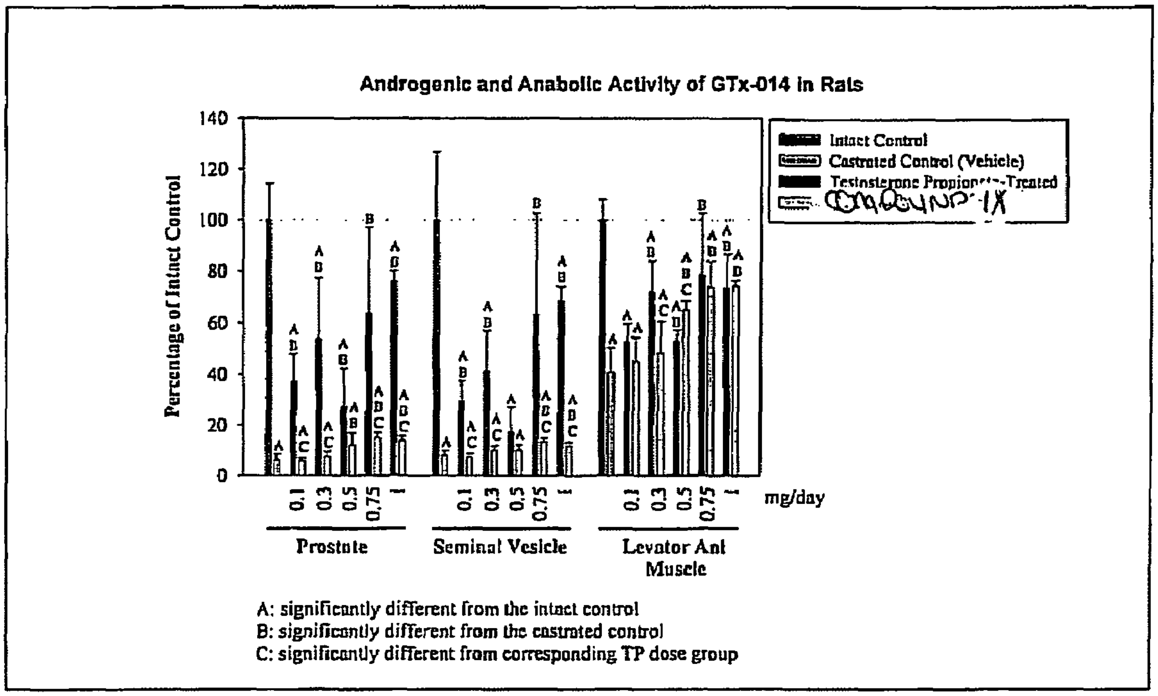
FIG. 5: Androgenic and Anabolic activity of Compound IX. Rats were left untreated (intact control), castrated (castrated control), treated with 0.1, 0.3, 0.5, 0.75 and 1.0 mg/day TP, or treated with 0.1, 0.3, 0.5, 0.75 and 1.0 mg/day Compound III, and the weight of androgen-responsive tissues (prostate, semimal vesicles and levator ani muscle) was determined.

As shown in FIGS. 4 and 5, the weights of prostate, seminal vesicle, and levator ani muscle in castrated, vehicle-treated rats decreased significantly, due to the ablation of endogenous androgen production. Exogenous administration of testosterone propionate, an androgenic and anabolic steroid, increased the weights of prostate, seminal vesicle, and levator ani muscle in castrated rats in a dose-dependent manner. The R-isomer of compound IX, and S-isomers of compounds XXI and XL showed no effect on the weights of prostate, seminal vesicle, and levator ani muscle in castrated animals (data not shown). Administration of the S-isomers of Compound VIII (FIG. 4) and Compound IX (FIG. 5) resulted in dose-dependent increases in prostate, seminal vesicle and levator ani muscle weights. Compared with testosterone propionate, Compound VIII exhibited a greater potency and intrinsic activity in increasing the weight of levator ani muscle, while having a lower potency and intrinsic activity in increasing the weights of prostate and seminal vesicle. At a dose as low as 0.3 mg/day, Compound VIII was able to maintain the levator ani muscle weight of castrated animals at the level of intact animals.

Compound IX exhibited even greater tissue selectivity than Compound VIII, while being slightly less potent overall (compare effects on the prostate and seminal vesicles in FIGS. 4 and 5). Similar to Compound VIII, Compound IX significantly increased levator ani muscle weights without stimulate prostate and seminal vesicle growth (i.e., the prostate and seminal vesicle weights were less than 20% of that observed in intact animals or in animals treated with testosterone propionate).

Thus, selective stimulation of the AR in anabolic tissue (relative to the AR stimulation in androgenic tissues) is a general property of SARMS, and is not particular to Compound VIII.

In addition, none of the SARM compounds had significant effects on body weight or the weights of other organs (i.e., liver, kidneys, spleen, lungs and heart). Nor did any compound produce any signs of acute toxicity, as gauged by diagnostic hematology tests and visual examination of animals receiving treatments. Importantly, Compound VIII did not suppress the production of luteinizing hormone (LH) or follicle stimulating hormone (FSH) at a dose of 0.5 mg/day (i.e., a dose that exhibited maximal anabolic effects), as shown in Tables 2-3:

TABLE 2

| Effect of Compound VIII and TP on Plasma FSH levels. | | |
|---|---|---|
| Control | Compound VIII (0.5 mg/day) | TP (0.5 mg/day) |
| 68.6 ± 6.3 †‡ | 69.6 ± 11.7 †‡ | 58.0 ± 6.9 *†‡ |

TABLE 3

| Effect of Compound VIII and TP on Plasma LH levels. | | |
|---|---|---|
| Control | Compound XXI (0.5 mg/day) | TP (0.5 mg/day) |
| 8.704 ± 1.709 †‡ | 8.644 ± 2.799 †‡ | 6.702 ± 1.513 †‡ |

* $p < 0.05$ compared to control group.
† $p < 0.05$ compared to intact group.
‡ $p < 0.05$ compared to hemi-orchidectomized group.

In summary, Compounds VIII and IX exhibited anabolic activity, maintaining the weight of levator ani muscle after removal of endogenous androgen. Selectivity of the anabolic activity was greater than testosterone propionate. In addition, Compound IV does not suppress FSH levels at doses that are capable of eliciting maximal stimulation of levator ani muscle growth. Thus, SARMS have therapeutic applications in males and females for modulation of fertility, erythropoiesis, osteoporosis, sexual libido and in men with or at high risk for prostate cancer.

Example 5

Pharmacokinetics of Compound VIII in Dogs

Figure 6:
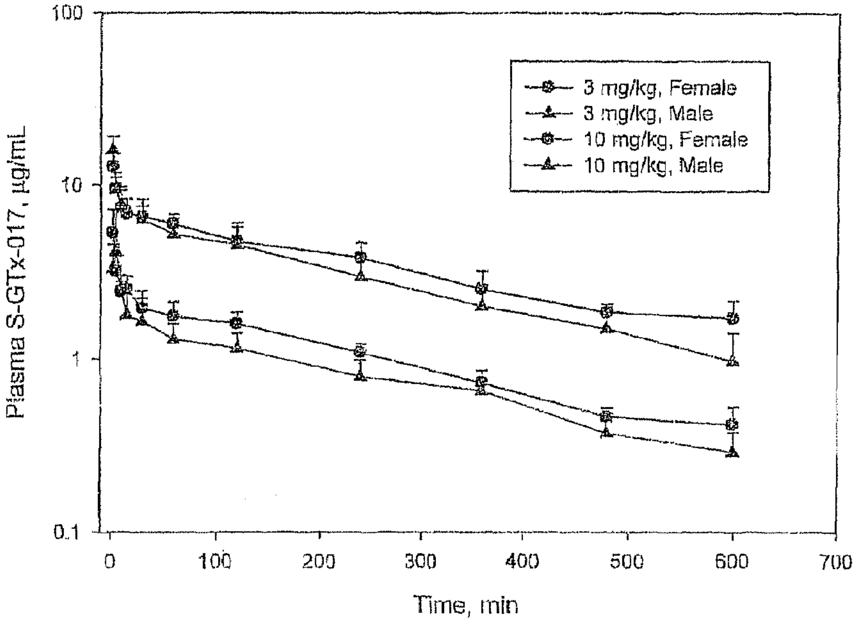
FIG. 6: Average plasma concentration-time profiles of Compound VIII in beagle dogs after IV administration at 3 and 10 mg/kg.
Figure 7:
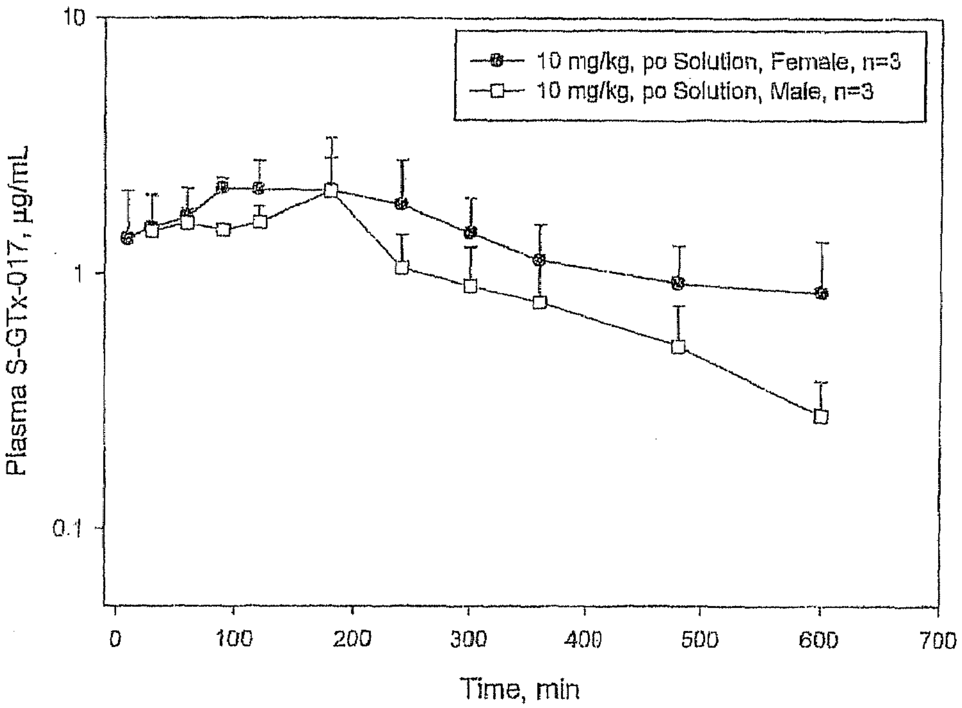
FIG. 7: Average plasma concentration-time profiles of Compound VIII in beagle dogs after PO administration as solution at 10 mg/kg.
Figure 8:
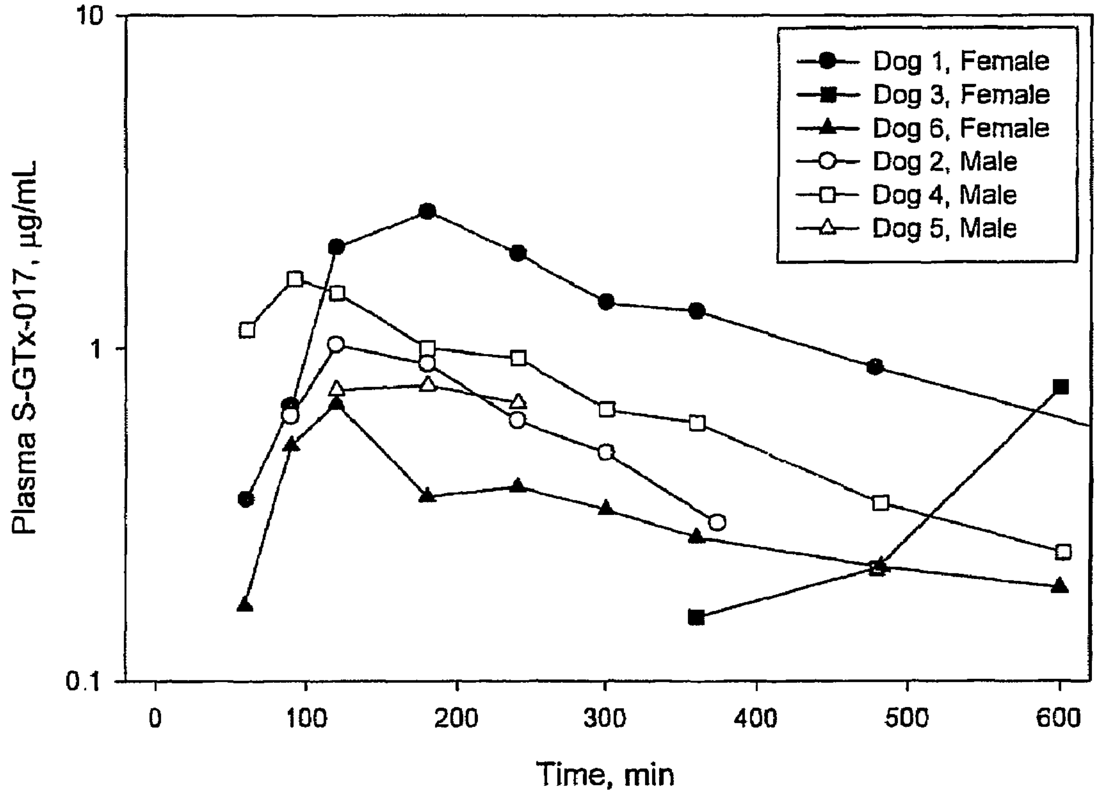
FIG. 8: Average plasma concentration-time profiles of Compound VIII in beagle dogs after IV administration as capsules at mg/kg.

The pharmacokinetics of S-Compound VIII were characterized in beagle dogs. A four-treatment, four-period crossover design was utilized in the study, which involved a total of six beagle dogs, three of each gender. Each animal received a 3 mg/kg IV dose, a 10 mg/kg IV dose, a 10 mg/kg PO dose in solution, and a 10 mg/kg PO dose in capsule, in a randomly assigned order. There was a one-week washout period between treatments. Plasma samples were collected for up to 72 hr after drug administration. Plasma Compound VIII concentrations were analyzed by a validated HPLC method The clearance (CL), volume of distribution (Vss), half-life ($T_{1/2}$), and other pharmacokinetic parameters were determined by noncompartmental methods. Results showed that Compound VIII was cleared from dog plasma with a terminal $T_{1/2}$ of about 4 hr and a CL of 4.4 mL/min/kg after IV administration. FIGS. 6, 7, and 8 show the plasma concentration-time profiles of Compound VIII after administration of an intravenous solution, oral solution, and oral capsule, respectively. The pharmacokinetics were dose- and gender-independent. The oral bioavailability of Compound VIII varied with the dosage form, and averaged 38% and 19% for solution and capsule, respectively. Thus, Compound VIII demonstrated moderate half-life, slow clearance and moderate bioavailability in beagle dogs, identifying it as the first of a new class of orally bioavailable tissue-selective androgen receptor modulators.

Example 6

Compound VIII Analysis by HPLC

A reversed phase high pressure liquid chromatograph (HPLC) assay was developed to quantitate Compound VIII concentrations in dog plasma. Dog blood samples were obtained by venipuncture and centrifuged at 1000 g for 15 minutes. Samples were stored frozen at −20° C. until analysis. Individual samples were rapidly thawed and an aliquot (0.5 ml) was spiked with internal standard (20 µl of a 200 µg/ml aqueous solution of CM-II-87). An aliquot of 1 ml of acetonitrile was added to the samples to precipitate plasma proteins. The samples were vortexed and then centrifuged at 1000 g for 15 minutes. The supernatant was decanted into glass extraction tubes and 7.5 ml of ethyl acetate was added. The extraction mixture was left at room temperature for 20 minutes, and vortexed several times during this interval. The samples were then centrifuged at 1000 g for 10 minutes, and the organic phase was removed and placed in conical-bottomed glass tubes. The organic phase was evaporated under nitrogen. The samples were reconstituted in 200 µl of mobile phase (35:65 acetonitrile:water) and transferred to an autosampler vial for HPLC injection (Waters 717 plus autosampler, Waters Corp., Milford, Mass.) The isocratic mobile phase of 35% (v/v) acetonitrile in water was pumped at a flow rate of 1 ml/min (Model 510, Waters Corp.). The stationary phase was a C18 reversed phase column (Novapak C18, 3.9×150 mm). Analytes were monitored with UV detection at 270 nm (Model 486 absorbance detector, Waters Corp.). Retention times for Compound VIII and CM-II-87 were 11.1 and 16.9 minutes, respectively. Chromatography data was collected and analyzed using Millennium software. Plasma concentrations of Compound VIII in each sample were determined by comparison to calibration curves. Calibration curves were constructed by adding known amounts of Compound VIII to dog plasma. Final Compound VIII concentrations in dog plasma samples used in the calibration curves were 0.08, 0.2, 0.4, 2, 4, 10, and 20 µg/ml. Calibration curves were linear over this concentration range and exhibited correlation coefficients (r2) of 0.9935 or greater. Intra- and inter-day coefficients of variation for the standards ranged from 6.4% for 0.08 µg/ml to 7.9% for 20 µg/ml.

Melting points were determined on a Thomas-Hoover capillary melting point apparatus and are uncorrected. Infrared spectra were recorded on a Perkin Elmer System 2000 FT-IR. Optical rotations were determined on an Autopol® III Automatic Polarimeter (Rudolph Research Model III-589-10, Fairfield, New Jersey). Proton and carbon-13 magnetic resonance spectra were obtained on a Bruker AX 300 spectrometer (300 and 75 MHz for $^1H$ and $^{13}C$, respectively). Chemical shift values were reported as parts per million (δ) relative to tetramethylsilane (TMS). Spectral data were consistent with assigned structures. Mass spectra were determined on a Bruker-HP Esquire LC System. Elemental analyses were performed by Atlantic Microlab Inc. (Norcross, Ga.), and found values were within 0.4% of the theoretical values. Routine thin-layer chromatography (TLC) was performed on silica gel on aluminum plates (silica gel 60 F 254, 20×20 cm, Aldrich Chemical Company Inc., Milwaukee, Wis.). Flash chromatography was performed on silica gel (Merck, grade 60, 230-400 mesh, 60). Tetrahydrofuran (THF) was dried by distillation over sodium metal. Acetonitrile (MeCN) and methylene chloride ($CH_2Cl_2$) were dried by distillation from $P_2O_5$.

Example 7

SARM Prodrugs Exhibit Biological Activity

Materials and Experimental Methods

Materials. Compound XI and its phosphate ester and phosphate diethyl ester are synthesized as described in Examples 1-2. Testosterone propionate (TP), polyethylene glycol 300 (PEG300, reagent grade), and dimethyl sulfoxide (DMSO) are purchased from Sigma Chemical Company (St. Louis, Mo.).

Animal. Male CD-1 mice at approximately 6 weeks of age weighing 20-27 g are purchased from Charles River Laboratory (Wilmington, Mass.). The animals are maintained on a 12-hour light-dark cycle with food and water available ad libitum. The animal protocol was reviewed and approved by the Institutional Laboratory Animal Care and Use Committee.

Study Design. Mice are weighed and randomly distributed into twelve (12) groups, with 7 animals per group. Treatment groups are depicted in Table 4. On day one of the drug treatment, animals in all groups are individually removed from the cage and anesthetized with an intraperitoneal dose of ketamine/xylazine (87/13 mg/kg). When appropriately anesthetized (i.e. no response to toe pinch), the animals' ears are marked for identification purposes. Animals are then placed on a sterile pad and their abdomen and scrotum washed with betadine and 70% alcohol. In groups 2-12, the testes are removed via a midline scrotal incision, with sterile clips used to ligate supra-testicular tissue prior to surgical removal of each testis. The surgical wound site is closed with sterile stainless steel wound clips, and antibiotic ointment is applied to the incision site. The animals in group 1 received sham surgery (midline incision with subsequent closure of the skin).

After completion of the castration, the appropriate dose is administered by oral gavage or subcutaneous injection. Dosing continues once daily for ten days, after which the mice are anesthetized with ketamine/xylazine and then euthanized by exsanguination. A portion of the blood is centrifuged at 3,000×g for 1 minute, and the plasma layer is removed and frozen at −20° C. The ventral prostates, seminal vesicles, and levator ani muscles are removed, cleared of extraneous tissue, and weighed.

The organ weights are normalized to body weight, and analyzed for any statistical significant difference by single-factor ANOVA. The weights of prostate and seminal vesicle are used as indexes to evaluate androgenic activity, and the levator ani muscle weight was used to evaluate anabolic activity.

Results

SARM prodrugs are found to have anabolic and androgenic activity in a similar ratio to the parent SARM compounds. This initial experiment is not designed to measure the exact potency of the SARM prodrugs, but rather to establish that they exhibit biological activity similar to the parent compounds.

Example 8

SARM Prodrugs are Metabolized into the Parent SARM Compound

Concentrations of Compound XI and its phosphate ester and phosphate diethyl ester are measured in plasma samples from the animals from the preceding Example at various time points before and after sacrifice. Administration of each of the above compounds results in significant levels of the parent SARM compound in plasma.

Example 9

SARM Prodrugs Exhibit a Lower Affinity of the AR than the Respective Parent Compounds The affinities of Compound XI and its phosphate ester and phosphate diethyl ester for the androgen receptor (AR) are assessed in comparative binding studies, performed as described (Marheflca C A, J Med Chem 47(4): 993-8, 2004). The parent SARM compound is found to have significantly greater affinity for the AR than either of the prodrugs. Thus, the parent compound is likely to be the biologically active compound.

Example 10

SARM Prodrugs Exhibit Different Aqueous Solubility from the Parent SARM Compound Aqueous solubility of SARM prodrugs shown to have biological activity are ascertained and compared to the parent SARM compounds. The prodrug modifications are found to alter solubility. In some cases, increased aqueous solubility is advantageous for bioavailability because it increases dissolution of the drug in the gastrointestinal tract. In other cases, decreased aqueous solubility increases bioavailability by increasing penetration of the drug through mucous membranes such as the gastrointestinal epithelium.

Example 11

SARM Prodrugs Exhibit Increased Potency Relative to the Parent SARM Compound

The experiment described in Example 7 is repeated, this time using 6 different concentrations of each compound. The results show that the prodrug modifications confer increased potency to the drugs. In some cases, the modifications improve potency by improving the bioavailabililty of the drugs. In other cases, the modifications increase the half-life of the compounds. In other cases, the modifications foster concentration of the compound in tissues where its biological activity is needed; i.e. bone tissue, muscle tissue, accessory sexual organs, etc.

Example 12

Conversion of SARM Prodrugs to the Parent SARM Compound In Vitro

Enzymatic studies are conducted to determine the mechanism of conversion of the phosphate ester and phosphate diethyl ester of Compound XI to the parent compound. The prodrugs are found to be de-phosphorylated by liver enzymes (for example alkyl phosphatases) into the parent compound, fostering intra-hepatic reabsorption and thus increasing the biological half life of the drugs. Thus, an explanation is provided for the increased potency of the prodrugs relative to the parent compounds.

It will be appreciated by a person skilled in the art that the present invention is not limited by what has been particularly shown and described hereinabove. Rather, the scope of the invention is defined by the claims that follow:

What is claimed is:

1. A prodrug of a selective androgen receptor modulator (SARM) compound, wherein said prodrug is represented by a structure of formula II-B:

II-B

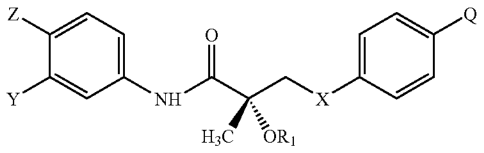

wherein

X is a bond, O, $CH_2$, NH, Se, PR, NO or NR;

Z is $NO_2$, CN, COOH, COR, NHCOR or CONHR;

Y is $CF_3$, F, I, Br, Cl, CN, $C(R)_3$ or $Sn(R)_3$;

Q is alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, or NCO;

R is alkyl, haloalkyl, dihaloalkyl, trihaloalkyl, $CH_2F$, $CHF_2$, $CF_3$, $CF_2CF_3$, aryl, phenyl, F, I, Br, Cl, alkenyl or OH; and $R^1$ is one of the stuctures:

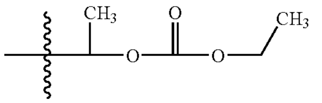

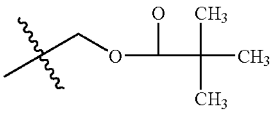

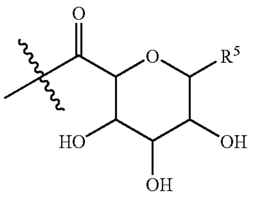

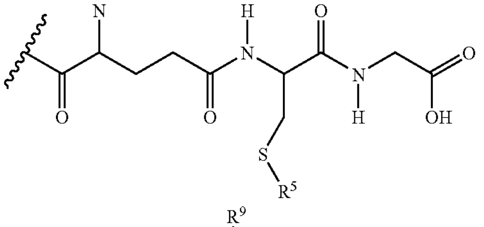

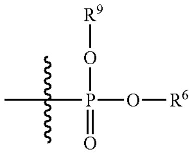

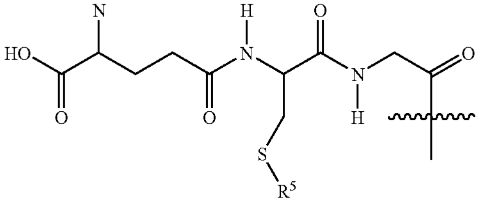

-continued

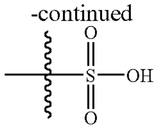

and wherein $R^5$, $R^6$, and $R^9$ are independently of each other a hydrogen, alkyl, F, I, Br, Cl, $CF_3$, CN, $CR_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR, SCN, NCS, OCN, NCO,

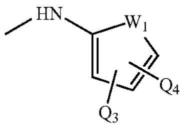

or

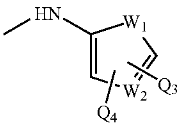

wherein $Q_3$ and $Q_4$ are independently of each other a hydrogen, alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR, SCN, NCS, OCN, or NCO.

2. A method of contraception of a male subject, comprising contacting said male subject with the prodrug of claim 1, in an amount effective to suppress sperm production in said male subject, thereby effecting contraception of a subject.

3. A method of treating a subject having a hormone-related condition, comprising contacting said subject the prodrug of claim 1, in an amount effective to effect a change in a hormone-related condition.

4. A method of treating a subject suffering from a prostate cancer in a subject, comprising contacting said subject with the prodrug of claim 1, in an amount effective to treat a prostate cancer in said subject.

5. A method of reducing an incidence of a recurrence of a prostate cancer in a subject, comprising contacting said subject with the prodrug of claim 1, in an amount effective to reduce said incidence of a recurrence of a prostate cancer in said subject.

6. A method of treating a dry eye condition in a subject, comprising contacting said subject with the prodrug of claim 1, in an amount effective to treat said dry eye condition in said subject.

7. A method of suppressing spermatogenesis in a subject, comprising contacting said subject with the prodrug of claim 1, in an amount effective to suppress sperm production.

8. The prodrug of claim 1, wherein said prodrug is represented by a structure of formula VIII-B:

VIII-B

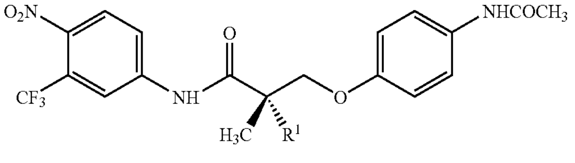

wherein $R^1$ is one of the structures:

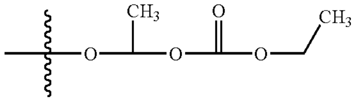

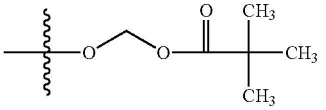

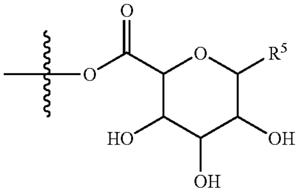

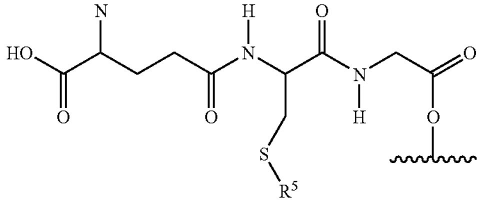

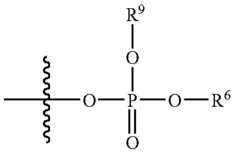

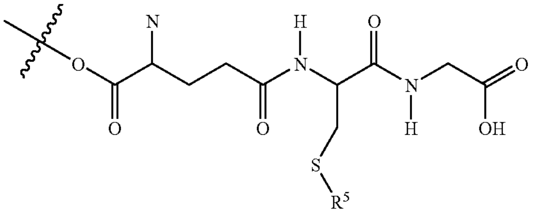

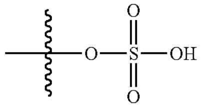

wherein $R^5$, $R^6$, and $R^9$ are independently of each other a hydrogen, alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR, SCN, NCS, OCN, NCO,

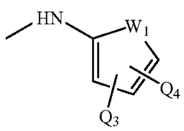

or

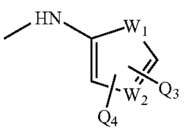

wherein $Q_3$ and $Q_4$ are independently of each other a hydrogen, alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR, SCN, NCS, OCN, or NCO.

9. The prodrug of claim 1, wherein said prodrug is represented by a structure of formula XI-B:

XI

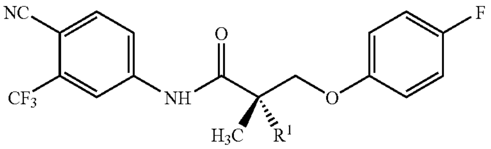

wherein $R^1$ is one of the structures:

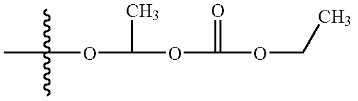

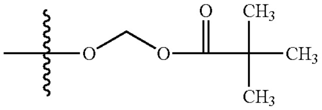

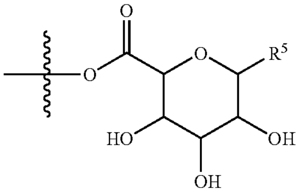

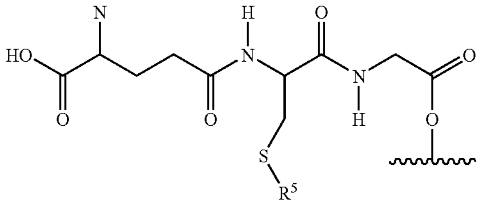

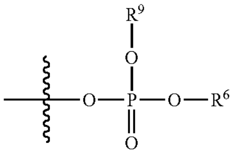

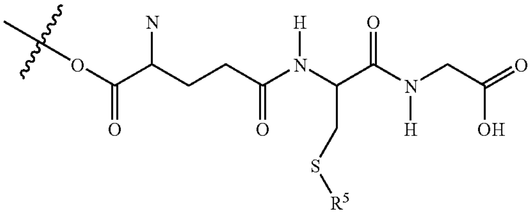

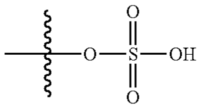

wherein $R^5$, $R^6$, and $R^9$ are independently of each other a hydrogen, alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR, SCN, NCS, OCN, NCO,

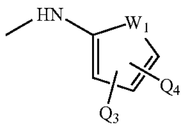

or

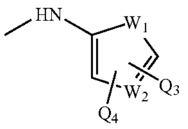

wherein $Q_3$ and $Q_4$ are independently of each other a hydrogen, alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR, SCN, NCS, OCN, or NCO.

10. The prodrug of claim 1, wherein said prodrug is represented by a structure of formula XIII-B:

XIII-B

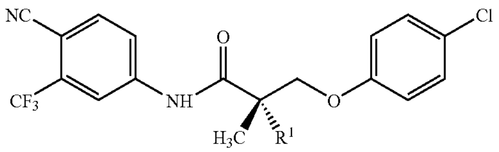

wherein $R_1$ is one of the structures:

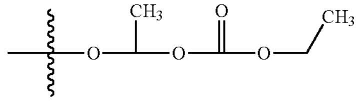

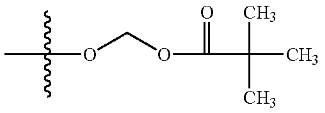

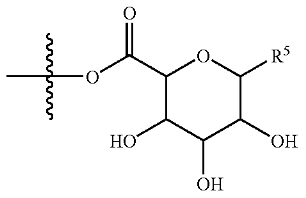

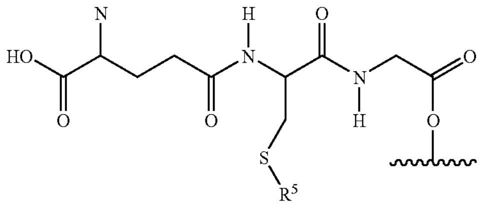

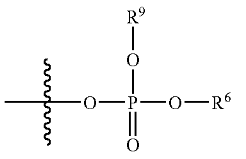

-continued

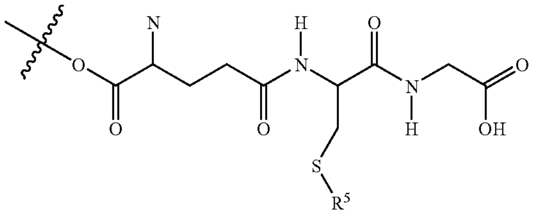

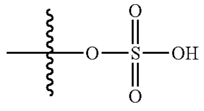

wherein $R^5$, $R^6$, and $R^9$ are independently of each other a hydrogen, alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR, SCN, NCS, OCN, NCO

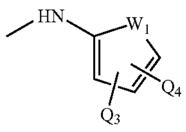

or

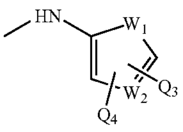

wherein $Q_3$ and $Q_4$ are independently of each other a hydrogen, alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR, SCN, NCS, OCN, or NCO.

11. The prodrug of claim 1, wherein said prodrug is represented by a structure of formula IV-B:

IV-B

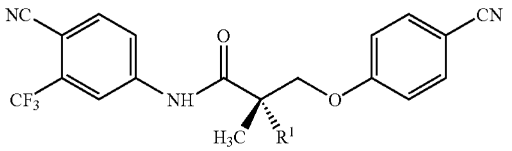

wherein $R^1$ is one of the structures:

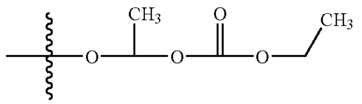

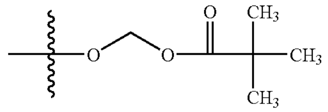

-continued

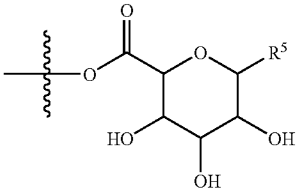

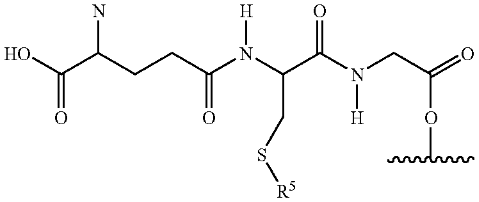

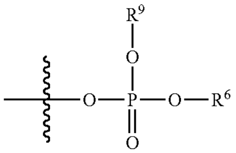

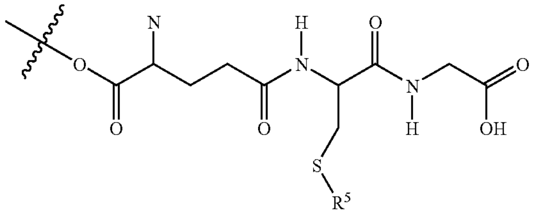

-continued

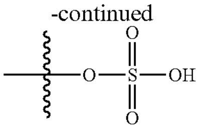

wherein $R^5$, $R^6$, and $R^9$ are independently of each other a hydrogen, alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR, SCN, NCS, OCN, NCO,

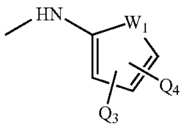

or

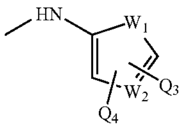

wherein $Q_3$ and $Q_4$ are independently of each other a hydrogen, alkyl, F, I, Br, Cl, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR, SCN, NCS, OCN, or NCO.

* * * * *